US010980548B2

(12) United States Patent
Huwais

(10) Patent No.: US 10,980,548 B2
(45) Date of Patent: Apr. 20, 2021

(54) AUTOGRAFTING TOOL WITH ENHANCED FLUTE PROFILE AND METHODS OF USE

(71) Applicant: Huwais IP Holding LLC, Jackson, MI (US)

(72) Inventor: Salah Huwais, Jackson, MI (US)

(73) Assignee: Huwais IP Holding LLC, Jackson, MI (US)

( * ) Notice: Subject to any disclaimer, the term of this patent is extended or adjusted under 35 U.S.C. 154(b) by 285 days.

(21) Appl. No.: 16/069,967

(22) PCT Filed: Jan. 17, 2017

(86) PCT No.: PCT/US2017/013697
§ 371 (c)(1),
(2) Date: Jul. 13, 2018

(87) PCT Pub. No.: WO2017/124079
PCT Pub. Date: Jul. 20, 2017

(65) Prior Publication Data
US 2019/0029695 A1 Jan. 31, 2019

Related U.S. Application Data

(60) Provisional application No. 62/278,579, filed on Jan. 14, 2016.

(51) Int. Cl.
*A61B 17/16* (2006.01)
*A61C 8/00* (2006.01)
(Continued)

(52) U.S. Cl.
CPC ...... *A61B 17/1615* (2013.01); *A61B 17/1673* (2013.01); *A61C 8/0089* (2013.01);
(Continued)

(58) Field of Classification Search
CPC ............ A61B 17/1615; A61B 17/1628; A61B 17/1673; A61C 8/0089
See application file for complete search history.

(56) References Cited

U.S. PATENT DOCUMENTS

| 811,111 A | 1/1906 | Wegefarth |
| 2,113,178 A | 4/1938 | Gase |
| (Continued) | | |

FOREIGN PATENT DOCUMENTS

| CA | 2590344 C | 10/2017 |
| CN | 2232727 | 8/1996 |
| (Continued) | | |

OTHER PUBLICATIONS

Anitua, Ridge expansion with motorized drills, Implant Dialogue, 14 pgs.
(Continued)

*Primary Examiner* — Anu Ramana
(74) *Attorney, Agent, or Firm* — Endurance Law Group PLC

(57) ABSTRACT

Tools and methods for expanding a precursor hole in a host material to receive a fixture. The precursor hole is enlarged by a rotary tool having helical flutes and interposed lands. The flutes have a negative rake angle. The lands each have a working edge that cuts the host material when the tool is rotated in a cutting direction, and that condenses the host material when the tool is rotated in a densifying direction. The body of the rotary tool has a stopper section that plugs the hole when a certain depth is reached. When the tool is used with a copious wash of irrigating fluid at or below the necessary depth, hydraulic pressure builds inside the precursor hole. The hydraulic pressure can be advantageously
(Continued)

exploited in cutting mode to autograft a slurry of host material particles into the sidewalls of the hole and create an incipient densifying crust.

10 Claims, 38 Drawing Sheets

(51) Int. Cl.
    *A61B 90/00*     (2016.01)
    *A61B 17/17*     (2006.01)

(52) U.S. Cl.
    CPC ....... *A61B 17/1628* (2013.01); *A61B 17/1728* (2013.01); *A61B 2017/1602* (2013.01); *A61B 2090/062* (2016.02)

(56) References Cited

U.S. PATENT DOCUMENTS

| | | |
|---|---|---|
| 2,489,179 A | 11/1949 | Hartman |
| 3,556,669 A | 1/1971 | Valeska et al. |
| D269,040 S | 5/1983 | Deemer |
| 4,474,556 A | 10/1984 | Ellis et al. |
| 4,850,867 A | 7/1989 | Senia et al. |
| 5,220,964 A | 6/1993 | Deken et al. |
| 5,377,773 A * | 1/1995 | Tibbitts .................. E21B 10/43 175/397 |
| 5,443,468 A | 8/1995 | Johnson |
| 5,489,179 A | 2/1996 | Gabriel et al. |
| 5,536,127 A | 7/1996 | Pennig |
| 5,688,120 A | 11/1997 | Yacker et al. |
| 5,702,443 A | 12/1997 | Brånemark |
| 5,735,689 A | 4/1998 | McSpadden |
| 5,891,146 A | 4/1999 | Simon et al. |
| 6,146,138 A | 11/2000 | Dalmau |
| 6,179,616 B1 | 1/2001 | Danger |
| 6,186,787 B1 | 2/2001 | Danger et al. |
| 6,264,677 B1 | 7/2001 | Simon et al. |
| 6,561,805 B2 | 5/2003 | Kumar |
| 6,641,395 B2 | 11/2003 | Kumar et al. |
| 7,198,488 B2 | 4/2007 | Lang et al. |
| 7,241,144 B2 | 7/2007 | Nilo et al. |
| 7,247,020 B2 | 7/2007 | Takahashi et al. |
| 7,300,281 B2 | 11/2007 | Cantatore et al. |
| 7,402,040 B2 | 7/2008 | Turri |
| 7,435,086 B2 | 10/2008 | Berutti et al. |
| 7,488,327 B2 | 2/2009 | Rathbun et al. |
| 7,547,210 B1 | 6/2009 | Valen |
| D611,511 S | 3/2010 | Aldecoa |
| 7,766,657 B2 | 8/2010 | Jaunberzins |
| 9,326,778 B2 | 5/2016 | Huwais |
| 10,040,136 B2 * | 8/2018 | Shpigelman ............ B23C 5/10 |
| 2002/0094508 A1 | 7/2002 | Lorenzi |
| 2004/0223830 A1 | 11/2004 | Panasik et al. |
| 2004/0230195 A1 | 11/2004 | Kaikkonen et al. |
| 2005/0118550 A1 | 6/2005 | Turri |
| 2005/0123364 A1 | 6/2005 | Zhou |
| 2005/0273110 A1 | 12/2005 | Boehm et al. |
| 2006/0018733 A1 | 1/2006 | Dill et al. |
| 2006/0111724 A1 | 5/2006 | Ping |
| 2006/0121415 A1 | 6/2006 | Aldecoa |
| 2006/0127847 A1 | 6/2006 | Danger et al. |
| 2006/0210949 A1 | 9/2006 | Stoop |
| 2007/0037117 A1 | 2/2007 | Jaunberzins |
| 2009/0136898 A1 | 5/2009 | Kim |
| 2009/0142731 A1 | 6/2009 | Kim |
| 2009/0259227 A1 | 10/2009 | Ahn |
| 2010/0266984 A1 | 10/2010 | Jung |
| 2010/0273128 A1 | 10/2010 | Aldecoa |
| 2010/0291511 A1 | 11/2010 | Lee |
| 2010/0297578 A1 | 11/2010 | Jaunberzins |
| 2010/0316456 A1 | 12/2010 | George |
| 2010/0330534 A1 | 12/2010 | Hyun |
| 2012/0197311 A1 | 8/2012 | Kirschman |
| 2012/0244497 A1 * | 9/2012 | Huwais ................ A61C 3/02 433/165 |
| 2013/0218160 A1 | 8/2013 | Frimanson |
| 2015/0097305 A1 | 4/2015 | Hufschmied |
| 2015/0173776 A1 | 6/2015 | Burke et al. |
| 2015/0297243 A1 | 10/2015 | Kulas et al. |
| 2015/0297275 A1 | 10/2015 | Huwais |

FOREIGN PATENT DOCUMENTS

| | | |
|---|---|---|
| CN | 2318985 | 5/1999 |
| CN | 1246040 A | 3/2000 |
| CN | 2724645 | 9/2005 |
| CN | 101229072 A | 7/2008 |
| CN | 101292906 A | 10/2008 |
| DE | 102004010859 A1 | 4/2005 |
| DE | 102004010856 A1 | 6/2005 |
| DE | 102004010858 A1 | 6/2005 |
| DE | 102004010860 A1 | 6/2005 |
| EP | 0379201 A2 | 7/1990 |
| EP | 1273273 A2 | 1/2003 |
| EP | 1749498 A1 | 2/2007 |
| EP | 2119403 A1 | 11/2009 |
| EP | 1752109 B1 | 10/2010 |
| FR | 2594684 A | 8/1987 |
| JP | 10217030 A | 8/1998 |
| KR | 101128730 B1 | 3/2012 |
| WO | 2005011514 A2 | 2/2005 |
| WO | 2007086622 A1 | 8/2007 |
| WO | 2011053588 A1 | 5/2011 |
| WO | 2014077920 A1 | 5/2014 |
| WO | 2015020118 A1 | 2/2015 |
| WO | 2015138842 A2 | 9/2015 |
| WO | 2015138842 A3 | 11/2015 |
| WO | 2015172842 A1 | 11/2015 |

OTHER PUBLICATIONS

Biohorizons, VIP Catalog and Surgical Manual, 2008, 28 pgs.
Biomet Sports Medicine, Bone Dowel Harvester, Copyright 2007, Biomet Sports Medicine, Inc., PO Box 587, Warsaw, IN 46581-0587 (www.biometsportsmedicine.com).
Calvo-Guirado JL et al. "Compressive osteotomes for expansion and maxilla sinus floor lifting," Med Oral Patol Oral Cir Bucal 2006;11:E52-5.
Goyal et al., Bone Manipulation Techniques, International Journal of Clinical Implant Dentistry, Jan.-Apr. 2009; 1(1): pp. 22-31.
Lee, Atraumatic Ridge Expansion and Implant Site Preparation with Motorized Bone Expanders, Practical Procedures and Aesthetic Dentistry 2006; 18(1): pp. A-F.
Meisinger, Bone Management catalog, pp. 161-178.
Meisinger, Split-Control, retrieved Mar. 10, 2012 from www.bone-management.com/eng/bm_sortimente_anw_split_eng.htm.
Nishioka, Bone Spreading Technique (Dec. 9, 2010), retrieved Mar. 10, 2012 from www.dentistrytoday.com/implants/4228-bone-spreading-technique, pp. 1-4.
Steier et al., Better horizontal ridge expansion, Dental Tribune I, Sep. 22-28, 2008, pp. 9-10.
Summers, A New Concept in Maxillary Implant Surgery: The Osteotome Technique, Compend Contin Educ Dent, vol. XV, No. 2, pp. 152-160.
www.dentsply-friadent.com, "Ankylos Surgical Manual."
www.nobelbiocare.com, "Validating Innovation: NobelActive Technical and Clinical Story," Nobel Biocare Services AG, 2011.

* cited by examiner

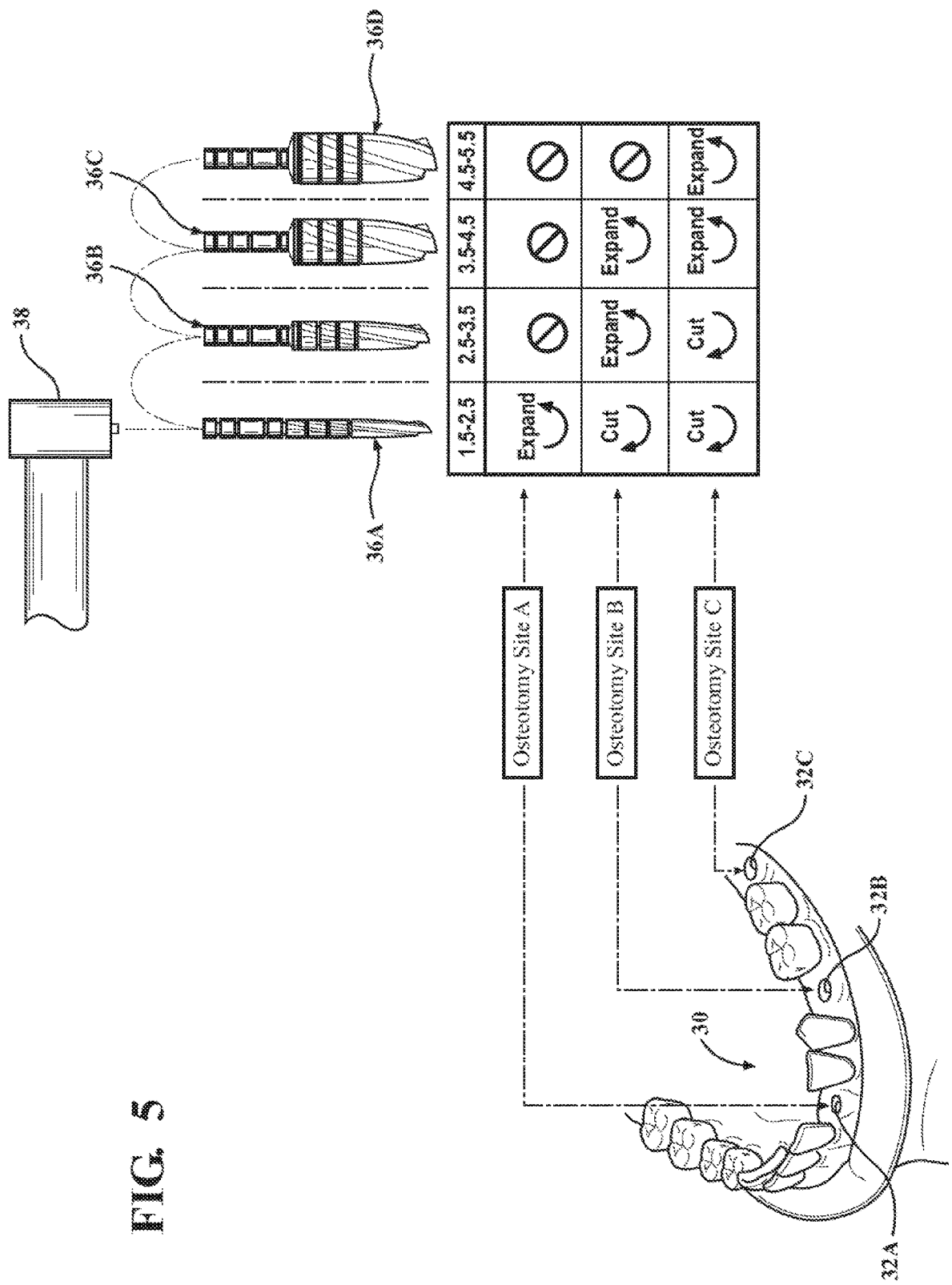

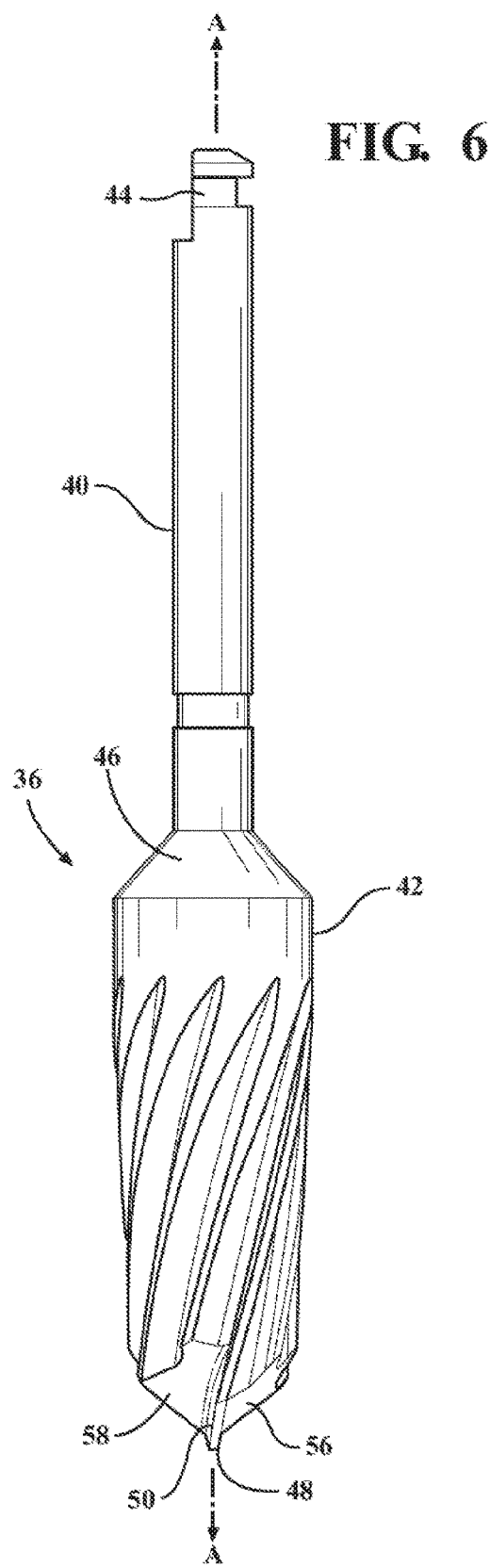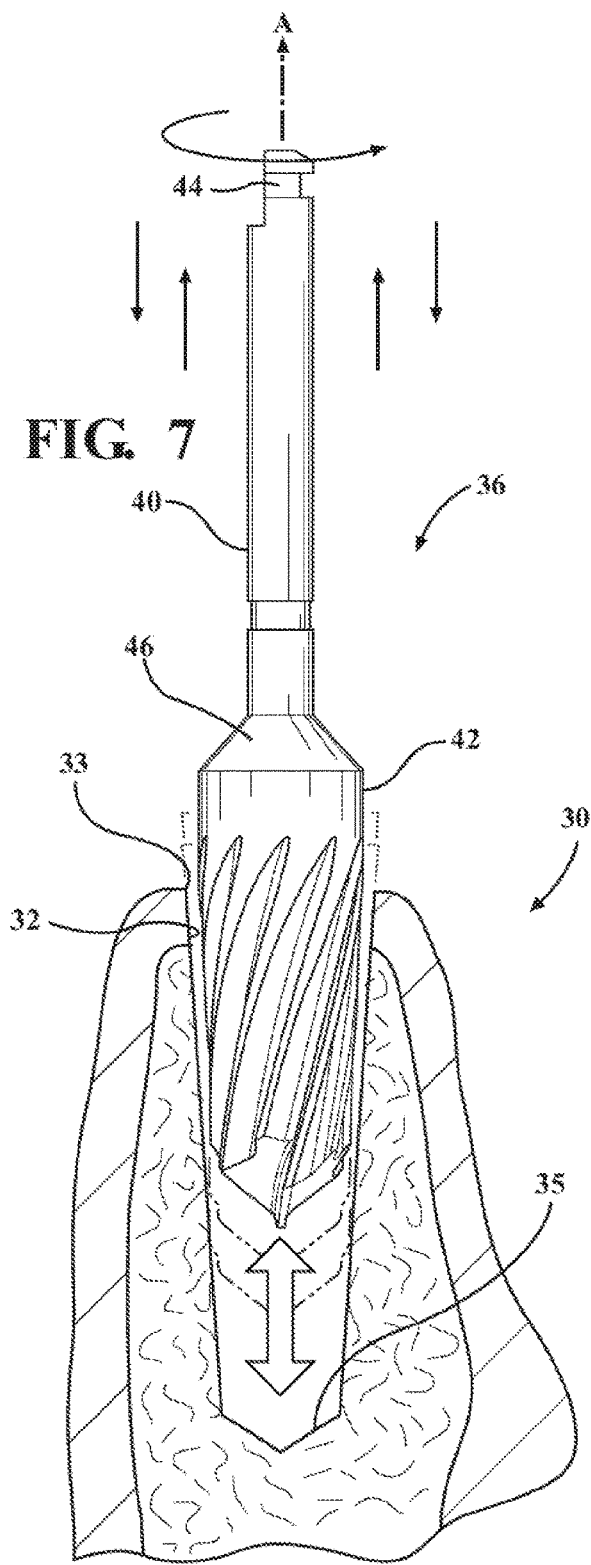

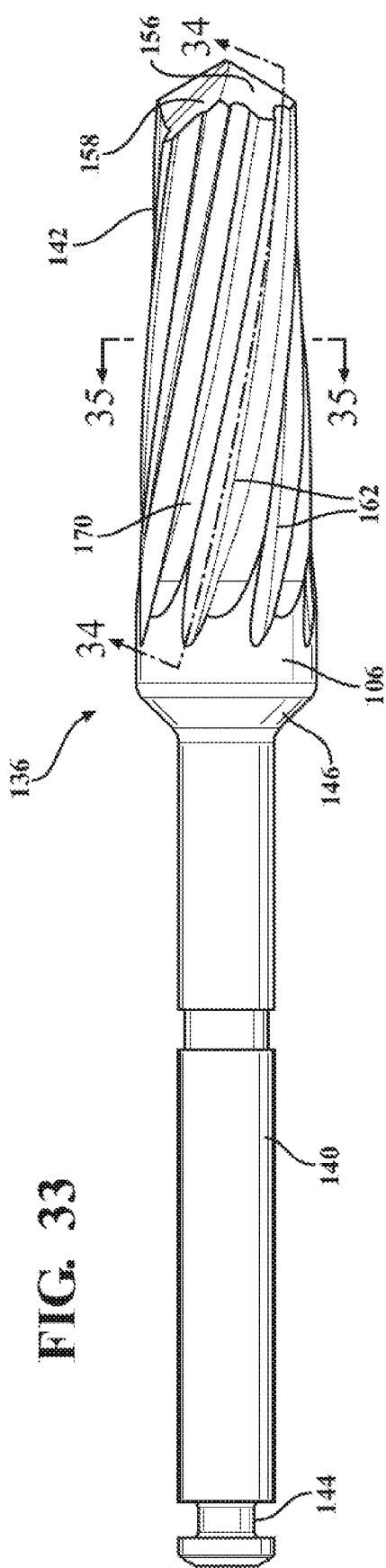
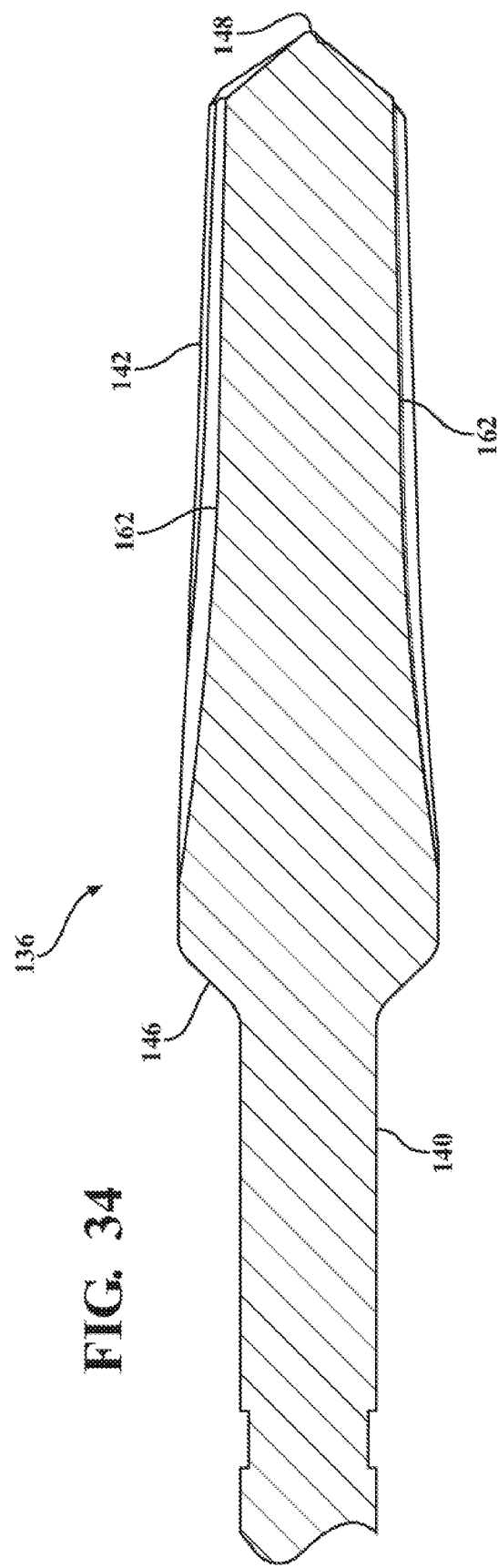

AUTOGRAFTING TOOL WITH ENHANCED FLUTE PROFILE AND METHODS OF USE

BACKGROUND OF THE INVENTION

Field of the Invention

The invention relates generally to tools for preparing a hole to receive an implant or fixture, and more particularly to rotary osteotomes and methods implemented thereby for expanding an osteotomy or hole in an inorganic material to receive an implant or other fixation device.

Description of Related Art

An implant is a medical device manufactured to replace a missing biological structure, to support a damaged biological structure, or to enhance an existing biological structure. Bone implants are implants of the type placed into the bone of a patient. Bone implants may be found throughout the human skeletal system, including dental implants in a jaw bone to replace a lost or damaged tooth, joint implants to replace a damaged joint such as in hips and knees, and reinforcement implants installed to repair fractures and remediate other deficiencies like pedicle screws used in spinal stabilization, to name but a few. The placement of an implant often requires a preparation into the bone using either hand osteotomes or precision drills with highly regulated speed to prevent burning or pressure necrosis of the bone. After a variable amount of time to allow the bone to grow onto the surface of the implant, sufficient healing will enable a patient to start rehabilitation therapy or return to normal use or perhaps the placement of a restoration or other attachment feature.

There are several known ways to form a receiving hole or osteotomy. Since the early days of implantology, for example, osteotomies have been prepared using standard drills that look and handle much like drills designed for use in industrial applications. These drill designs have proven to be functional for dental and medical applications, however noticeably imperfect. Implant success rates have been satisfactory over time but osteotomy preparation techniques have still been lacking for various reasons. Standard drill designs used in dental and medical implantology are made to excavate bone to create room for the implant to be placed, just like a drill designed for non-medical applications. Standard drill designs, in twist or fluted shapes, cut bone effectively but typically do not produce a clean, precise circumferential osteotomy. Osteotomies may become elongated and elliptical due to chatter because the drills are very aggressive cutters. In circumstances where the osteotomy is imperfectly round, the implant insertion torque may be reduced, leading to poor primary stability and potential lack of integration. Osteotomies drilled into narrow bone locations may produce dehiscence, buccally or lingually, which also reduces primary stability and will require an additional bone grafting procedure, which adds cost and healing time to treatment.

More recently, a novel biomechanical bone preparation technique called "osseodensification" has been pioneered by the Applicant of this invention. The osseodensification technique is based on the preservation of host bone, and has gained rapid acceptance in the dental community. In some instances, osseodensification is considered a preferred standard of care. Examples of osseodensification can be seen in U.S. Pat. No. 9,028,253, issued May 12, 2015, and in U.S. Pat. No. 9,326,778, issued May 3, 2016, and PCT Publication No. WO 2015/138842, published Sep. 17, 2015. The entire disclosures of these references are hereby incorporated by reference and relied upon to the extent permitted by the relevant national jurisdiction.

Generally described, osseodensification is a procedure for enlarging an osteotomy using a specially-designed, multi-fluted, rotary osteotome, or bur. An example of a suitable rotary osteotome is described in the above-mentioned U.S. Pat. No. 9,326,778. Rotary osteotomes for dental applications are marketed as Densah® Burs through Versah, LLC of Jackson, Mich. USA, a licensee of the Applicant.

Unlike traditional drilling techniques, osseodensification does not excavate bone tissue. Rather, bone tissue is simultaneously compacted and auto-grafted in outwardly expanding directions from the osteotomy, somewhat akin to a traditional hammered osteotome but without the trauma and other limitations of that technique. When rotated at high speed in a reversed, non-cutting direction with steady external irrigation, these rotary osteotomes form a strong and dense layer of bone tissue along the walls and base of the osteotomy. Dense compacted bone tissue produces stronger purchase for the surgeon's favorite implant and may facilitate faster healing.

Briefly, an example of dental implantology may be used to illustrate the general principles of the osseodensification technique. The osteotomy site is first prepared with a precursor pilot hole drilled with a small, e.g., 1.5 mm, standard medical-grade twist drill or other boring tool. (Of course, the circumstances of any given surgical application, whether dental or non-dental in nature, will dictate the size of precursor pilot hole and other characteristics of the operation.) The precursor pilot hole is drilled to a predetermined depth. Using a rotary osteotome designed for osseodensification, the surgeon decides whether to enlarge the precursor pilot hole either by densifying or cutting, taking into account situational factors which may include hardness of the bone, final intended osteotomy/implant size, local width of bone formation, and other relevant factors.

If the surgeon decides to enlarge the precursor pilot hole by cutting, the specially designed rotary osteotome is rotated in a cutting direction at high speed. High speed is defined as generally above 200 RPM for rotary osteotomes in the range of about 1.5 mm to 6 mm in diameter. The rotary osteotome is advanced into the precursor pilot hole, often with a gentle pumping motion and abundant irrigation. On its descent, the working edges of the rotary osteotome cut bone materials into small chips or particles, which accumulate in the flutes. The bone particles are subsequently discarded or collected/harvested if desired for later use. The osteotomy can likewise be further enlarged by cutting (or densifying) in one or more subsequent operations using progressively larger rotary osteotomes.

On the other hand, if the surgeon prefers to enlarge the precursor pilot hole by densifying, the same rotary osteotome is used but instead rotated in a non-cutting direction at high speed. If the rotary osteotome is designed so that its cutting direction is clockwise (as is typical with most twist drills), then the non-cutting direction for that same rotary osteotome would be counter-clockwise. I.e., the non-cutting or densifying direction is the reverse of the cutting direction. When densifying, the surgeon advances the counter-spinning rotary osteotome into the precursor pilot hole (or a precursor hole formed by a previous expansion operation like that described in the preceding paragraph), together with copious irrigation. Downward pressure applied by the surgeon is needed to keep the working edges of the rotary osteotome in contact with the bone surface inside the osteotomy, often with the above-mentioned gentle bouncing motion to modulate the pressure and thereby avoid overheating and over-straining of bone tissue. The harder the surgeon pushes the rotary osteotome into the osteotomy, the more pressure is exerted laterally, both mechanically and through hydrodynamic effects enabled by the concurrent irrigation. Care is taken to maintain alignment between the longitudinal axis of the rotary osteotome and the bore axis of the osteotomy at all times. Once the rotary osteotome has reached the full intended depth, enlargement with that rotary osteotome is complete. The osteotomy can then be further enlarged by densifying with one or more subsequent operations using progressively larger rotary osteotomes following the same procedures.

Biomechanical as well as histological validation studies of the osseodensification technology have concluded that, in porcine tibia and Sheep Illiac Crest, osseodensification facilitates bone expansion, increases implant stability and creates a densification layer around the preparation site by compacting and autografting bone particles along the entire depth of the osteotomy.

Although described up to now in the context of medical applications, these same techniques are applicable to non-bone materials. Some industrial applications, including those which require the placement of screwed anchors into foamed metals, cellular compositions, and other non-organic materials, may be accepting of and benefit from the general principles of this technology.

Osseodensification is a relatively new field. As with any emerging technology, new and improved tools and techniques are expected as the technology begins to mature and be perfected. Furthermore, there is a continuing need to improve the efficiency of surgical operations to make them faster and easier to perform. Therefore, any improvements in osseodensification tools and/or techniques that advances the base technology, and that improves efficiency, will be welcomed by the relevant medical and industrial communities.

BRIEF SUMMARY OF THE INVENTION

According to a first aspect of this invention, a rotary osteotome comprises a shank that establishes a longitudinal axis of rotation. A body extends from the shank. The body has an apical end that is remote from the shank. A plurality of helically spiraling flutes are disposed about the body. Each flute has a cutting face on one side thereof defining a rake angle and a densifying face on the other side thereof defining a heel-side angle. The flutes have an axial length and radial depth. A stopper section of the body is disposed between the flutes and the shank. A land is formed between each adjacent pair of flutes. Each the land has a working edge along the cutting face of the one adjacent flute. The working edge helically twists about the body. The flutes are formed with a continuously negative rake angle along their full lengths.

The negative rake angles in combination with the stopper section enable the rotary osteotome to achieve a heretofore unachievable effect, namely the incipient formation of a densifying crust in the surrounding osteotomy (i.e., hole) while being operating in a cutting mode.

According to another aspect of this invention, a method for enlarging a precursor hole in a host material is provided. The precursor hole is enlarged in preparation to receive a screw-in fixture with heightened initial stability. The method comprises a series of steps, which include making available a rotary tool configured to be turned at high speed in a cutting direction. The tool comprises a shank and a body joined to the shank. The body has an apical end remote from the shank. A plurality of flutes disposed about the body. The flutes has a helical twist. Each flute has a densifying face and an opposing cutting face. A stopper section of the body disposed between the flutes and the shank. The body also has a plurality of lands. Each land is formed between two adjacent flutes. Each land has a land face joining a densifying face of one flute and a cutting face of the other flute. Each land face intersects the respective the cutting face along a working edge. The steps further include irrigating a precursor hole in a host material. The precursor hole is of the type having an interior surface extending between a generally circular entrance and a bottom closed by the host material. The steps include rotating the body of the tool in a cutting direction greater than about 200 RPM. The cutting direction is defined as rotationally sweeping the cutting faces into the host material. Step steps furthermore include enlarging the precursor hole by forcibly pushing the rotating body to the bottom of the precursor hole so that the working edges cut the host material and a slurry of host material particles mixed with irrigating liquid accumulates in the flutes. This latter step of enlarging the precursor hole includes concurrently plugging the hole with the stopper section of the body while continuing to apply axial force to pressurize the slurry thereby autografting (i.e., embedding) at least some of the host material particles that had accumulated in the flutes directly into the side walls of the hole.

The method of this invention enable formation of a hole in a cutting mode possessing the early formation of a densifying crust within its side walls to provide a later installed fixture to be screwed into the hole with a heightened initial stability.

These and other aspects of the invention will be understood more fully by considering the detailed description and illustrations of this invention.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 5 is a diagrammatic view illustrating by way of example the use of a surgical kit containing four osteotomes of progressively larger diameter according to the present invention in combination with a reversible drill motor to concurrently prepare three separate osteotomy sites in a human jaw using selective reversal of osteotome direction to enlarge each osteotomy either by cutting or burnishing without removing the osteotome from the surgical drill motor;

FIG. 6 is a side elevation view of a rotary osteotome according to one embodiment of this invention;

FIG. 7 is a simplified cross-sectional view showing a surgical procedure referred to herein as "bounce" where an osteotome according to the present invention is repeatedly pushed into the osteotomy and withdrawn while the osteotome remains spinning in a repetitive manner so as to enlarge the osteotomy while enabling the surgeon to manage the expansion rate (and other factors) while making adjustments on-the-fly;

FIG. 33 is a side elevation of an enhanced rotary osteotome according to an alternative embodiment of this invention;

FIG. 34 is a cross-sectional view taken helically along 34-34 in FIG. 33;

DETAILED DESCRIPTION OF THE INVENTION

Figure 1:
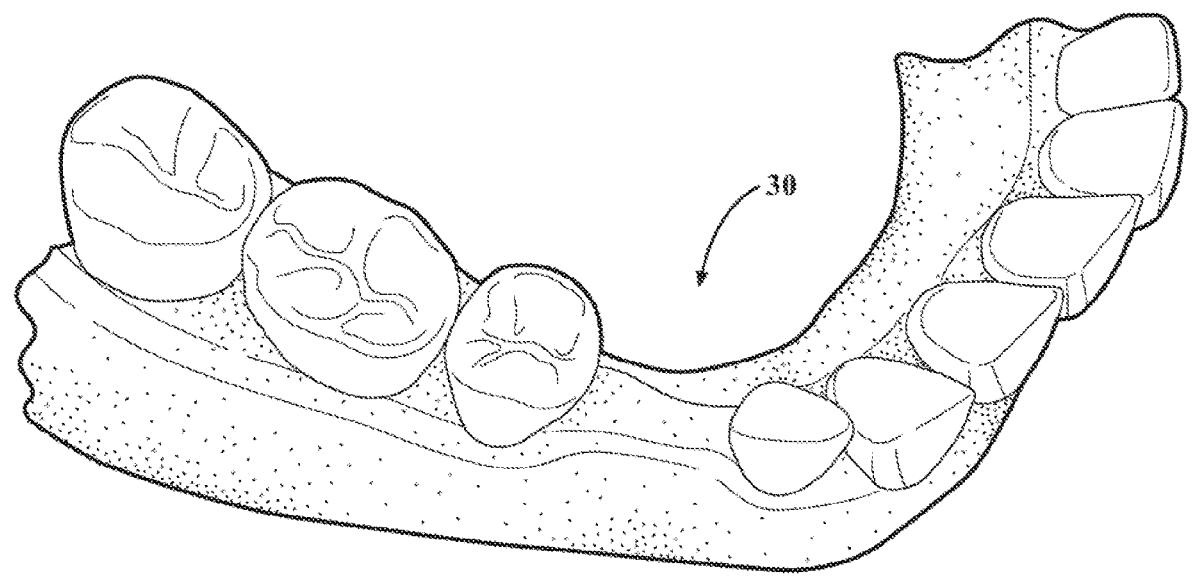
FIG. 1 depicts an exemplary application of the present invention at an edentulous (without teeth) jaw site that needs expansion to receive an implant.
Figure 2:
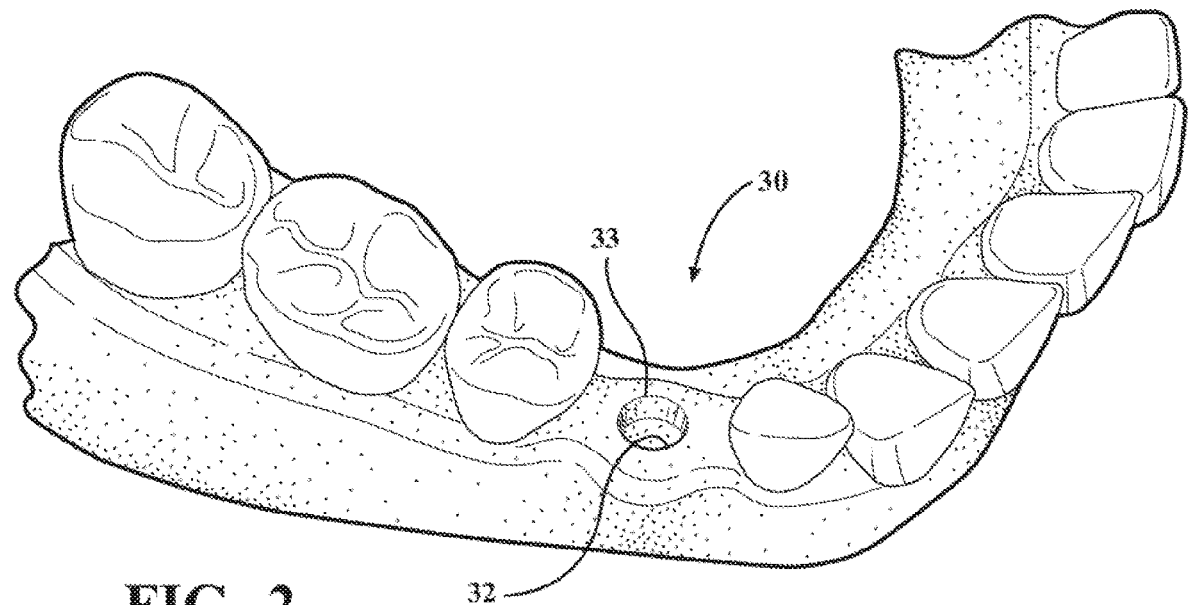
FIG. 2 is a view as in FIG. 1, but showing the resulting fully prepared osteotomy as achieved through use of the present invention in a progressive series of expansion steps.
Figure 3:
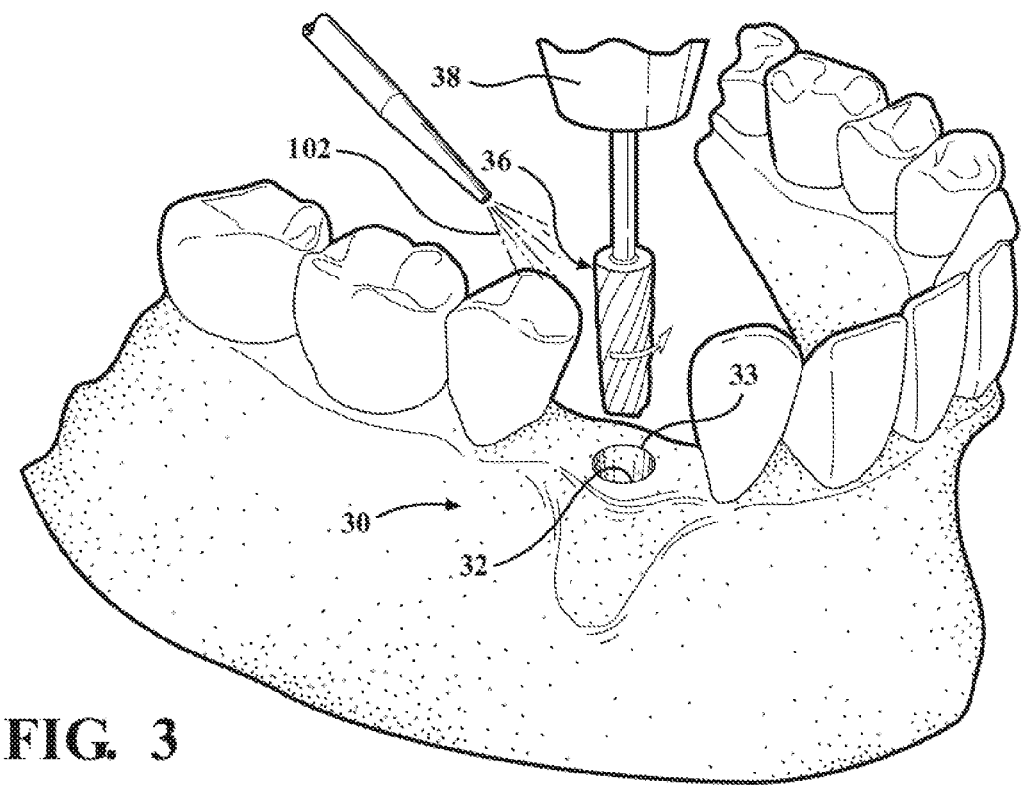
FIG. 3 is a view as in FIG. 1 showing a progressive expansion step with a rotary osteotome according to one embodiment of this invention.
Figure 4:
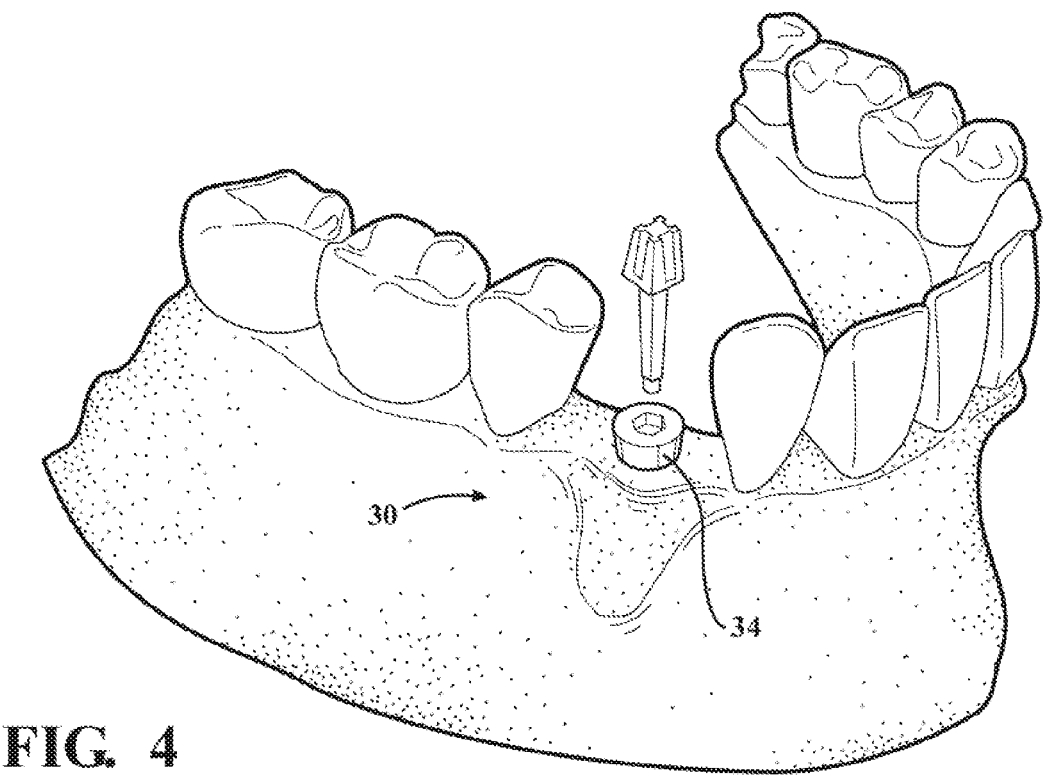
FIG. 4 is a view as in FIG. 2 in which an installed implant is poised to receive an abutment or base for subsequent prosthetic (not shown)

Referring to the figures, wherein like numerals indicate like or corresponding parts throughout the several views, FIGS. 1-4 show the example of a dental implant, in which preparation of an osteotomy is required to receive a bone implant (FIG. 4). It will be understood that this invention is not limited to dental applications, but may be applied across a wide spectrum of orthopedic applications. Human applications are typical, but animal applications are equally plausible and not outside the scope of this invention. Furthermore, the invention is not even limited to bone applications, but may be used to prepare holes in non-organic materials for industrial and commercial applications, including but not limited to metal foam and other cellular materials to name but a few. In FIG. 1, an edentulous (without teeth) jaw site 30 is shown that needs expanded and prepared as a final fully-formed osteotomy 32 (FIG. 2) in order to receive an implant 34 (FIG. 4) or other fixture device. A series of steps are required to accomplish the fully-formed osteotomy 32 of FIG. 2. The series of steps include first boring a pilot hole into the recipient bone to form the initial osteotomy (not shown), then incrementally expanding the osteotomy using progressively wider rotary expander devices or osteotomes, generally indicated at 36, as shown in FIG. 3, until a final intended diameter is achieved. Once the osteotomy has been prepared, the implant 34 or fixture screw is screwed into place as illustrated in FIG. 4. The procedure of forming an osteotomy is described, generally, below.

FIG. 5 is a diagrammatic view illustrating by way of example the use of a surgical kit containing four osteotomes 36A-D of progressively larger diameter according to the present invention in combination with a reversible surgical drill motor 38. The pilot drill is not shown in this example. The surgical kit may be used to concurrently prepare three separate osteotomy sites 32A, 32B and 32C, respectively, in a human jaw bone 30 using the rotary osteotomes 36A-D and selectively reversing rotational direction to enlarge each osteotomy either by cutting or compacting without removing a given osteotome 36 from the surgical drill motor 38. Although the example is presented here again in the context of a dental application, the described techniques are adaptable to non-dental applications including, but not limited to, joint replacement, bone fixations generally as well as inorganic industrial uses (see for examples FIGS. 27B and 28).

In the example of FIG. 5, a first osteotomy site 32A is located in the front of the mandible bone 30 where the bone width is relatively narrow. The composition of the bone 30 in the region of the first osteotomy site 32A may be described as predominantly Type II, as an example. A second osteotomy site 32B is located slightly posterior of the first site 32A in a region of the mandible that has moderate bone 30 width. The composition of the bone 30 in the region of the second osteotomy site 32B may be described as generally a combination of Types II and III, in this example. A third osteotomy site 32C is located in a molar region of the mandible and is surrounded by a relatively generous ridge width of the bone 30. The composition of the bone 30 in the region of the third osteotomy site 32C may be described as predominantly Type III in this example. Due to the varying ridge widths and compositions of bone 30 at sites 32A, 32B and 32C, the surgeon may not wish to apply the same protocol at each site. By using the present invention, a surgeon (or user in non-surgical applications) has the ability to concurrently prepare all three osteotomy sites 32A-32C in different ways but using the same set of rotary osteotomes 36A-D in a highly efficient manner.

In this example, each osteotomy site 32A-32C is presumed to have a precursor osteotomy prepared by first drilling a pilot hole of 1.5 mm. (Of course, the circumstances of any given surgical application, whether dental or non-dental in nature, will dictate the size of precursor hole and other characteristics of the operation.) The precursor hole that extends from an entrance 33 or rim in the exposed surface of the bone (or in the flesh if not previously resected) to a bottom 35. The entrance 33 is identified in FIGS. 2 and 3, whereas the bottom 35 is identified in FIGS. 7 and 11. The surgeon locks or otherwise installs the first rotary osteotome 36A into the drill motor 38 and sets the rotational direction to a non-cutting direction, which in this example is counter-clockwise as viewed from the top (i.e., the surgeon's perspective). Although the surgeon may vary the rotational speed of the osteotome 36 according to the dictates of the situation, experimental results indicate that high rotation speeds, i.e., greater than about 200 RPM, and torque settings between about 5-50 Ncm will provide satisfactory results. High speed rotation is considered anything above about 200 RPM for rotary osteotome 36 diameters in the range of about 1.5 mm to 6 mm. Upper ranges for these relatively small diameter rotary osteotomes may reach about 2000 RPM. More preferably rotation speeds between about 600-1800 RPM and torque settings between about 20-45 Ncm provide satisfactory results. And still more preferably, rotation speeds in the range of 800-1500 RPM and torque settings of about 35 Ncm provide satisfactory results. As the diameter of the osteotome 36 increases, however, it may be desirable to reduce the recommended rotational speeds. Speeds suggested here apply in context to the exemplary dental applications. Relatively large diameter rotary osteotomes 36 used for large-bone orthopedic applications like femurs may require slower rotational speeds than rotary osteotomes 36 used for smaller bone applications due to tangential velocity considerations at the working edges. That is to say, as a guiding principle for large diameter rotary osteotomes 36, it may be advantageous to maintain tangential velocity (as measured at the working edges 72) between about 0.02 m/s on the low end and about 0.6 m/s on the high end to create a suitable compression wave in the bone needed to accomplish osseodensification.

The surgeon pushes the rotating first osteotome 36A into the first osteotomy site 32A to expand the initial pilot hole through compacting (the details of which are described in detail below). This is referred to as the densifying (non-cutting) mode of operation, and will be described in technical terms below. However, due to the different compositional nature of the second 32B and third 32C osteotomy sites, the surgeon chooses to enlarge these other sites 32B, 32C by cutting rather than compacting. To affect this, the surgeon reverses the rotational direction of the drill motor 38 to clockwise without removing the first osteotome 36A from the drill motor 38. High speed rotation is used in both densifying and cutting modes. Using a similar modulated pushing motion, the surgeon enlarges the second 32B and third 32C osteotomy sites by removing bone material which may, if desired, be harvested. This is referred to as the cutting mode of operation, and will be described further below. A continuous flow of irrigating fluid is used throughout the procedures.

At this stage in the hypothetical example, the first osteotomy site 32A has been expanded as much as the surgeon desires; no further expansion is needed of the first osteotomy site 32A, as the intention is to place a small-diameter implant in the first osteotomy site 32A. However, the second 32B and third 32C osteotomy sites both require additional expansion, as the intended implants for those sites have a larger diameter. The surgeon then installs the second osteotome 36B into the drill motor 38 and sets the rotational direction on the drill motor 38 to counter-clockwise (non-cutting direction). The previously expanded holes in the second 32B and third 32C osteotomy sites are now considered precursor holes to the subsequent operations, each with an entrance 33 in the exposed surface of the bone and a closed bottom 35. Skipping the completed first osteotomy site 32A, the surgeon then expands the second osteotome 36B into the second osteotomy site 32B using the densifying mode described above. Due to the different compositional nature of the third osteotomy site 32C, however, the surgeon chooses to enlarge by cutting rather than compacting. To affect this, the surgeon changes the rotational direction of the surgical motor 38 and, using a similar pushing motion, proceeds to enlarge the third osteotomy site 32C using the cutting mode.

Once the remaining two osteotomy sites 32B, 32C have been enlarged by the second osteotome 36B, the surgeon installs the third osteotome 36C into the drill motor 38 and sets the rotational direction to counter-clockwise. Again skipping the completed first osteotomy site 32A, the second 32B and third 32C osteotomy sites are enlarged by compacting. In both cases, the surgical motor 38 is set to turn in the counter-clockwise direction and the previously expanded holes are deemed precursor holes to the subsequent operations. The second osteotomy site 32B has now been expanded as much as the surgeon desires; no further expansion is needed of the second osteotomy site 32B. However, the third osteotomy site 32C still requires additional expansion, as the intended implant for the third site 32C has a larger diameter than the implant to be placed in the second osteotomy site 32B. Therefore, the surgeon installs the fourth osteotome 36D into the drill motor 38 and sets the rotational direction to counter-clockwise. The enlargement accomplished by the third osteotome 36C now comprises a precursor hole for the next operation at the third osteotomy site 32C, with its newly enlarged entrance 33 in the exposed surface of the bone and a still closed bottom 35. Skipping the completed first 32A and second 32B osteotomy sites, the third 32C osteotomy site is further enlarged using the previously described densifying mode technique. Appropriately sized implants 34 (or fixture portions of implants) can now be installed at each osteotomy site 32A-32C. For example, the surgeon may place a 3.0-3.25 mm implant (not shown) into the first osteotomy site 32A, a 5.0 mm implant (not shown) into the second osteotomy site 32B, and a 6.0 mm implant (not shown) in the third osteotomy site 32C.

A surgeon may thus concurrently prepare a plurality of osteotomy sites 32A, 32B, 32C . . . 32n coupled with the ability to expand one site by compacting and another site by cutting without removing the osteotome 36 from the drill motor 38. The rotary osteotome 36 is thus configured to be turned at high speed in one direction to enlarge an osteotomy by compacting and in an opposite rotary direction to enlarge a different osteotomy by cutting.

Turning now to FIG. 6, an osteotome 36 according to an earlier embodiment of this invention is shown including a shank 40 and a body 42. The shank 40 has an elongated cylindrical shaft that establishes a longitudinal axis of rotation A for the rotary osteotome 36. A drill motor engaging interface 44 is formed at the distal upper end of the shaft for connection to the drill motor 38. The particular configuration of the interface 44 may vary depending on the type of drill motor 38 used, and in some cases may even be merely a smooth portion of the shaft against which the jaws of a collet may grip. The body 42 joins to the lower end of the shank 40, which joint may be formed with a tapered or domed transition 46. The transition 46 acts something like an umbrella as the surgeon irrigates with water during a procedure. The gentle transition 46 facilitates the flow of irrigating fluid onto the osteotomy site while the osteotome 36 is spinning.

The body 42 preferably has conically tapered profile decreasing from a maximum diameter adjacent the shank 40 and transition 46 to a minimum diameter adjacent an apical end 48. However, in some contemplated embodiments the body may be non-tapered (i.e., cylindrical). The apical end 48 is thus remote from the shank 40. The working length or effective length of the body 42 is proportionally related to its taper angle and to the size and number of osteotomes (36A, 36B, 36C, 36D . . . 36n) in a kit. Preferably, all osteotomes 36 in a kit will have the same taper angle, or approximately the same taper angle, and preferably the diameter at the upper end of the body 42 for one osteotome (e.g., 36A) is approximately equal to the diameter adjacent the apical end of the body 42 for the next larger size osteotome (e.g., 36B). Taper angles between about 1° and 5° (or more) are possible depending upon the application. More preferably taper angles between about 2°-3° will provide satisfactory results. And still more preferably, a taper angle of about 2° 36' is known to provide outstanding results for dental applications when the body 42 length is between about 1 1mm and 15 mm.

Figure 14:
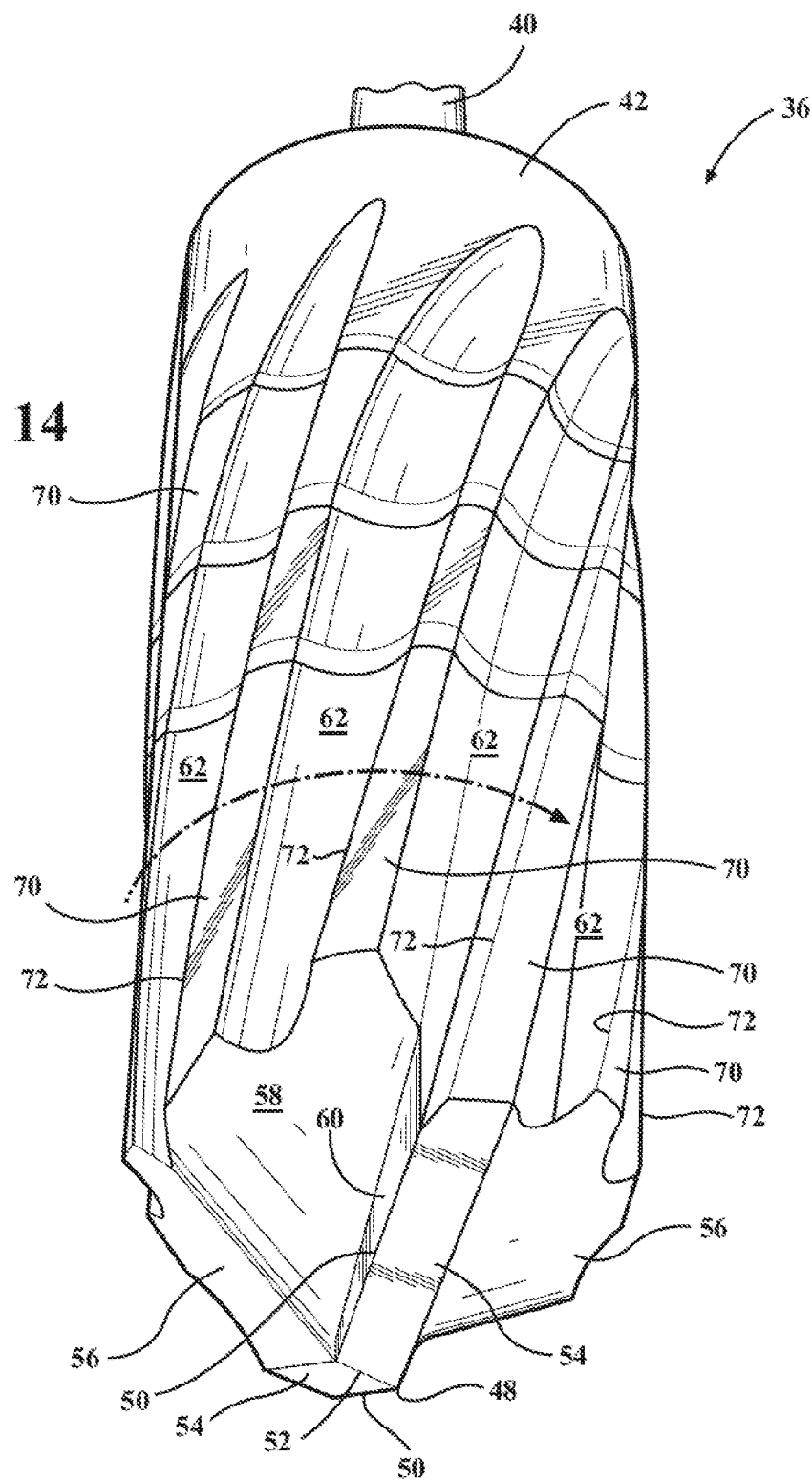
FIG. 14 is a fragmentary perspective view of the apical end of a rotary osteotome according to one embodiment of this invention.
Figure 15:
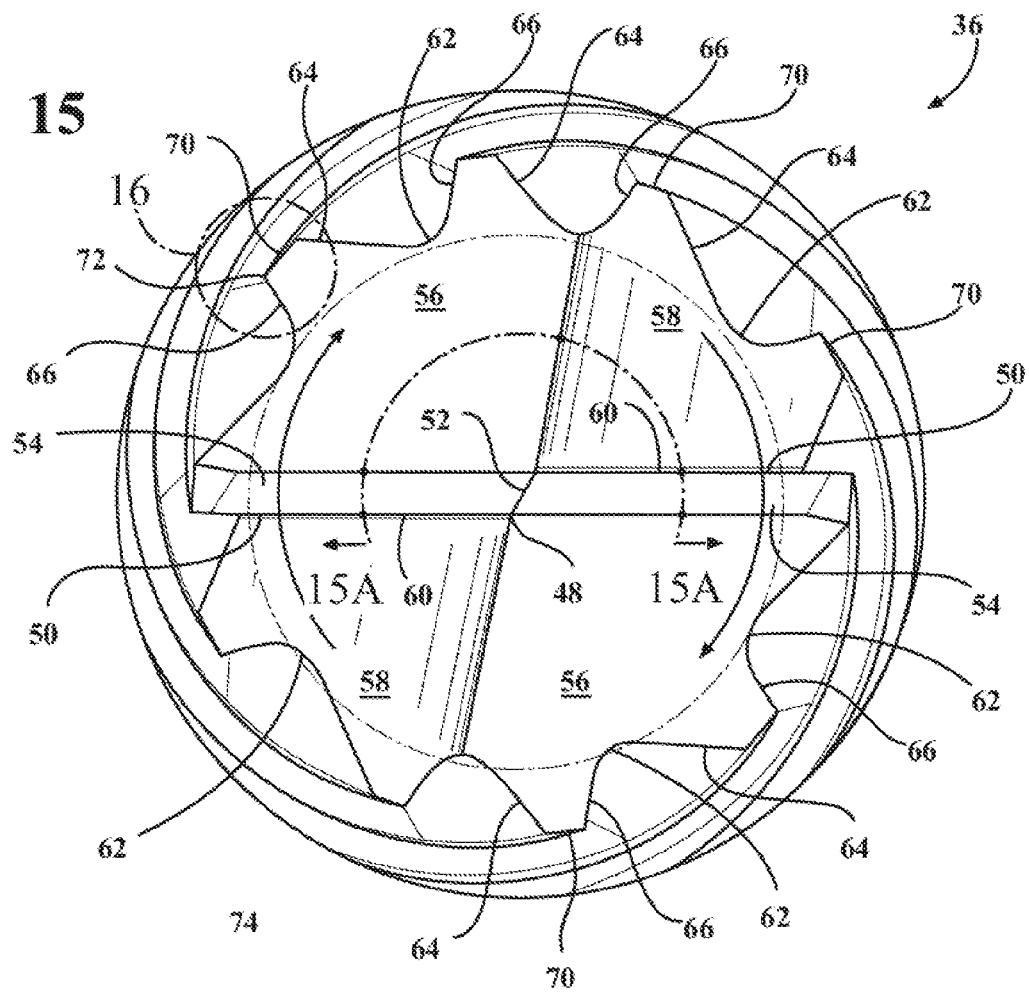
FIG. 15 is an end view of the apical end of a rotary osteotome of FIGS. 6, 10 and 14.

The apical end 48 is defined by at least one, but preferably a pair of lips 50. The lips 50 are in fact edges that are disposed on opposite sides of the apical end 48, but in the illustrated embodiment do not lie within a common plane. In other words, as shown in FIGS. 14 and 15, the lips 50 may be slightly offset (in terms of a direct diametrical alignment) by the short length of a chisel point 52 extending centrally through the longitudinal axis A. The chisel point 52 is a common feature found in drilling tools, but alternative apical end 48 formations to the chisel point 52 are of course possible, including rounded and simple pointed shapes, etc. As mentioned, the lips 50 are edges that angle upwardly and outwardly (radially) from the apical end 48. The angle of the lips 50 may be varied to optimize performance for the application. Lip 50 angles relative to the longitudinal axis A may range between about 30° (very pointed) and 75° (very blunt). In the illustrated examples, the lip angle is approximately 60° measured relative to longitudinal axis A, or 120° measured between the two opposing lips 50.

Each lip 50 has a generally planar first trailing flank 54. The first trailing flanks 54 are canted from their respective lips 50 at a first angle. The first angle may be varied between about 30° and 60° to optimize performance for the application. In practice, the first angle may be approximately 45° measured relative to longitudinal axis A (shown coinciding with lip face 60 in the semi-circular cross-sectional view of FIG. 15A). It will be appreciated therefore that the two opposing first trailing flanks 54 are set in opposite directions so that when the osteotome 36 is rotated in use, the first trailing flanks 54 either lead or follow their respective lips 50. When first trailing flanks 54 lead their respective lips 50, the osteotome is said to be turning in a non-cutting direction for the densifying mode; and conversely when the first trailing flanks 54 follow their respective lips 50, the osteotome is said to be turning in a cutting direction where the lips 50 cut or slice bone on descent. Or said another way, the cutting direction can be defined as rotationally sweeping the cutting faces 66 into the bone (or host material in non-medical applications). In the densifying direction, the first trailing flanks 54 form, in effect, a large negative rake angle for the lips 50 to minimize chip formation and shear deformation in the bone (or other host material) at the point of contact with the lips 50. (See for example FIGS. 17 and 20.)

Figure 10:
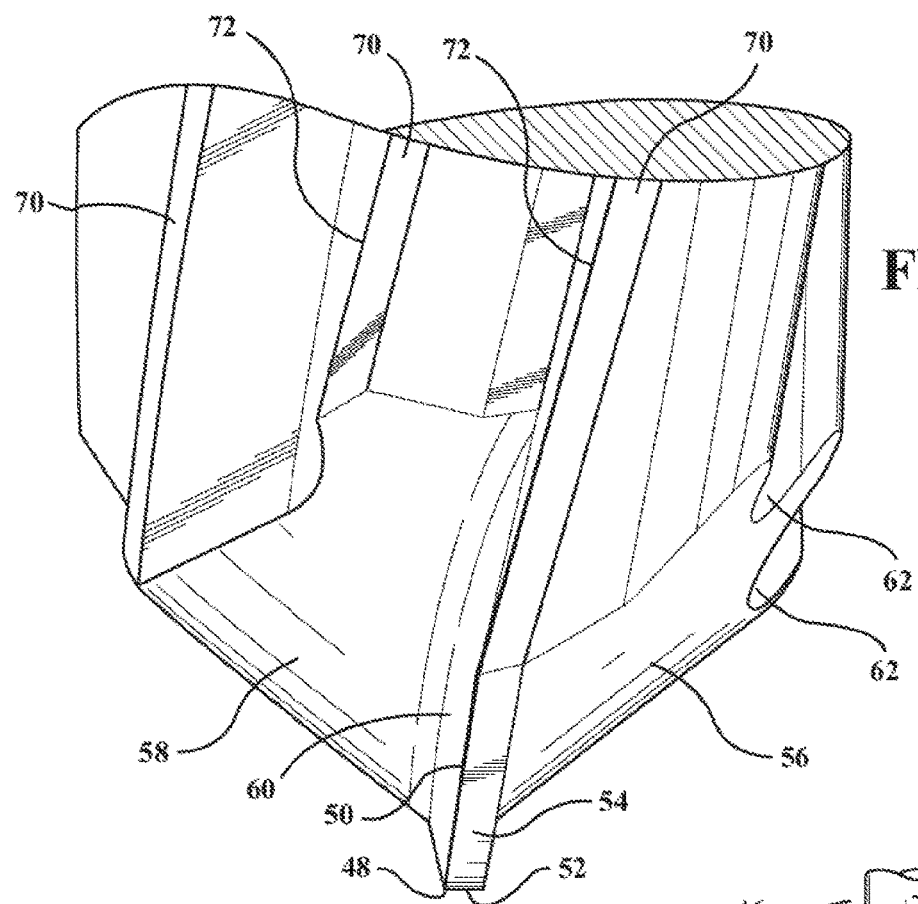
FIG. 10 is an enlarged view of the apical end of a rotary osteotome according to one embodiment of this invention.

A generally planar second trailing flank 56 is formed adjacent to, and falls away from, each first trailing flank 54 at a second angle. The second angle is smaller than the first angle, preferably less than about 55°. In an example where the first trailing flanks 54 are formed at 45° (relative to the axis A), the second trailing flanks 56 may be 40° or less. A generally planar relief pocket 58 is formed adjacent to, and falls away from, each second trailing flank 56 at a third angle. The third angle is smaller than the second angle. In an example where the second trailing flanks 56 are formed at 40° (relative to the axis A), the relief pockets 58 (i.e., the third angle) may be 30° or less. Each relief pocket 58 is disposed in a sector of the apical end 48 between a second trailing flank 56 and a lip 50. A generally axially disposed lip face 60 extends between the relief pocket 58 and the adjacent lip 50. This is perhaps best shown in the enlarged view of FIG. 10. When the osteotome 36 is rotated in the cutting direction, a significant amount of bone chips collect in the relief pocket 58 regions. When the osteotome 36 is rotated in the densifying direction, little to no bone chips collect in the relief pocket 58 regions.

Figure 15A:
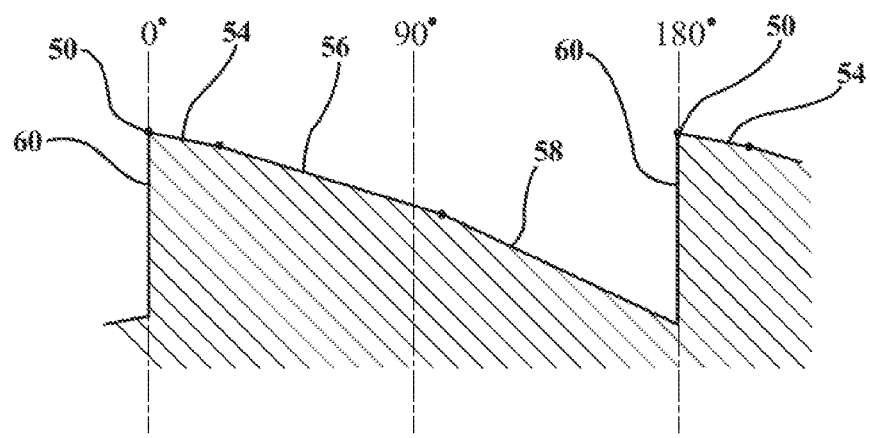
FIG. 15A is a cross-section of the apical end of an osteotome according to this invention taken generally along the semi-circular lines 15A-15A in FIG. 15.

FIG. 15A is a highly simplified and exemplary semi-circular cross-section through the apical end 48 of the osteotome 36, as taken along lines 15A-15A in FIG. 15. In this simplified illustration, small points are placed at the intersection of planar surfaces 54, 56 and 58. The node-like points do not exist in reality, but are added in this view to help distinguish boundaries of the different surfaces (54, 56, 58, 60). In combination with the several other views and descriptions, FIG. 15A will help inform the skilled artisan as to the various facets (54, 56, 58, 60) and their relationships to one another and to the lips 50.

A plurality of grooves or flutes 62 are disposed about the body 42. The flutes 62 may or may not have common axial length and radial depths. I.e., it is possible that the flutes 62 could, in some configurations, not all be identical. The flutes 62 are preferably, but not necessarily, equally circumferentially arranged about the body 42. The diameter of the body 42 may influence the number of flutes 62. As an example, bodies 42 in the range of about 1.5-2.8 mm may be formed with three or four flutes; bodies 42 in the range of about 2.5-3.8 mm may be formed with five or six flutes; bodies 42 in the range of about 3.5-4.8 mm may be formed with seven or eight flutes; and bodies 42 in the range of about 4.5-5.8 mm may be formed with nine or ten flutes. And so on. Of course, number of flutes 62 may be varied more or less than the examples given here in order to optimize performance and/or to better suit the particular application.

In the illustrated embodiment, the flutes 62 are formed with a helical twist. If the cutting direction is in the right-hand (clockwise) direction, then preferably the helical spiral is also in the right-hand direction. This RHS-RHC configuration is shown throughout the Figures, although it should be appreciated that a reversal of cutting direction and helical spiral direction (i.e., to LHS-LHC) could be made if desired with substantially equal results. The diameter of the body 42 may influence the angle of the helical spiral. Typically, spirals between about 5° and 20° are possible for the body 42 diameters between about 1.2 mm and 6 mm. As an example, bodies 42 in the range of about 1.5-2.8 mm may be formed with a 9.5° spiral; bodies 42 in the range of about 2.5-3.8 mm may be formed with an 11° spiral; bodies 42 in the range of about 3.5-4.8 mm may be formed with a 12° spiral; and bodies 42 in the range of about 4.5-5.8 mm may be formed with a 12.5° spiral. Of course, the spiral angles may be varied more or less than the examples given here in order to optimize performance and/or to better suit the particular application. Indeed, any diameter body 42 between about 1.2 mm and 6 mm may be formed with a helical spiral in the general range of about 5° to 20°.

Figure 16:
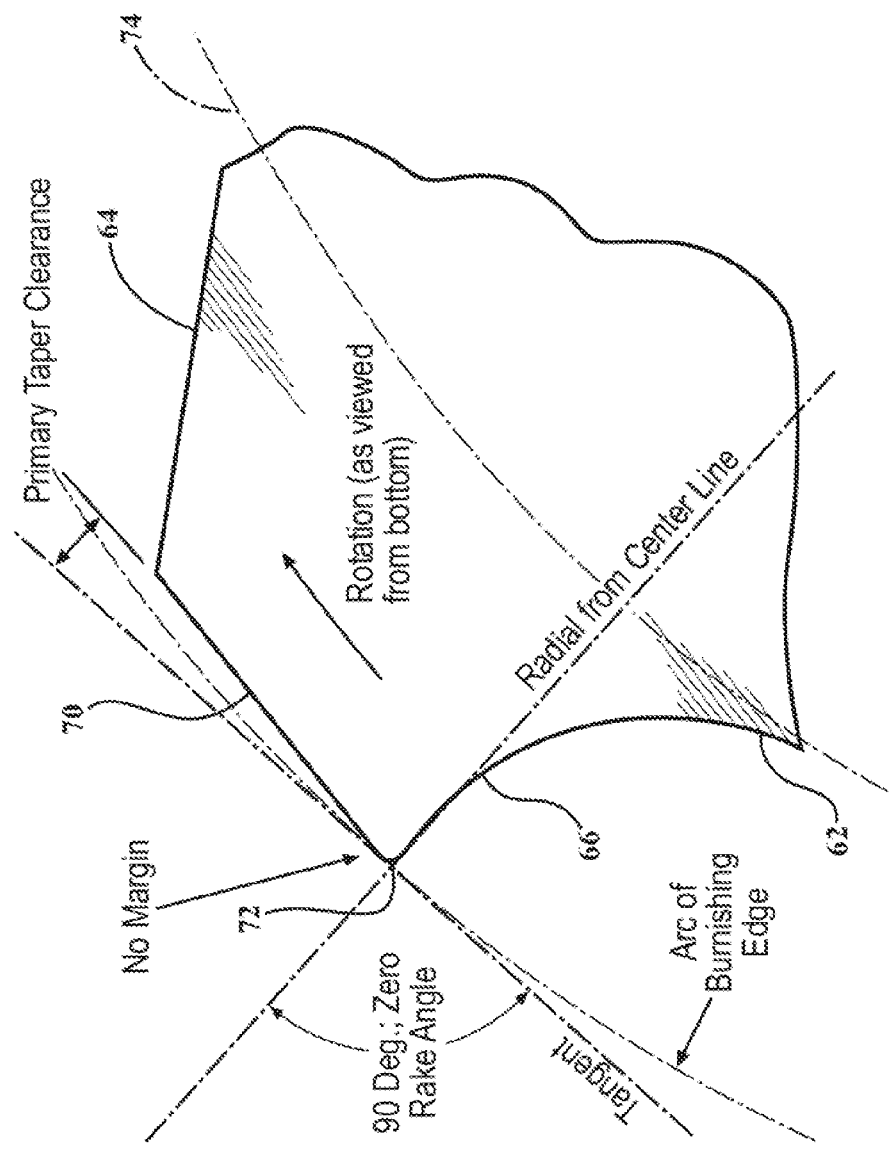
FIG. 16 is an enlarged view of a land as circumscribed at 16 in FIG. 15.
Figure 35:
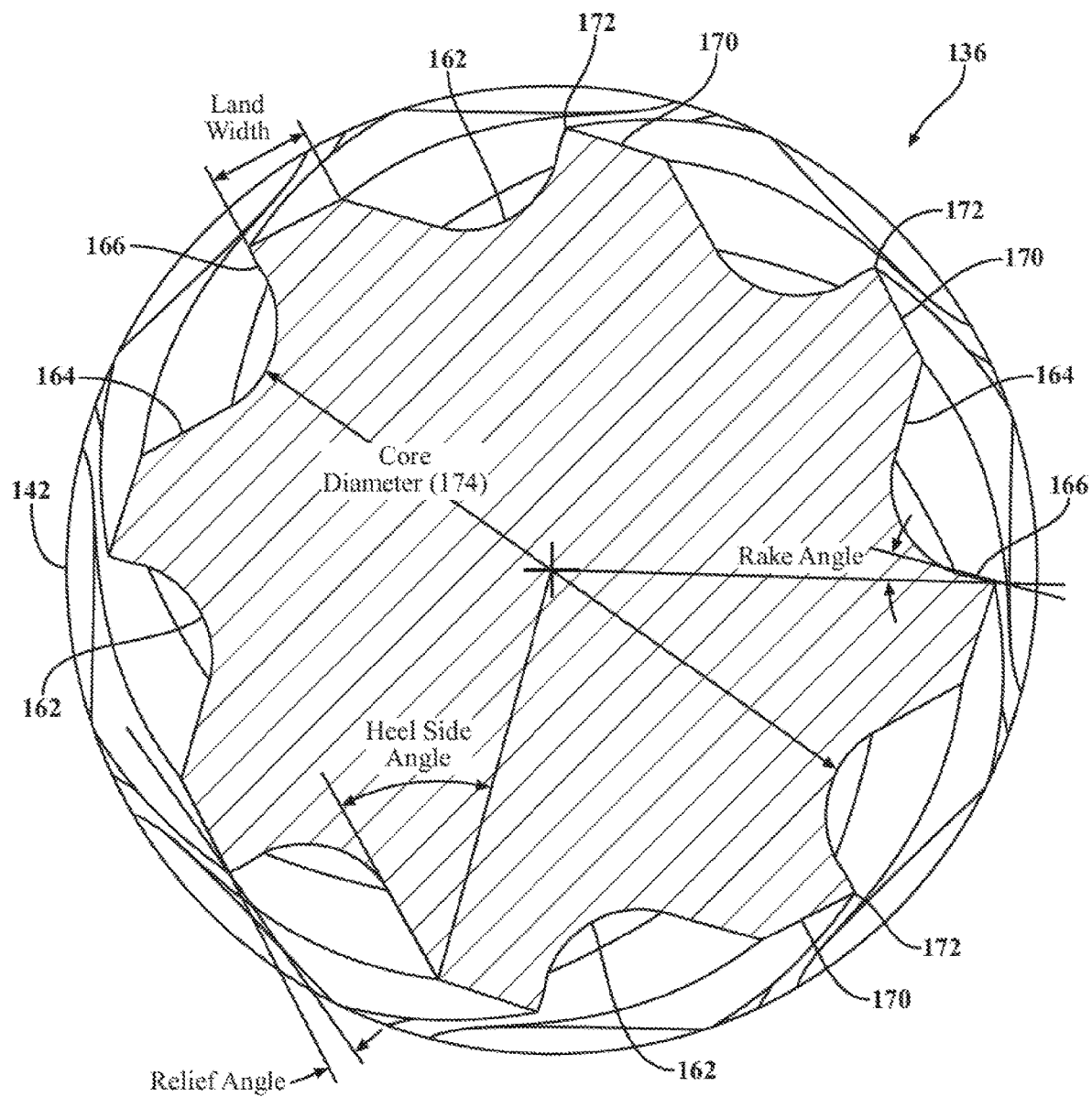
FIG. 35 is a cross-sectional view of the enhanced rotary osteotome as taken generally along lines 35-35 in FIG. 33.

As perhaps best shown in FIGS. 15 and 16, each flute 62 has a densifying face 64 and an opposing cutting face 66. A rib or land is formed between adjacent flutes 62, in alternating fashion. Thus, a four-flute 62 osteotome 36 will have four lands, a ten-flute 62 osteotome 36 will have ten interleaved lands, and so forth. Each land has an outer land face 70 that extends (circumferentially) between the densifying face 64 of the flute 62 on one side and the cutting face 66 of the flute 62 on its other side. The sharp interface between each land face 70 and its associated cutting face 66 is referred to as a working edge 72. Depending on the rotational direction of the osteotome 36, the working edge 72 either functions to cut bone or compact bone. That is, when the osteotome is rotated in the cutting direction, the working edges 72 slice and excavate bone (or other host material). When the osteotome is rotated in the densifying (non-cutting) direction, the working edges 72 compress and radially displace bone (or other host material) with little to no cutting whatsoever. This compaction and radial displacement is exhibited as gentle pushing of the osseous structure laterally outwardly in a condensation mechanism. FIG. 15 depicts a core diameter 74 superimposed as a broken circle. FIG. 35 also labels the core diameter 74 as the shortest perpendicular distance between diametrically opposing flutes 62. The core diameter 74 is the root or central portion of the body 42 that joins all of the lands. The diameter of the core diameter 74 varies with the tapering diameter of the body 42.

The working edges 72 are shown throughout the illustrations as being substantially margin-less, in that the entire portion of each land face 70 is cut away behind the working edge 72 to provide complete clearance. In standard prior art burs and drills, margins are commonly incorporated behind the working edge to help guide the drill in the hole and maintain the drill diameter. Primary taper clearance angles, i.e., the angle between a tangent of the working edge 72 and each land face 70 as shown in FIG. 16, may fall anywhere between about 1° and 35° depending upon the application and, possibly, on the diameter of the body 42. Primary taper clearances between about 5° and 20° have been found effective for the body 42 diameters between about 1.2 mm and 6 mm. As an example, bodies 42 in the range of about 1.5-2.8 mm may have land faces 70 formed with a 15° primary taper clearance; bodies 42 in the range of about 2.5-3.8 mm may have land faces 70 formed with an 15° primary taper clearance; bodies 42 in the range of about 3.5-4.8 mm may have land faces 70 formed with a 12° primary taper clearance; and bodies 42 in the range of about 4.5-5.8 mm may have land faces 70 formed with a 10° primary taper clearance. Of course, the primary taper clearance angles may be varied more or less than the examples given here to optimize performance and/or to better suit the application. As mentioned above in connection with the angle of the helical twist, the substantially margin-less working edges 72 are shown, for example in FIG. 14, turning away from the densifying direction as the conically tapered profile of the body 42 decreases in diameter. In other words, when the densifying direction is counter-clockwise as shown in FIG. 14, the helical twist of the working edges 72 winds in the counter-clockwise direction when viewed from the top of the body 42 looking toward its apical end 48. Or conversely, as shown in FIG. 14 when viewed from the apical end 48 looking toward top of the body 42, the twist will appear to be in the clockwise direction. Thus, when the bone densifying direction is counter-clockwise, the working edges 72 will "turn away from the densifying direction" when all of the land faces 70 and flutes 62 orbit counter-clockwise about the longitudinal axis A as one traces each land face 70 and flute 62 downwardly toward the apical end 48.

The cutting face 66 establishes a rake angle for each respective working edge 72. A rake is an angle of slope measured from the leading face of the working edge 72 to an imaginary line extending perpendicular to the surface of the worked object (e.g., inner bone surface of the osteotomy). Rake angle is a parameter used in various cutting and machining processes, describing the angle of the cutting face relative to the work. Rake angles can be: positive, negative or zero. According to FIG. 16, the rake angle for working edge 72 when rotated in a cutting direction may be about zero degrees (0°). In other words, the cutting face 66 in the example of FIG. 16 is oriented approximately perpendicular to a tangent of the arc scribed through the working edge 72. As shown in FIG. 16, this establishes a crisp cutting edge 72 well-suited to cut/slice bone when the osteotome 36 is rotated in the cutting direction. However, it has been discovered that the cutting functionality of the rotary osteotome 36 can be improved by changing the rake angle of the cutting face 66 between about 0° and about −65° (negative rake) as a function of distance from the apical end 48. This optimization of the rake angle of the cutting face 66 is described in detail below in connection with FIGS. 33-47.

When the osteotome 36 is counter-rotated, in the densifying mode, the effective rake angle is established between the working edge 72 and the land face 70, which as previously stated may lie at a large negative rake angle in the order of about 55°-89°, which is the compliment of the primary taper clearance angle. The large negative rake angle of the working edge 72 (when rotated in a densifying direction) applies outward pressure at the point of contact between the wall of the osteotomy 32 and the working edge 72 to create a compression wave ahead of the point of contact, loosely akin to spreading butter on toast. Osseodensification may also be loosely compared to the well-known process of burnishing metal to improve metal surface quality.

Downward pressure applied by the surgeon is needed to keep the working edge 72 in contact with the bone surface of the osteotomy 32 being expanded. That is, pressure is needed to generate and propagate a compression wave in the bone that begins when the contact stresses exceed the yield strength of the host bone material. This is aided by the taper effect of the osteotomy 32 and tool 36 to create lateral pressure (i.e., in the intended direction of expansion). The harder the surgeon pushes the rotary osteotome 36 into the osteotomy 32, the more pressure is exerted laterally. This gives the surgeon complete control of the expansion rate irrespective to a large degree on the rotation speed of the osteotome 36, which is a factor underlying the short learning curve required to master the osseodensification technique. Thus, the compaction effect's intensity depends chiefly on the amount of force exerted on the osteotome 36, which is controlled by the surgeon. The more force exerted, the quicker expansion will occur.

As each working edge 72 drags across the bone, the applied forces can be decomposed into two components: one normal to the bone's surface, pressing it outwardly, and the other tangential, dragging it along the inner surface of the osteotomy 32. As the tangential component is increased, the working edge 72 will start to slide along the bone. At the same time, the normal force will deform the softer bone material. If the normal force is low, the working edges 72 will rub against the bone but not permanently alter its surface. The rubbing action will create friction and heat, but this can be controlled by the surgeon by altering, on-the-fly, the rotation speed and/or pressure and/or irrigation flow. Because the body 42 of the osteotome 36 is tapered, the surgeon may at any instant during the surgical procedure lift the working edges 72 away from contact with the surface of the bone to allow cooling. This can be done in a controlled "bouncing" fashion where pressure is applied in short bursts with the surgeon continuously monitoring progress and making fine corrections and adjustments. See FIGS. 7 and 8 which illustrate this variable application of force and the ability for the osteotome to be lifted out of engagement—at any time during a procedure—with the walls of the osteotomy 32. As the surgeon-applied downward force increases, eventually the stresses in the bone's surface exceed its yield strength. When this happens, the working edges 72 will plow through the surface and create a trough behind. See FIG. 32. The plowing action of the working edges 72 thus progressively enlarges the osteotomy until the rotary osteotome 36 reaches full/maximum depth, at which time a different larger rotary osteotome 36 must be used to achieve further expansion if desired.

Figure 9:
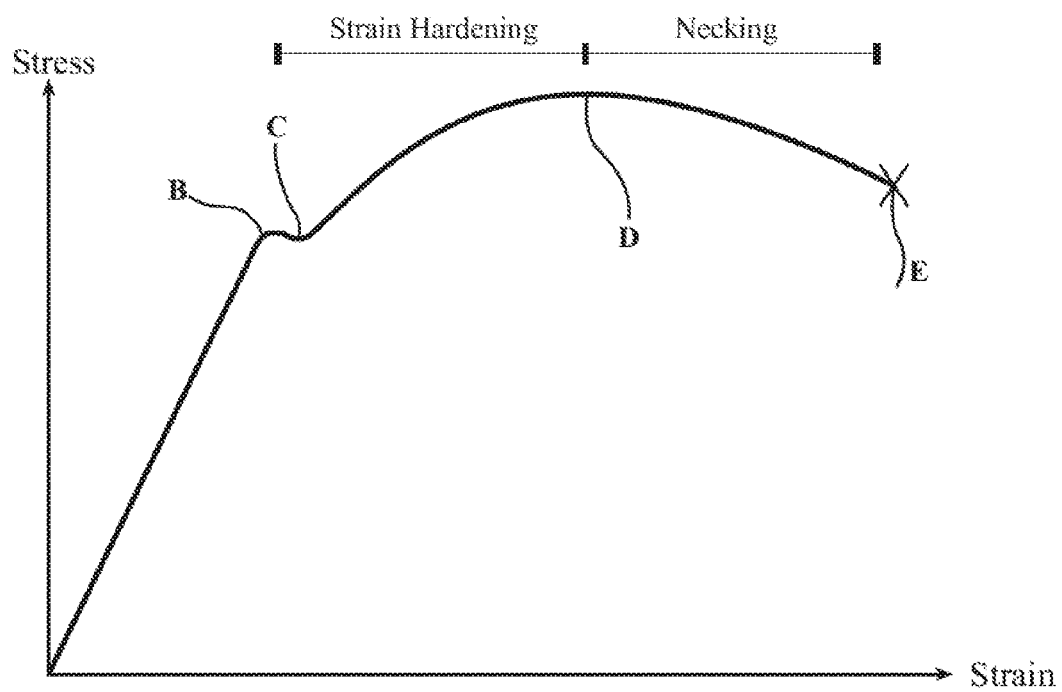
FIG. 9 is a simplified stress-strain curve generally representative of bone, metal foam and other host materials for with the present invention is suited for use.

FIG. 9 depicts a Stress-Strain curve that is generally illustrative for bone and other ductile materials including but not limited to foam metals and cellular polymers of the type used in various commercial, industrial and aerospace applications. The straight-line segment of the curve from the point of origin (0,0) to B represents the material's elastic response region. Reference point B indicates the elastic limit of the material. While the elastic properties of bone are well-known, if the load imposed by the surgeon does not exceed the bone's ability to deform elastically, i.e., beyond point B, the bone will promptly return to its initial (undeformed) condition once the stress is removed. On the other hand, if the load imposed by the surgeon exceeds the bone's ability to deform elastically, the bone will deform and change shape permanently by plastic deformation. In bone, the permanent change in shape may be associated with micro-cracks that allow energy release, a compromise that is a natural defense against complete fracture. If these micro-cracks are small, the bone remains in one piece while the osteotomy expands. The region of plastic deformation extends from the yield point of the material (C), all the way to the point of fracture (E). The peak (D) of the curve between yield point (C) and fracture (E) indicates the material's ultimate tensile strength. When a material (e.g., bone) is subjected to stress in the region between its yield point (C) and its ultimate tensile strength (D), the material experiences strain hardening. Strain hardening, also known as work hardening or cold working, is the strengthening of a ductile material by plastic deformation. This strengthening occurs because of dislocation movements and dislocation generation within the crystal structure of the material—which for bone materials corresponds with the dislocation of the cross-links between collagen fibers in the bone tissue. The material tends to experience necking when subjected to stress in the region between its ultimate tensile strength (D) and the point of fracture (E).

Figure 12:
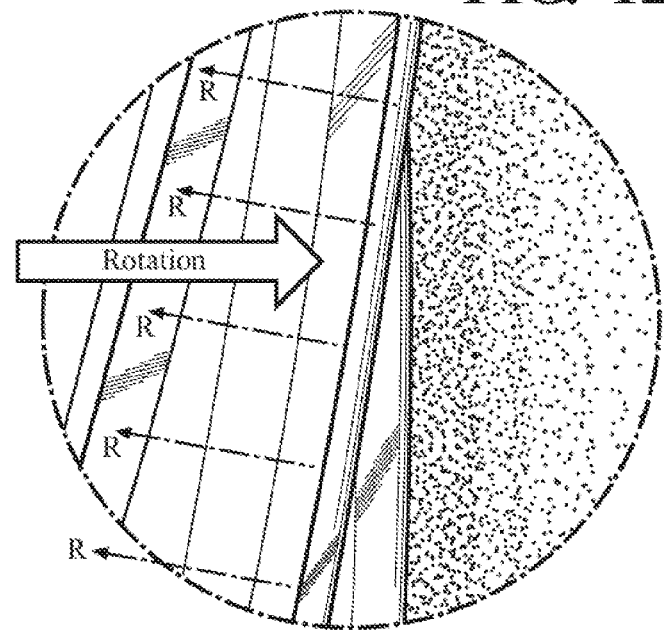
FIG. 12 is an enlarged view of the area circumscribed at 12 in FIG. 11 and enhanced with reaction forces (R) as applied by the walls of the bone to the rotary osteotome in response to rotation of the osteotome in the burnishing direction.
Figure 13:
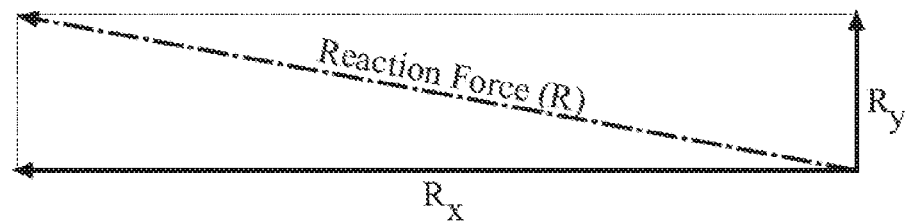
FIG. 13 is a diagram of the reaction forces (R) of FIG. 12, shown broken into component lateral ($R_x$) and axial ($R_y$) forces.
Figure 20:
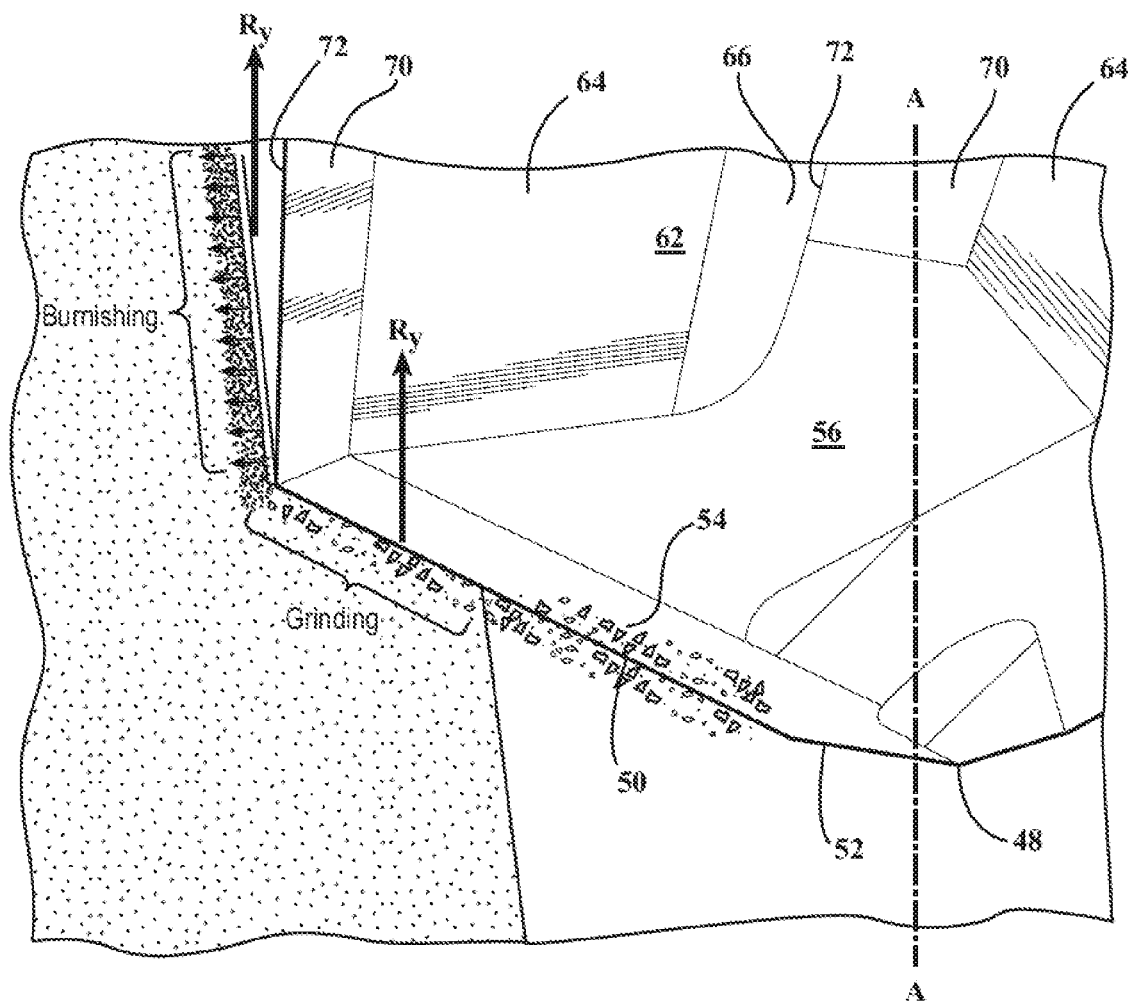
FIG. 20 is an enlarged view of the area circumscribed at 20 in FIG. 17 and depicting the bone grinding and auto-grafting features of the apical end.

The direction of helical twist can be designed to play a role in contributing to the surgeon's control so that an optimum level of stress (in the strain hardening zone between (C) and (D) on the graph of FIG. 9) can be applied to the bone (or other host material) throughout the expansion procedure. In particular, the RHS-RHC configuration described above, which represents a right-hand spiral for a right-hand cutting direction (or alternatively an LHS-LHC configuration, not shown) applies a stress that provokes a beneficial opposing axial reaction force (Ry) in the host bone when the osteotome 36 is continuously rotated at high speed in a densifying direction and concurrently forcibly advanced (manually by the surgeon) into an osteotomy 32. This opposing axial reaction force (Ry) is illustrated graphically in FIGS. 11-13 as being directionally opposite to the forcibly advanced direction into the osteotomy 32. In other words, if the surgeon operating the osteotome 36 is pushing the osteotome 36 downwardly into an osteotomy 32, then the opposing axial reaction force (Ry) works in the opposite direction to push the osteotome upwardly. The opposing axial reaction force (Ry) is the vertical (or perhaps more accurately the "axial" vis-à-vis the longitudinal axis A) component of the reaction force (R) that is the Newtonian "equal and opposite reaction force" applied by the bone against the full length of the working edges 72 of the osteotome 36 (i.e., Newton's Third Law of Motion). An opposing axial reaction force (Ry) is also created by the effectively large negative rake angle at the lips 50 when the osteotome 36 is rotated in a densifying direction, as shown in FIG. 20 and easily perceived from FIG. 15A. Those of skill in the art will appreciate alternative embodiments in which the opposing axial reaction force (Ry) is created by either the configuration of the lips 50 alone or of the working edges 72 alone rather than by both (50, 72) acting in concert as in the preferred embodiment.

For a surgeon to advance the apical end 48 toward the bottom of the osteotomy 32 when the osteotome 36 is spinning in the densifying direction, he or she must push against and overcome the opposing axial reaction forces (Ry) in addition to supplying the force needed to plastically displace/expand the bone as described above. The osteotome 36 is designed so that the surgeon must continually work, as it were, against the opposing axial reaction forces (Ry) to expand the osteotomy 32 by compaction, i.e., when in the densifying mode. Rather than being a detriment, the opposing axial reaction forces (Ry) are a benefit to the surgeon by giving them greater control over the expansion process. Because of the opposing axial reaction forces (Ry), the osteotome 36 will not be pulled deeper into the osteotomy 32 as might occur with a standard "up cutting" twist drill or burr that is designed to generate a tractive force that tends to advance the osteotome toward the interior of the osseous site. Up-cutting burrs have the potential to grab and pull the burr more deeply into the osteotomy, which could lead to inadvertent over-penetration.

In the densifying mode, the intensity of the opposing axial reaction forces (Ry) is always proportional to the intensity of force applied by the surgeon in advancing the body 42 into the osteotomy 32. This opposing force thus creates real-time haptic feedback that is intuitive and natural to inform the surgeon whether more or less applied force is needed at any given instant. This concurrent tactile feedback takes full advantage of the surgeon's delicate sense of touch by applying reaction forces (R, and in particular the axial component Ry) directly through the osteotome 36. In this densifying mode, the mechanical stimulation of the opposing axial reaction forces (Ry) assists the surgeon to better control the expansion procedure on the basis of how the bone (or other host material) is reacting to the expansion procedure in real time.

Thus, the controlled "bouncing" or "pumping" action described above in connection with FIGS. 7-9 is made more effective and substantially more controllable by the opposing axial reaction forces (Ry) so that the surgeon can instinctively monitor progress and make fine corrections and applied pressure adjustments on-the-fly without losing control over the rate of expansion. The tactile feedback from the opposing axial reaction forces (Ry) allows a surgeon to intuitively exert stress on the bone material so that its strain response preferably resides in the strain hardening zone, that is, between its yield point (C) to its ultimate tensile strength (D). In any event, the surgeon will endeavor to maintain the stress (as generated by the force he or she applies through the rotating osteotome 36) above the elastic limit (B) and below the point of fracture (E). Of course, until the applied stress passes the elastic limit (B), the bone will not permanently deform at all; and to apply stress beyond the point of fracture (E) will cause the bone (or other host material) to break—possibly catastrophically.

Figure 8:
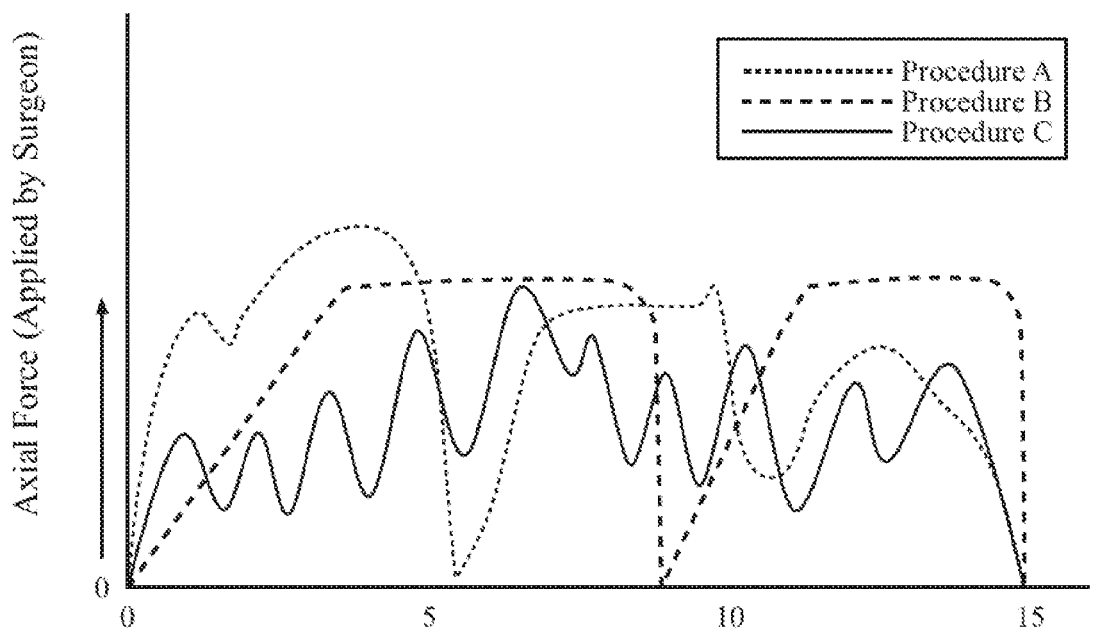
FIG. 8 is an exemplary graph plotting the force applied by a user to advance the body into an osteotomy against the depth of penetration into the osteotomy (or hole) in three separate procedures in order to illustrate that the surgeon (or user) can make on-the-fly adjustments to the advancing force depending on particular situation.

The exemplary graph in FIG. 8 plots the force applied by a surgeon to advance the body 42 into an osteotomy 32 against its depth of penetration into the osteotomy 32 in three separate procedures (A-B-C) to graphically show how the surgeon can make these on-the-fly adjustments depending on particular situation they encounter. The applied force is, as mentioned above, the force manually generated by the surgeon and needed to overcome the combined opposing axial reaction forces (Ry) plus the forces needed to expand/deform the bone. The applied force creates stress in the bone (or other host material), so that it develops a strain response like that shown in FIG. 9. During an operation, the surgeon uses his or her skill to manually vary the applied stress so that the strain response remains within the plastic deformation region (B-E), and more preferably still within the more ideal strain hardening region (C-D). The configuration of the osteotome 36, therefore, is designed to give a surgeon more control during an expansion (densifying mode) procedure by generating proportional, opposing axial reaction forces (Ry) when the osteotome 36 continuously rotated and concurrently forcibly advanced into an osteotomy 32.

Figure 17:
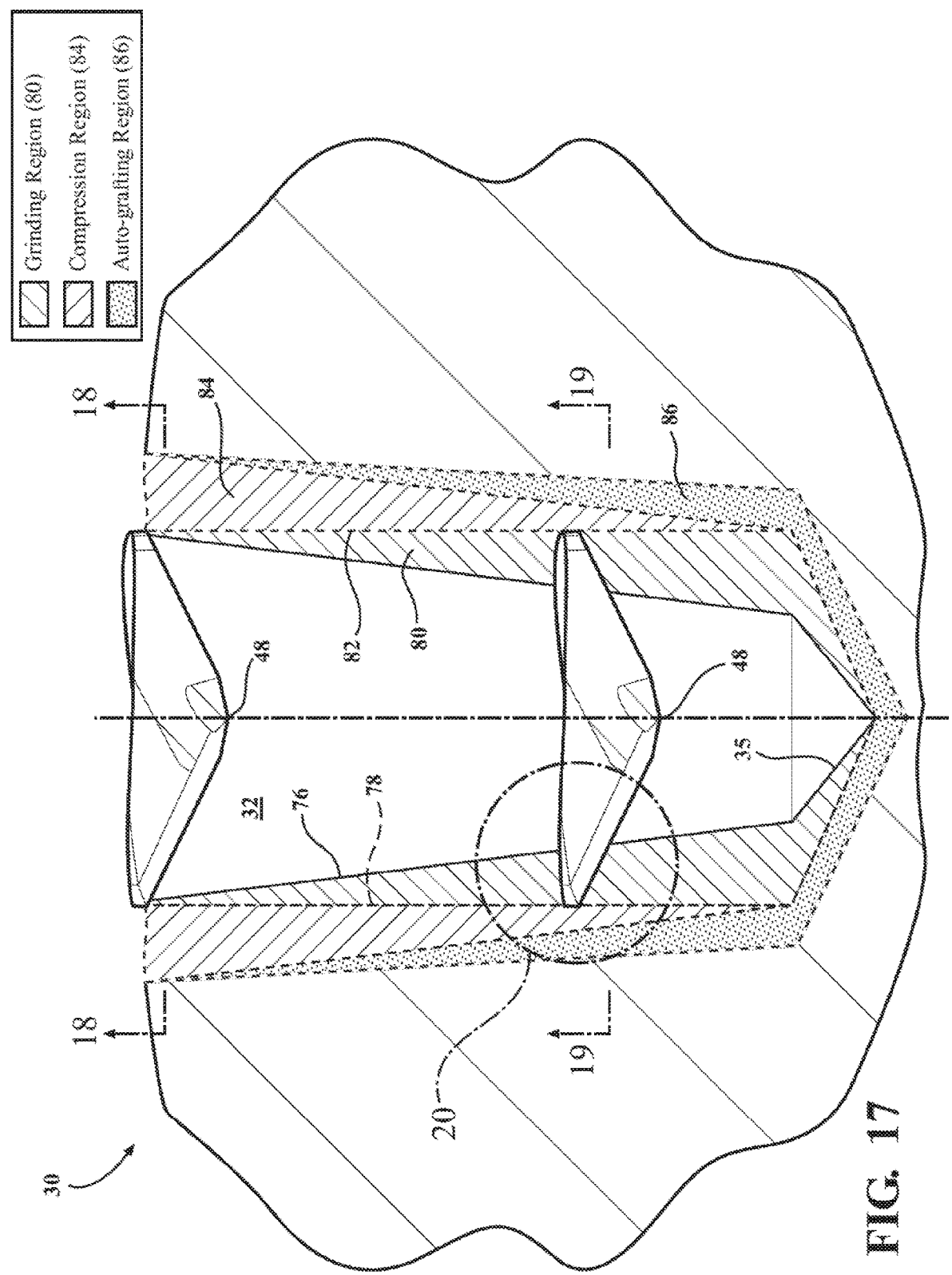
FIG. 17 is an exaggerated cross-section through an osteotomy with the apical end of a rotary osteotome shown at various stages of the expansion procedure in order to describe the zones of an osteotomy that experience grinding, compaction and auto-grafting with each stage of the expansion process.
Figure 18:
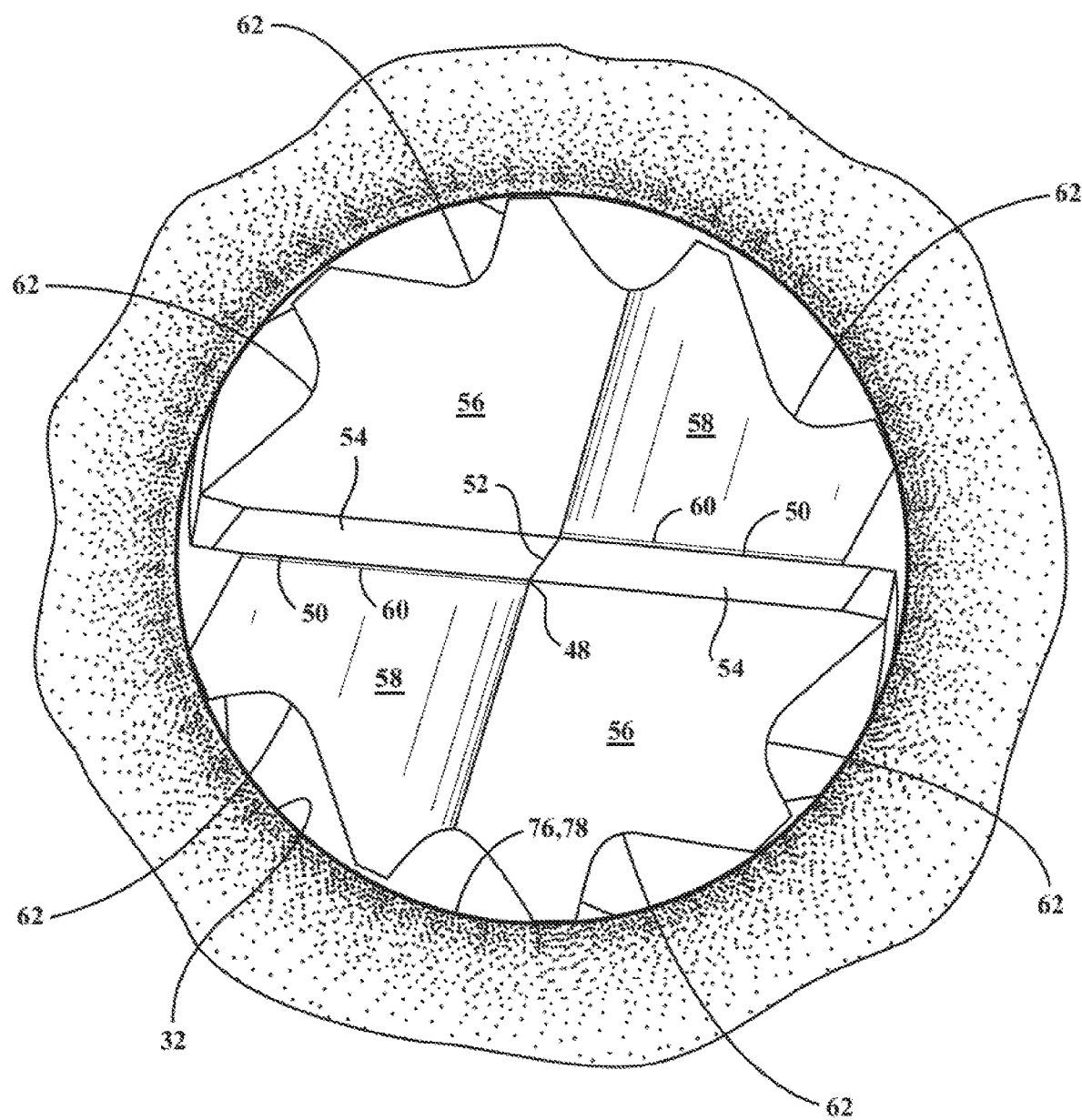
FIG. 18 is a cross-sectional view taken generally along lines 18-18 in FIG. 17.
Figure 19:
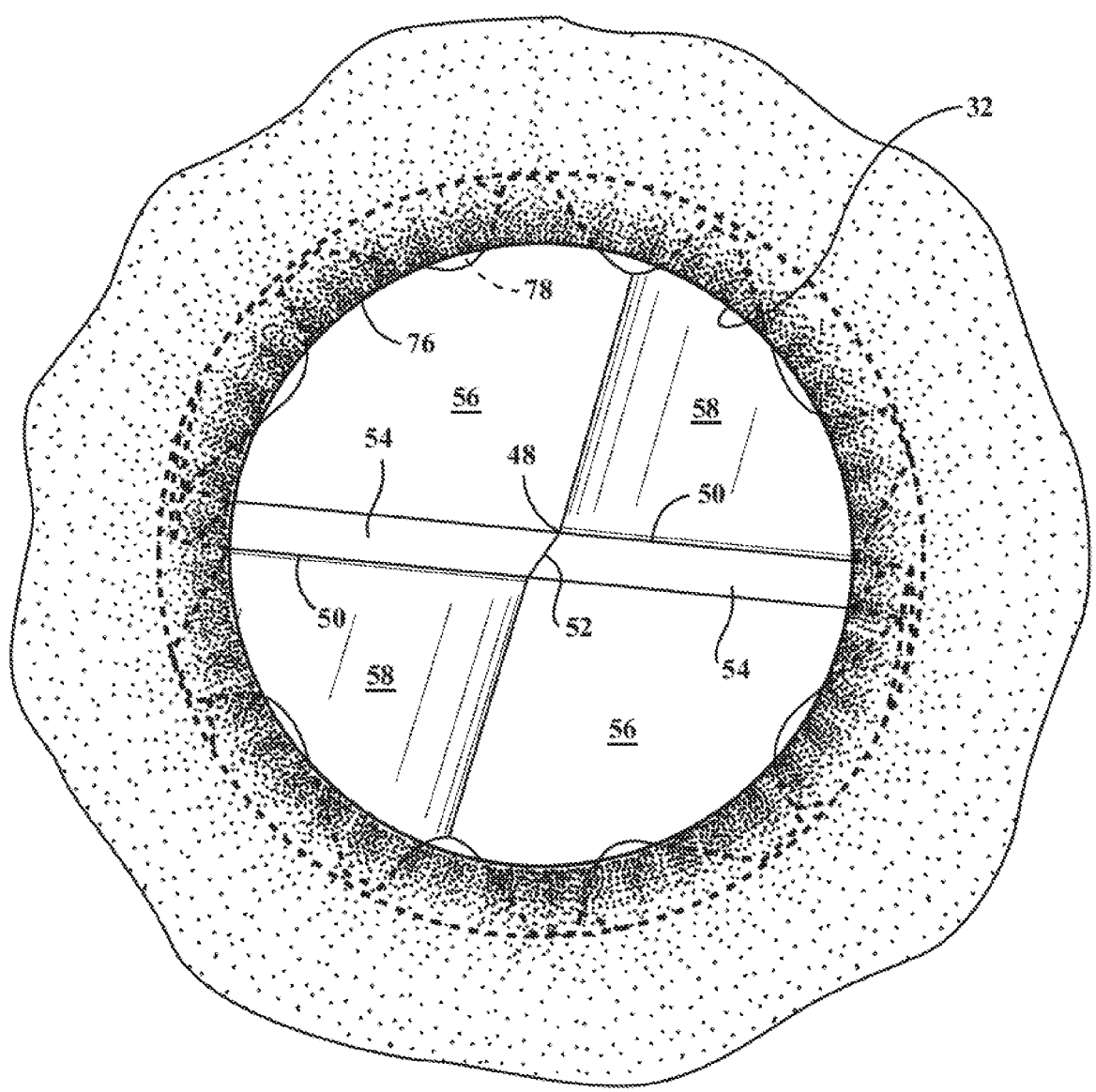
FIG. 19 is a cross-sectional view taken generally along lines 19-19 in FIG. 17.

FIGS. 17-21 illustrate the ability of the rotary osteotome 36 to simultaneously auto-graft and compact bone. The compaction aspect may be defined as the gentle push of osseous structure laterally outwardly to compact the cells throughout the region surrounding the osteotomy 32. In FIG. 17, an osteotomy 32 formed by the present invention is shown with exaggerated taper on the order of ~7° (as compared with the preferred taper angle in the range of about 2°-3°) to highlight the necessary grinding of a small amount of bone (or other host material) with each progressively larger osteotome 36.

In FIG. 17, surface 76 indicates the inner wall of the osteotomy 32 as prepared in a preceding expansion operation by an osteotome 36 of smaller size. That is to say, in this example the surface 76 represents a precursor hole. The apical end 48 of the next incrementally larger size osteotome 36 is shown in solid about to enter the osteotomy and again approximately ⅔ into the osteotomy 32. It is to be understood that the osteotome 36 is continuously rotated at high speed in a densifying direction (e.g., counter-clockwise) and concurrently forcibly advanced into an osteotomy 32 by the surgeon's manual efforts. Construction line 78 indicates the cylindrical (i.e., non-tapering) path of the apical end 48 as it moves from top to bottom within the osteotomy 32. In other words, the diameter of the apical end 48 remains the same, and therefore the diameter of its path 78 also remains constant over the distance it travels. When the osteotome 36 first enters the osteotomy 32 as shown in solid, the internal diameter of the prior osteotomy 76 is approximately equal to the diameter of the apical end 48. However, the internal diameter of the prior osteotomy 76 progressively narrows (i.e., tapers inwardly) toward the bottom 35 of the osteotomy 32. Yet as shown the cylindrical path of the apical end 48 remains constant. Therefore, as the osteotome 36 is advanced deeper toward the bottom 35 of the osteotomy 32, more and more bone is ground away and/or displaced to make room for the advancing (larger) osteotome 36. Region 80, defined as the annular space between surfaces 76 and 78 (plus a portion of the apical end 48), represents the bone material that is milled and/or displaced by the outermost edges of the lips 50 as the apical end 48 makes its way to the full depth of the osteotomy 32. The milled or ground region 80 includes not only the side walls, but also the apical end 48 of the osteotomy 32. As a reminder, the taper angle is shown substantially exaggerated in FIG. 17, such that the grinding region 80 appears much larger than would be the case with a smaller taper angle of about 2°-3°. In a subsequent operation (not shown), when another osteotome 36 of the next larger size is used to further expand the osteotomy 32, a similar (but larger) region 80 will exist as its apical end 48 is pushed to the bottom 35 of the osteotomy 32, and so on.

Remaining within the context of FIG. 17, surface 82 indicates the outer wall of the osteotomy 32 as prepared by the expansion operation of osteotome 36 when its apical end 48 reaches the bottom 35. The surface 82 is a substantially perfect negative of the revolving osteotome body 42. In other words, the surface 82 will have a taper equal to that of the osteotome body 42, and a bottom impression made by the spinning apical end 48 of the osteotome illustrated. Region 84, defined as the annular space between surfaces 78 and 82, represents the bone material that is plastically displaced by the working edges 72 of the lands as the osteotome body 42 makes its way to the full depth of the osteotomy 32. All of the bone material within region 84 is compacted radially outwardly into the surrounding bone structure without cutting, and therefore represents a zone of densified bone.

An important observation may be stated as: "What happens to the ground/milled bone material that once occupied region 80?". As alluded to previously, the osteotome 36 is configured to simultaneously auto-graft and compact the ground/milled bone from region 80 as it is rotated and forcibly advanced into the osteotomy 32. The auto-grafting phenomena supplements the basic bone compaction and condensation effects described above to further densify the inner walls 82 of the osteotomy. Furthermore, auto-grafting—which is the process of repatriating the patient's own bone material—enhances natural healing properties in the human body to accelerate recovery and improve osseointegration.

Figure 21:
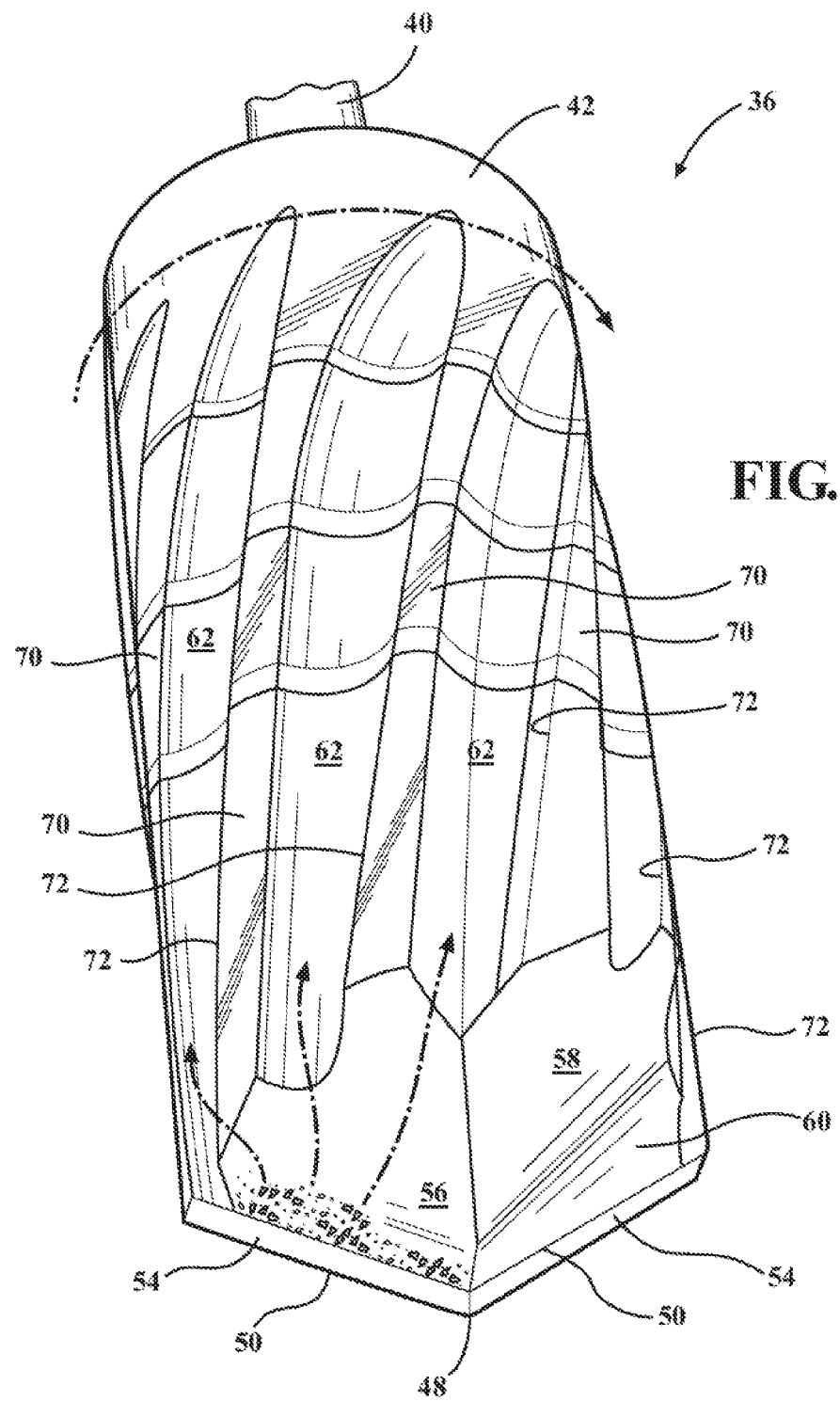
FIG. 21 is a fragmentary perspective view of the apical end as in FIG. 14 but from a slightly different perspective and illustrating the region of the apical end where bone material collects and is subsequently repatriated into surrounding bone.

Turning to FIG. 20, an enlarged view is shown of the interface between the apical end 48 and the host bone material as taken from the circumscribed area in FIG. 17. At the point where the outermost edge of each rotating and forcibly advancing lip 50 contacts the bone, attrition causes the bone to be ground away. The bone debris collects mainly on the second trailing flanks 56, i.e., immediately behind the respective first trailing flanks 54. Some of the accumulated bone debris migrates radially inwardly along the lips 50 and is carried all the way to the very bottom of the osteotomy 32. The remainder of the accumulated bone debris is distributed along the flutes 62 which directly intersect the second trailing flanks 56 by the pressure exerted through the surgeon's manual pushing efforts. This is illustrated in FIG. 21. Observe that a plurality of flutes 62 open into the second trailing flanks 56. (See also FIG. 43 in which a plurality of flutes 162 are clearly shown meeting with each second trailing flank 156 for receiving an up-flow of boney slurry in densifying mode.) In the smallest diameter osteotomes 36, perhaps only two flutes 62 will intersect the second trailing flanks 56. However, as osteotome 36 diameter increases, the opportunity for three or more flutes 62 to accept outflow of bone particles directly from the second trailing flanks 56 becomes quite practical. These flutes 62 readily carry bone debris away from the grinding interface, thereby reducing the possibility of heat- and/or pressure-induced necrosis in the bone particles. Despite the abundant outflow capacity enabled by the plurality of flutes 62 opening into the second trailing flanks 56, it is possible that a small fraction of bone debris could spill over into the relief pockets 58, but this is of minimal significance.

Bone debris that is distributed up the flutes 62 works its way toward the associated land faces 70 where it is wiped and pressed into the cellular walls of the osteotomy 32 and immediately grafted back into the patient's bone very near to the sight were it was harvested. Bone debris that is carried to the bottom of the osteotomy 32 is wiped and pressed into the bottom of the osteotomy 32. As a result, an auto-grafting zone 86 is developed around and under the compaction region 84, as shown in FIG. 17. Interestingly, the auto-grafting zone 86 is thinnest where the compaction zone 84 is thickest, and conversely the auto-grafting zone 86 is thickest where the compaction zone 84 is thinnest. And at the osteotomy bottom 35 where this is little-to-no compaction at all, there is a significant zone of auto-grafting 86 which serves to densify (and positively stimulate) an area of the osteotomy 32 which could otherwise not be densified. This is confirmed in the micro-CT image of FIG. 22, far-right osteotomy. It can therefore be appreciated that the auto-grafting phenomena is an ideal complement to the basic bone compaction and condensation effects in preparing an osteotomy 32 to receive an implant 34 or other fixation device.

Figure 22:
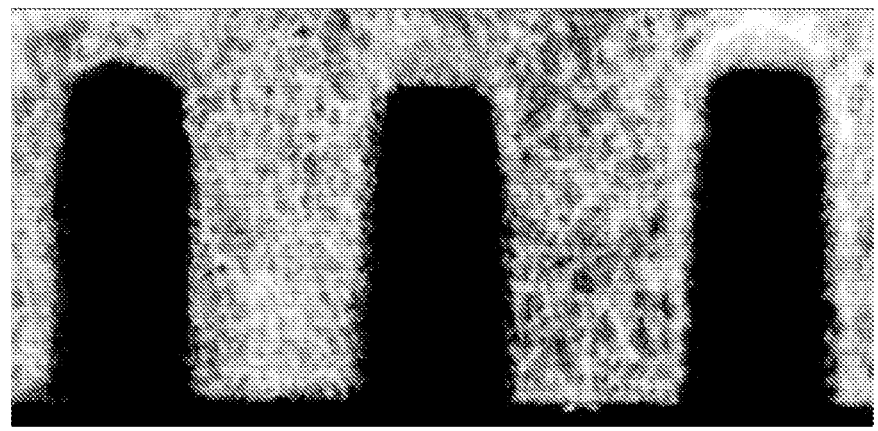
FIG. 22 is a micro-CT image showing a transverse slice through a Porcine03 medial tibial plateau with comparative holes created by a prior art burr drill and a rotary osteotome rotated in both cutting and densifying directions.
Figure 23A:
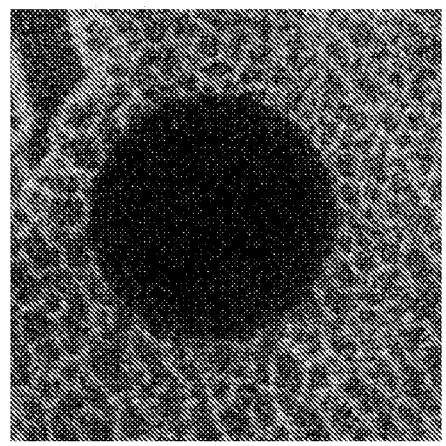
FIGS. 23A-D are micro-CT images showing comparative axial slice views of Porcine02 and Porcine03 medial tibial plateau holes created by a rotary osteotome in both cutting and densifying directions.
Figure 23B:
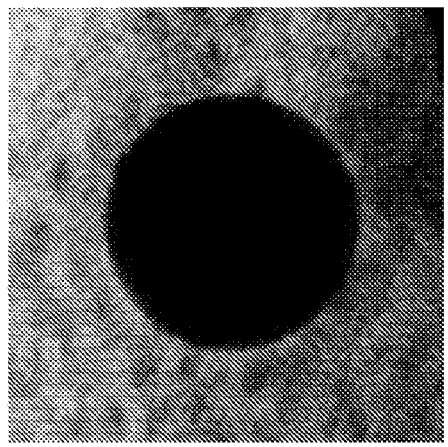
Figure 23C:
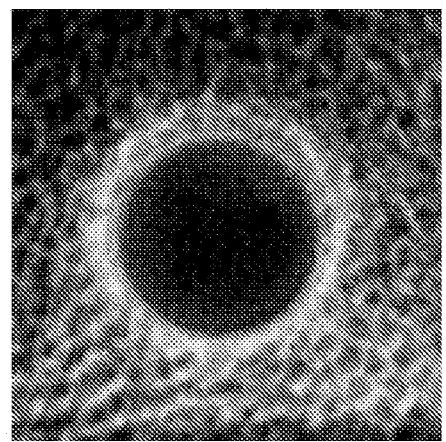
Figure 23D:
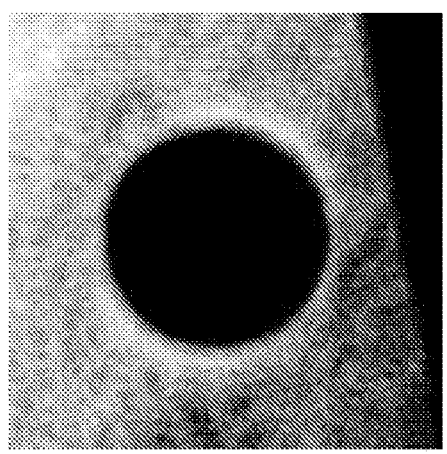

FIGS. 22-23D are micro-CT images developed in Porcine tibia. FIG. 22 is a transverse slice through a Porcine03 medial tibial plateau with comparative holes created by three different methods. The far-left osteotomy was created using a prior art burr drill. Note the rough, uneven side walls. The center osteotomy was created by a rotary osteotome 36 as in FIG. 6 rotated in a cutting direction (i.e., in the cutting mode). Note the relatively clean/uniform side walls. The far-right osteotomy was generated by the rotary osteotome 36 of FIG. 6 rotated in a counter-clockwise direction (i.e., in the densifying mode).

FIGS. 23A-D are micro-CT images developed in different types of Porcine tibia using the rotary osteotome 36 of FIG. 6 rotated in both cutting and densifying directions. FIGS. 23A and 23C both portray axial slice views of Porcine03 medial tibial plateau holes. FIGS. 23B and 23D both portray axial slice views of Porcine02 medial tibial plateau holes. In FIGS. 23A & 23B, the rotary osteotome 36 was rotated in the cutting direction (cutting mode). In FIGS. 23C & 23D, the rotary osteotome 36 was rotated in the reverse direction (densifying mode). These images are compared and contrasted with one another to illustrate the effects of the same rotary osteotome 36 rotated clockwise to accomplish cutting and counterclockwise to accomplish osseodensification in two different bone types. A densification crust (buttressing layer) in the bone side walls can be identified by the white regions surrounding the osteotomies in FIG. 22 (far-right) and FIGS. 23C and 23D.

To summarize, osseodensification is a method to preserve bone and its collagen content to enhance its plasticity. It will allow for enlarging an osteotomy 32 by compacting (and/or by cutting when rotation is reversed) with a rotary osteotome 34 in preparation for a subsequently placed implant or fixture 34. The basic steps of the method begin with the provision of a host material, which in the preferred embodiment is bone however in other contemplated applications could either a cellular or non-cellular non-bone materials. A precursor hole 32 is also created in the host material. This precursor hole could either be a pilot hole drilled with a relatively small diameter standard twist drill or a hole formed by previous application of the cutting or densifying techniques of a precursor rotary osteotome. In either case, the precursor hole 32 has an interior surface (i.e., sidewall 76) that extends between a generally circular entrance 33 in an exposed surface of the host material and a bottom 35 that is closed, most commonly by the host material. The bottom 35 will have a generally conical shape as created by the tip of the pilot drill or preceding osteotome 36. If the precursor hole is formed by a previous application of a rotary osteotome 36, then its interior surface will be tapered with a frusto-conical shape, and with the entrance 33 having a slightly larger diameter than the bottom 35.

The method further includes the step of providing a rotary osteotome 36 configured to be turned at high speed in either a cutting or densifying direction. Whether the osteotome 36 is enlarging by compacting or by cutting, it rotates at high speed as opposed to low-speed oscillating/rocking motions as taught by some prior art systems. The osteotome 36 comprises a shank 40 and a body 42 joined to the shank 40. The body 42 has an apical end 48 remote from the shank 40, and a conically tapered profile that decreases from a maximum diameter adjacent the shank 40 to a minimum diameter adjacent the apical end 48.

The osteotome 36 is operatively connected to a surgical motor 38, with its rotation speed set somewhere between about 200-2000 RPM and its torque setting at about 5-50 Ncm. During the procedure, copiously irrigation is provided in the form of a continuous stream of a substantially incompressible liquid 102 onto the rotating body 42 adjacent the entrance 33 to the precursor hole 32.

The body 42 is continuously rotated in a densifying direction while its apical tip 48 is forcibly advanced by the surgeon into the entrance 33 of the precursor hole 32. Continued advance results in an enlargement of the precursor hole 32 by forcibly pushing the rotating body 42 so that its working edges 72 sweep against the interior surface of the precursor hole 32 to gently expand the bone by incremental plastic deformations that cause a progressive enlargement of the precursor hole 32 beginning adjacent the entrance 33 and developing in a frustoconical pattern downwardly toward the bottom 35. This enlarging step preferably includes axially stroking or pumping the rotating body 42 within the precursor hole 32 so that the working edges 72 alternately lap against the bone interior surface with downward motion and then separate from the interior surface with upward motion in ever deepening movements that cause a progressive plastic deformation of the interior surface of the precursor hole. When the working edges 72 are in physical contact with the bone, the surgeon can manually apply variable axial pressure depending on the haptic sensed responsiveness of the bone. The enlarging step also includes lapping the working edges 72 against the interior surface of the precursor hole 32 without the working edges 72 cutting into the surrounding bone, and in a manner where the rate of advance toward the bottom 35 of the precursor hole 32 is independent of the rate of rotation of the body 42. This latter characteristic contrasts with some prior art systems that couple tool rotation with the rate of advance.

Notable improvements in this present invention include: grinding a progressively larger amount of bone material with the apical end 48 as the body 42 is advanced deeper into the osteotomy 32, auto-grafting the ground bone material into the host bone within the osteotomy 32 and compacting the ground bone material into the host bone with the fluted body 42, and also generating an opposing axial reaction force (Ry) in opposition to the advancing direction of the body 42 into the osteotomy 32. The opposing axial reaction force (Ry) is created by the configuration of the lips 50 and/or the working edges 72.

After removing the osteotome 36 from the expanded hole, additional expansion steps can be practiced to make the hole even larger, or the fixture portion of an implant 34 or other anchoring device can be inserted into the prepared osteotomy 32. The step of installing a fixture 34 or anchor would include directly engaging an exterior anchoring thread form of the fixture 34 or anchor into the expanded hole that has been formed by the working edges 72.

The tools and techniques of this invention are readily adaptable to the methods of computer generated implant placement guides, like those described for example in the Applicant's own WO 2016/187493 to Huwais, published Nov. 24, 2016 (the entire disclosure of which is hereby incorporated by reference in jurisdictions permitting incorporation by reference). According to these methods, a computer model is created giving jawbone 30 structural details, gum surface shape information and proposed teeth or dental prosthesis shape information. The computer model shows the bone structure, gum surface and teeth images properly referenced to one another so that osteotomy 32 positions can be selected taking into consideration proper positioning within the bone 30 as well as proper positioning with respect to the implant 34.

Figure 24:
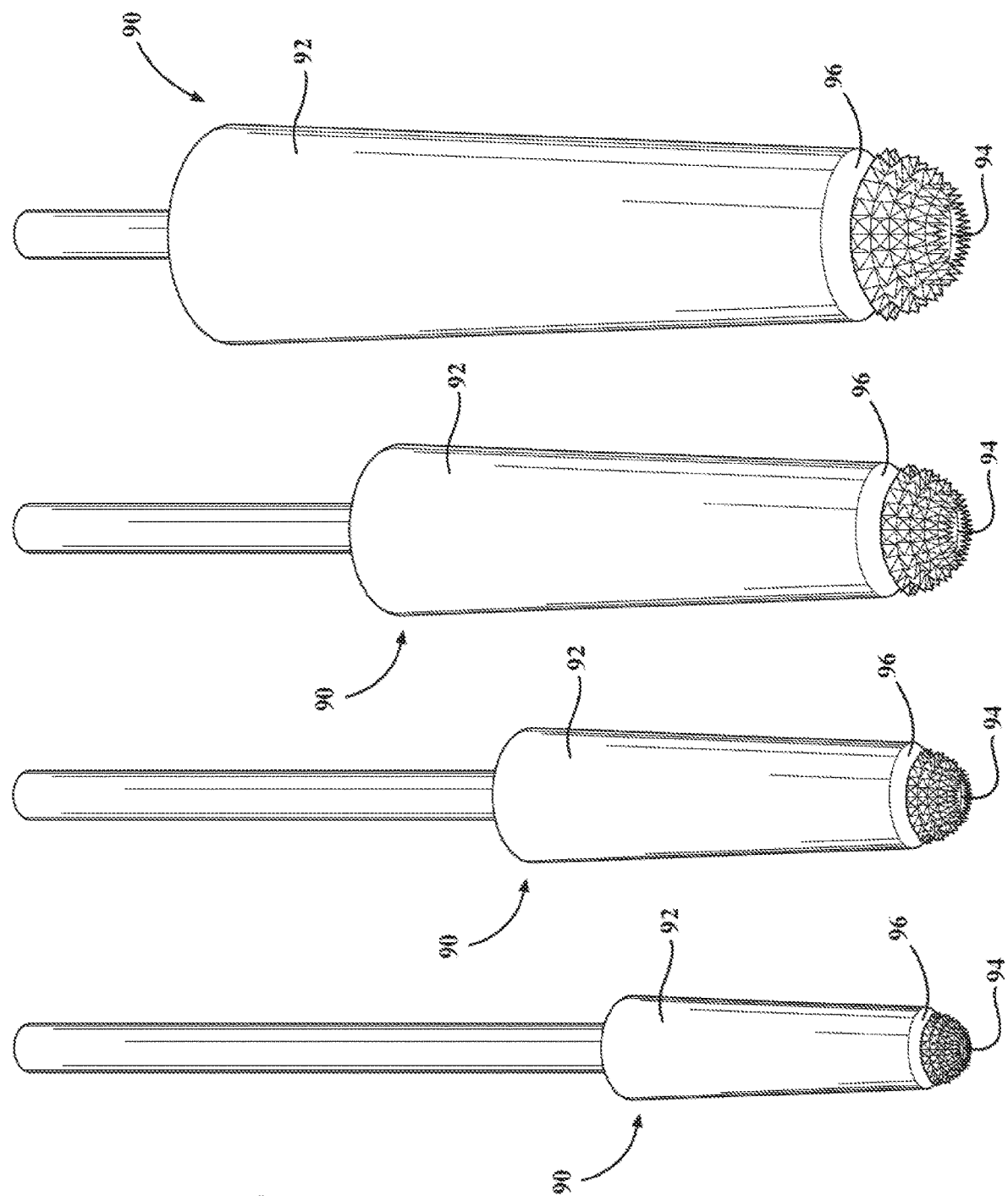
FIG. 24 shows an alternative embodiment of the osteotome of this invention configured for high-frequency vibration rather than rotation.
Figure 26:
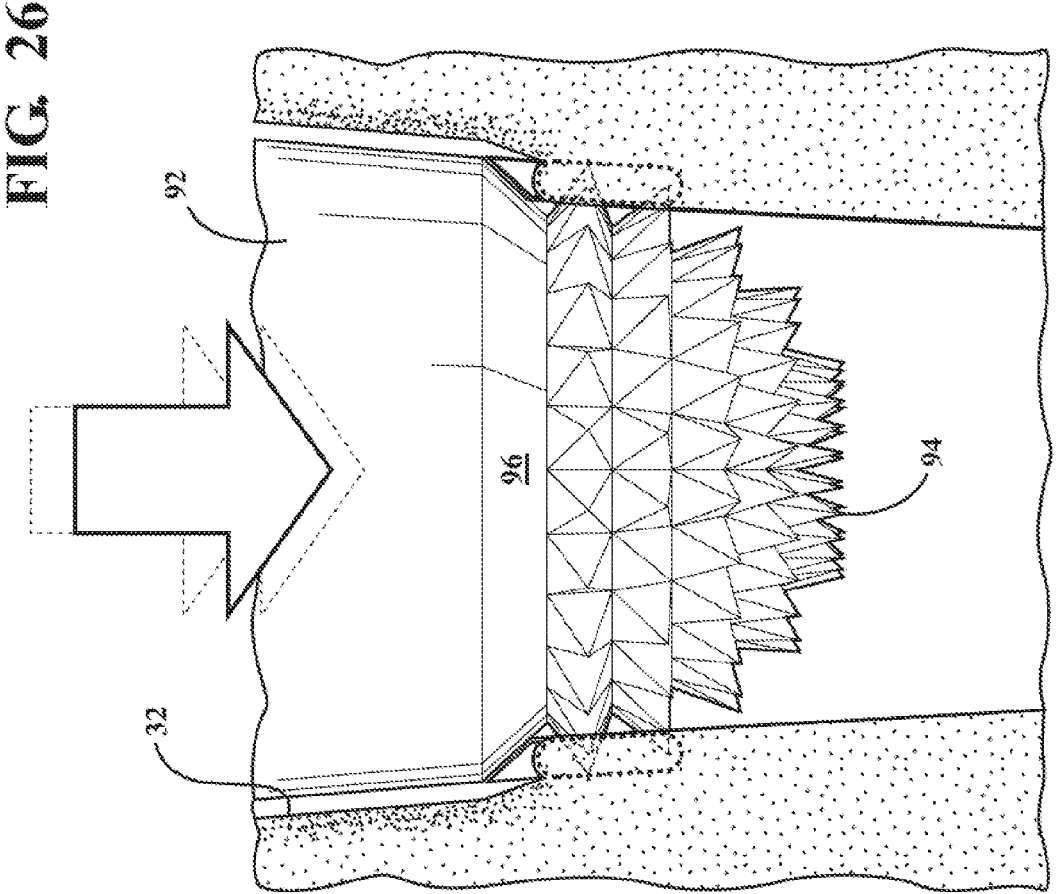
FIG. 26 is an enlarged view of the apical end of the alternative osteotome of FIG. 24.
Figure 25:
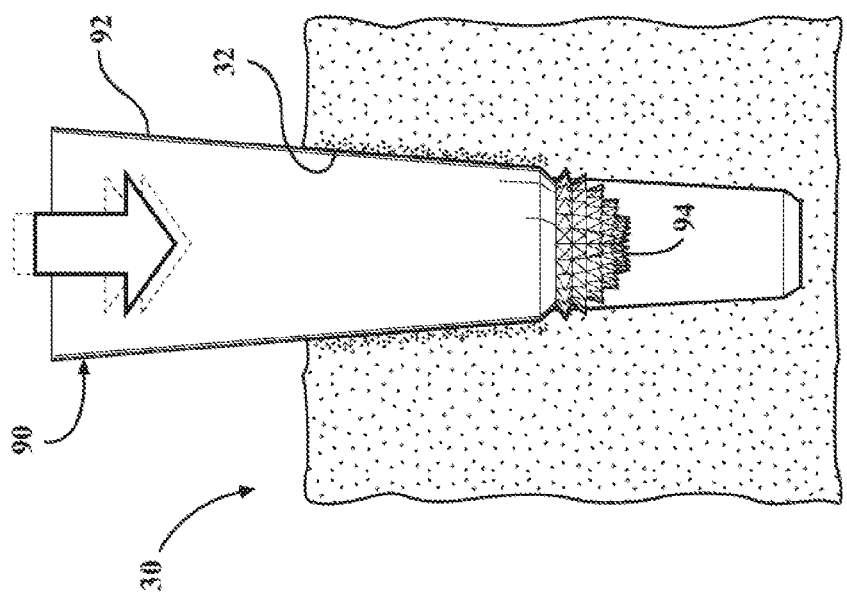
FIG. 25 is a cross-section through an osteotomy with the alternative osteotome of FIG. 24 disposed partially completing an expansion procedure according to this invention.

FIGS. 24-26 illustrate an alternative embodiment of this invention, namely an ultrasonic osteotome 90 configured to enlarge an osteotomy without rotation. The ultrasonic osteotome 90 includes a shank and an adjoined body 92. The body 92 having an apical end 94 remote from the shank. The body 92 is generally smooth (i.e., non-fluted) and has a conically tapered profile decreasing from a maximum diameter adjacent the shank to a minimum diameter adjacent the apical end 94. The overall proportion and dimensions of the body 92 will be similar to those of the body 42 in the preceding examples. The apical end 94 includes a unidirectional grinding formation that may take the form of a roughed surface. As the ultrasonic osteotome 90 is vibrated at a high frequency (as by a commercial off-the-shelf surgical ultrasonic generator) the apical end 94 has the effect of grinding some small portion of bone in a manner not too dissimilar from that of the apical end 48 in the earlier embodiments. The body 92 further includes an auto-grafting ramp 96 configured to auto-graft and compact bone after the bone has been ultrasonically pulverized by the apical end 94 as the body is forcibly advanced into an osteotomy concurrently with high-frequency vibration. In this example, the auto-grafting ramp 96 is a frusto-conical member disposed immediately below the smooth tapered portion of the body 92. The auto-grafting ramp 96 extends at a first angle that is larger than the taper of the body 92 so that the granular bone debris will be packed into the surrounding walls of the osteotomy with wedge-like action.

Figure 27A:
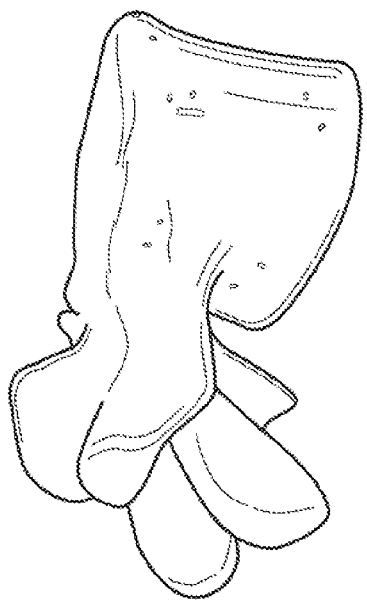
FIG. 27A is an enlarged view of a human vertebrae.
Figure 27B:
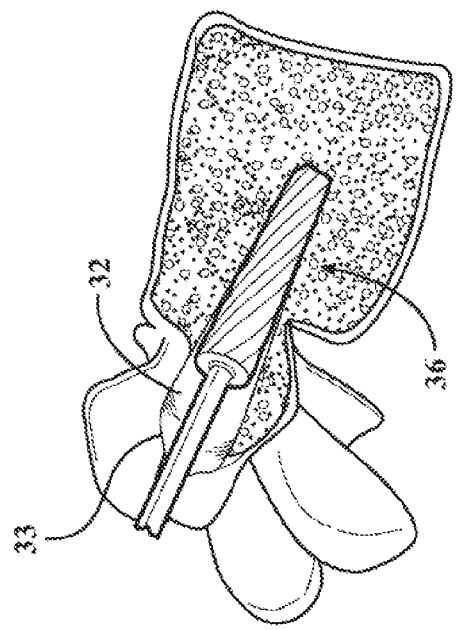
FIG. 27B is a view of the vertebrae as in FIG. 27A shown in cross-section with a rotary osteotome according to one embodiment of this invention disposed to enlarge an osteotomy for the purpose of receiving a fixation screw or other implant device.
Figure 27:
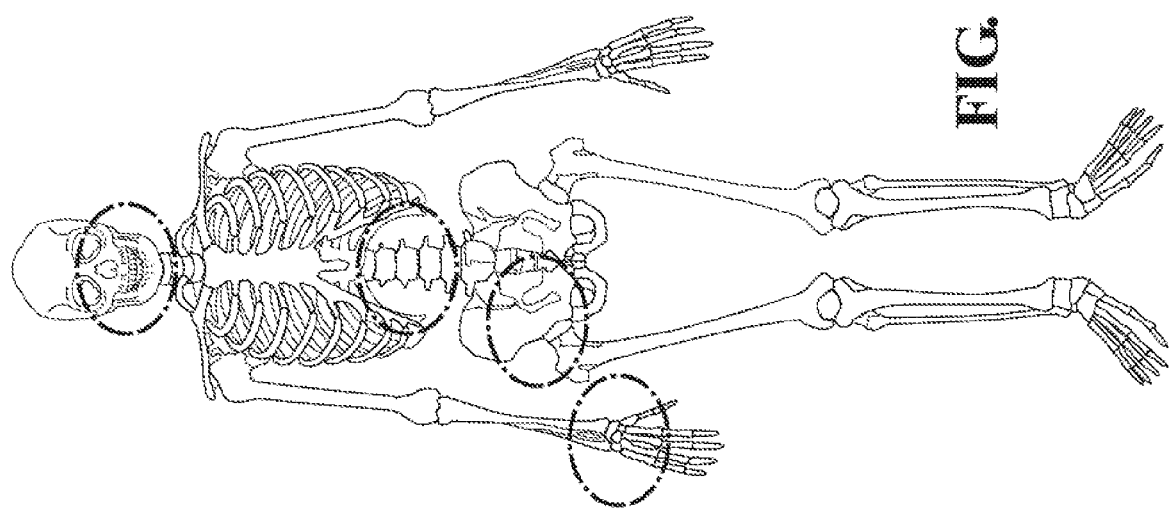
FIG. 27 is a simplified depiction of a human skeleton highlighting some examples of areas in which the novel osteotome of this invention might be effectively applied.

FIGS. 27-27B are intended to illustrate, for the benefit of the skilled artisan, that the principles of this invention are not limited to dental applications, but any bone preparation site within the human (or animal) body may be investigated for suitability. Initial indications reveal that applications in the vertebrae and hand/wrist are prime candidates for osteotomies 32 formed with a rotary osteotome 36. However, the potential range of applications is not limited to the indicated regions in FIG. 27, nor even to human patients.

Figure 28:
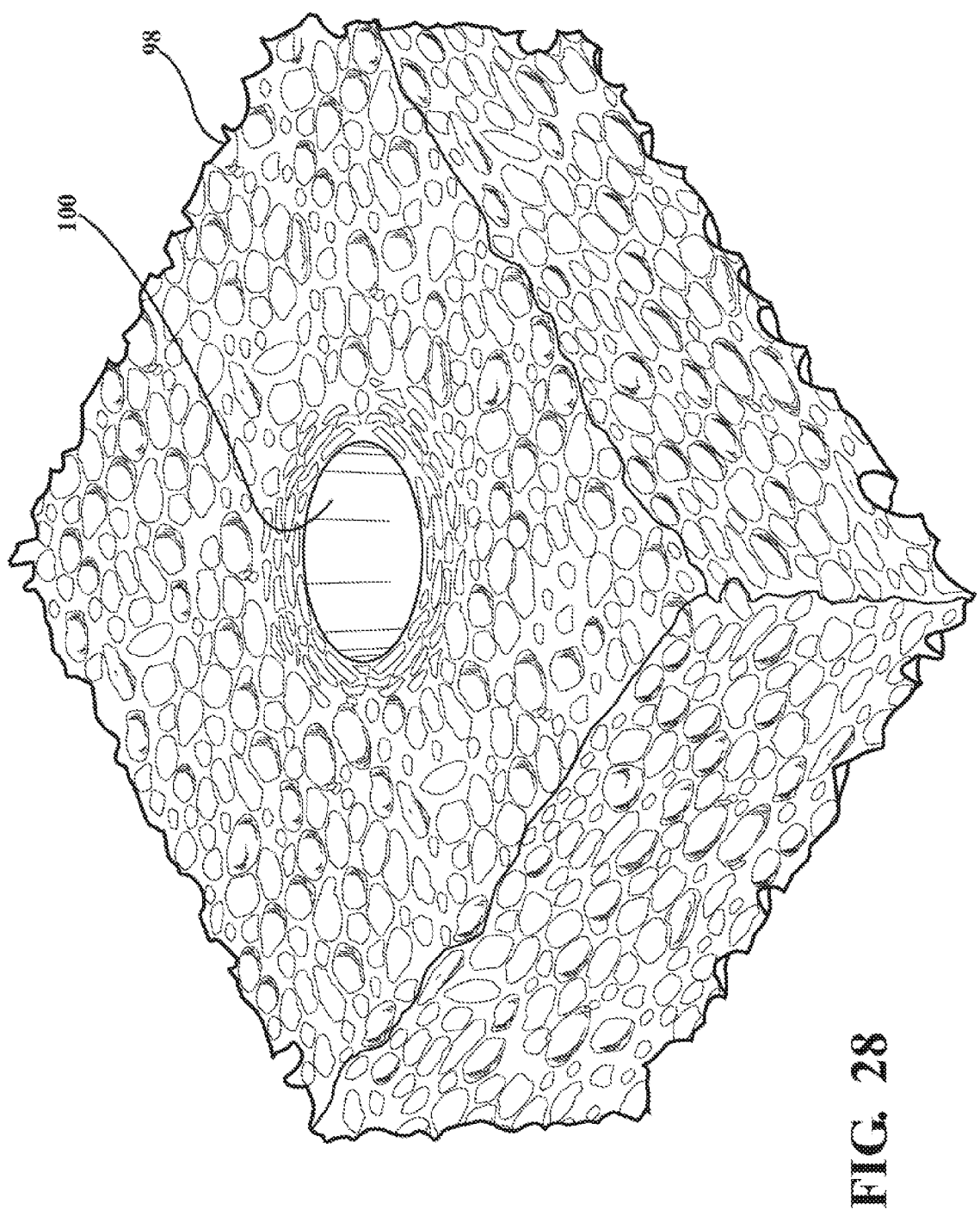
FIG. 28 is a perspective view of a foam metal product having a hole formed therein using a rotary osteotome according to this invention exemplifying at least one non-bone commercial application.

Furthermore, as shown in FIG. 28 the principles of this invention are not limited to bone as the host material. Indeed, the osteotome or rotary tool 36 of this invention may be configured to enlarge a hole in almost any type of cellular or solid material by cutting and/or compacting. (In non-medical applications, the osteotome 36 should be identified as simply a tool or rotary tool to avoid confusion with the osteo-prefix which implies use in bone.) In this illustration, a section of metal foam 98 may be of the type used in aerospace, heat shielding and other critical applications. The foam metal is shown including a hole 100 formed by compacting according to the methods described above. The resulting hole 100 is better prepared to receive a screw or other fixation anchor because its inner sidewall has been densified by the compressive displacement and auto-grafting effects of this invention. In addition to foam metals, any inorganic materials that have visco-elastic properties similar to live bone are especially good candidates. Some experimentation has been made as well with hole formation in non-cellular inorganic materials like plate aluminum and plastic. Certain benefits have presented as well in these non-cellular materials, such that the potential to improve screw or anchor retention by hole preparation using the principles of this invention are fully contemplated.

Referring now to FIGS. 29-32, an enhanced operational mode of the present invention will be described when combined with a continuous flow of irrigation fluid 102, such as by an external irrigation hand piece. The irrigation fluid is preferably an incompressible liquid like sterile saline solution or water, however other suitable liquids could be used instead.

Figure 11:
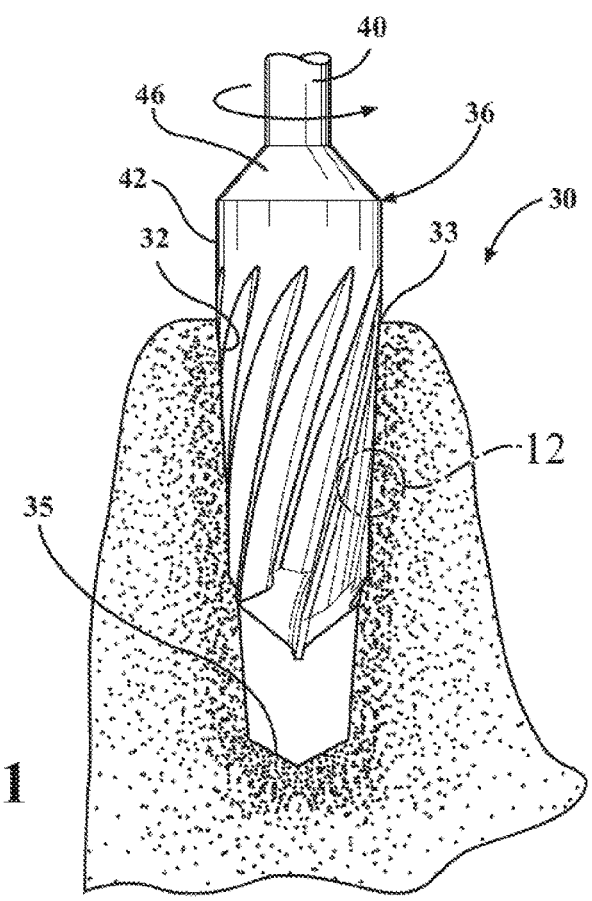
FIG. 11 depicts a cross-section through an osteotomy with a rotary osteotome disposed partially within as in the midst of an expansion procedure according to this invention.
Figure 29:
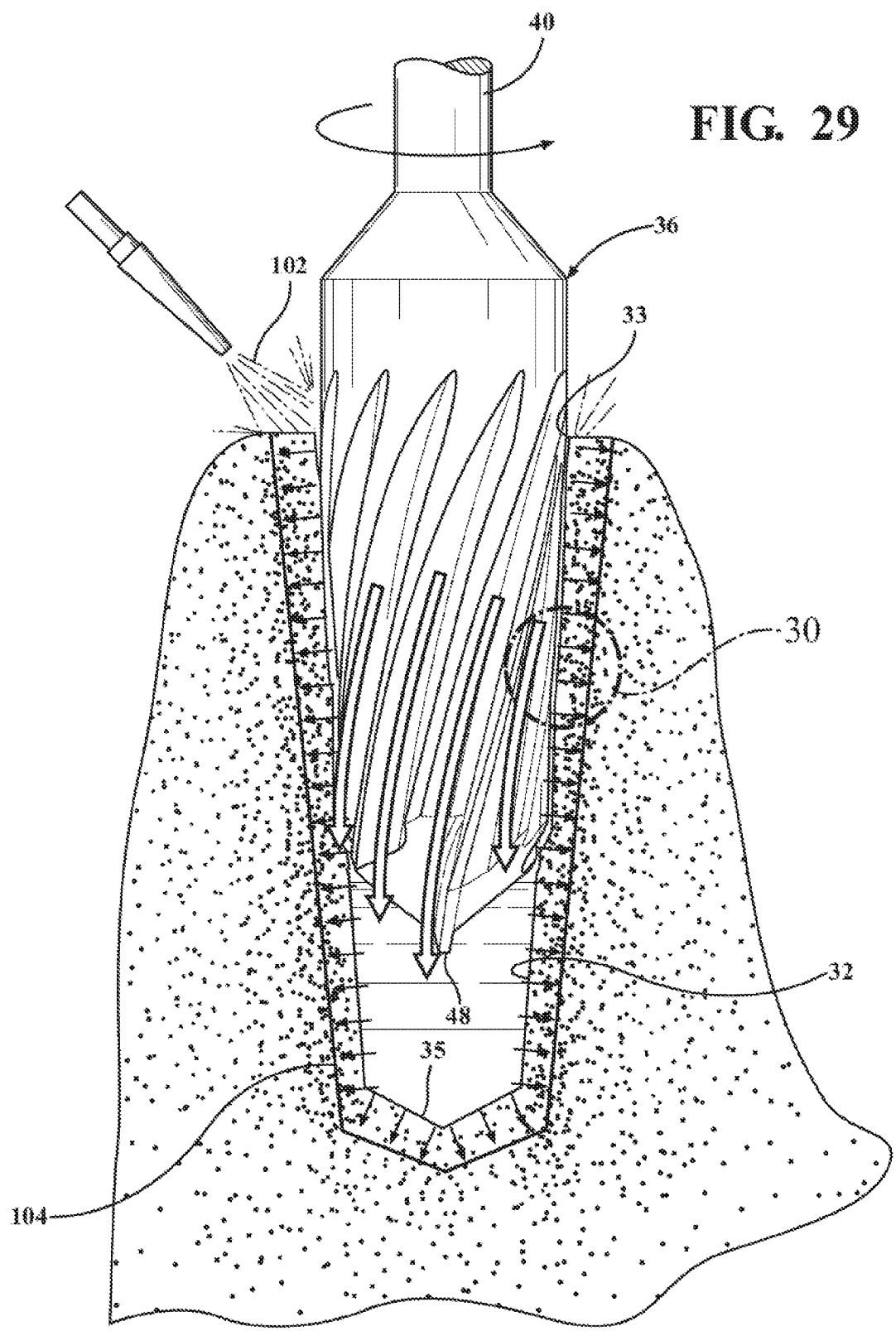
FIG. 29 is a cross-sectional view as in FIG. 7 showing osteotome slightly raised out of contact with the inner sidewall of the osteotomy with irrigating fluid being forcefully propelled in-between the flutes like a screw pump toward the bottom of the precursor hole, and depicting a generally uniform pressure gradient in the surrounding irrigating fluid by the use of radiating arrows.
Figure 30:
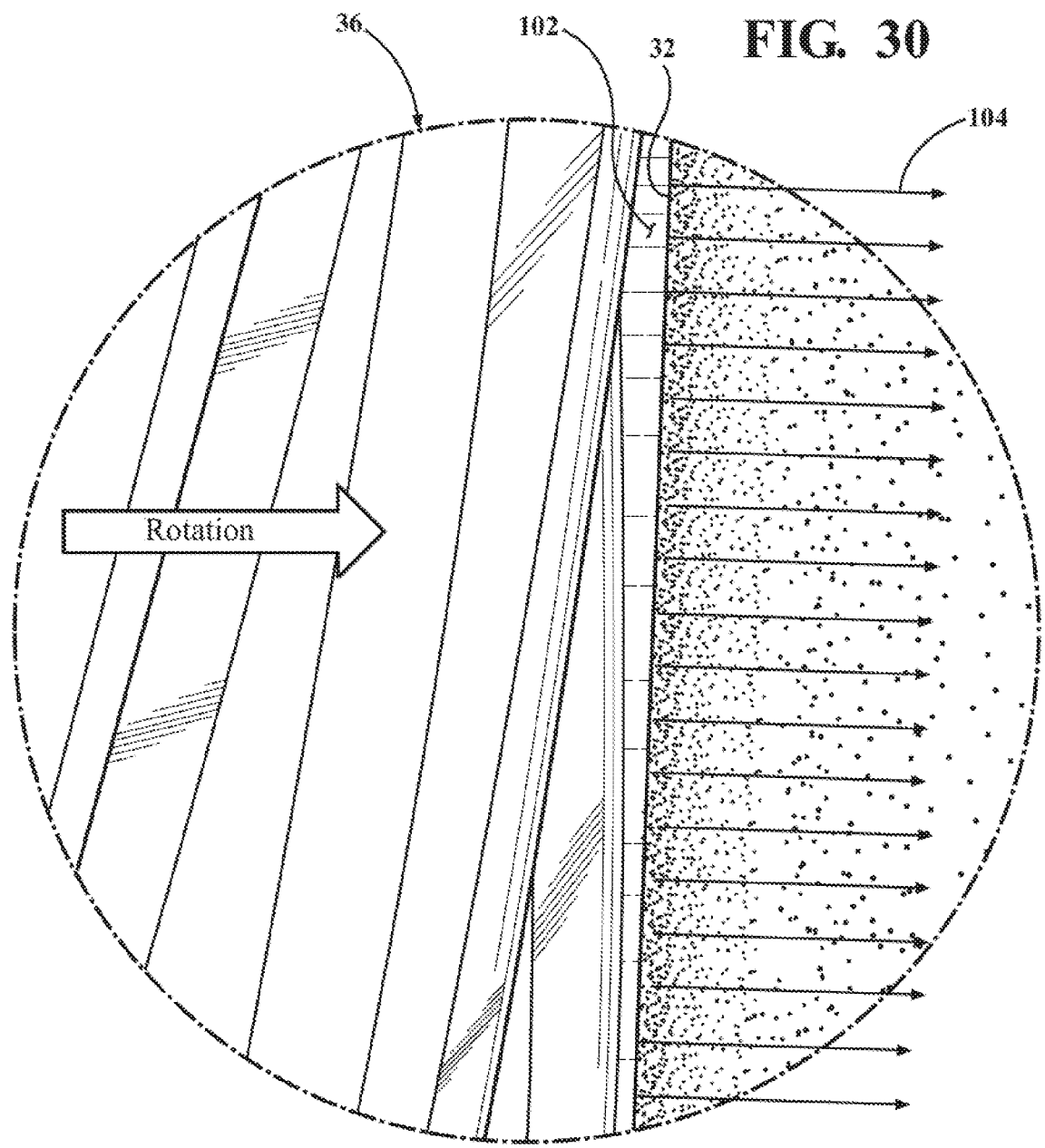
FIG. 30 is an enlarged view of the area circumscribed at 30 in FIG. 29 showing the physical separation between the osteotome body and the inner sidewall of the osteotomy.

FIG. 29 corresponds, generally, to FIGS. 7 and 11 but with a particular distinction—the working edges 72 of the osteotome 36 are slightly separated from the inner sidewall of the osteotomy 32 as occurs repeatedly while practicing the controlled "bouncing" technique described above. This separation is visible in the magnified view of FIG. 30. When a continuous flow of irrigating fluid 102 is provided and the rotary osteotome 36 is rotated in the densifying mode, the reverse twist of the flutes 62 propels (pumps) the irrigation fluid 102 down toward the bottom 35 of the osteotomy 32. That is, the flutes 62 transport the irrigating fluid something akin to the axial thrust-giving elements of a screw pump or marine propeller. As a result, irrigating fluid 102 is forcefully driven toward the bottom 35 of the precursor hole throughout the surgical procedure. This pumping or propelling action is depicted by the downwardly twisting arrows in FIG. 29.

Excess irrigation fluid 102 is continually pushed out of the osteotomy 32 in the gap around the osteotome 36. (It will be appreciated that when the tool 36 is used in non-medical applications, instead of an osteotomy 32 the tool 36 is placed in the entrance to a hole 100 in the surface of a host material.) Thus, so long as the flow of irrigating fluid 102 is maintained and the osteotome 36 is rotated inside the osteotomy 32, a hydraulic pressure is created that pushes outwardly within the osteotomy 32. A generally uniform pressure gradient 104 in the irrigating fluid is illustrated by radiating arrows. When operated in the densifying mode, the pressure gradient pushes against the bone side walls at all times during the surgical procedure, preparing and preconditioning the interior surface of the precursor hole prior to the enlarging step.

When the tapered osteotome 36 is held (by the surgeon) so that its working edges 72 are maintained in separation from the inner side walls of the osteotomy 32, the propelled hydrating pressure created by the downward pumping action of the flutes 62 will be generally equally distributed across the entire inner surface of the osteotomy 32 according to the general principles of hydraulics and fluid dynamics. As the surgeon moves the rotating osteotome 36 deeper into the osteotomy 32 but still its working edges 72 do not directly contact the inner side walls of the osteotomy 32, as shown for example in FIGS. 29 and 30, the hydraulic pressure will increase within the osteotomy 32. Excess irrigation fluid 102 continues to be exhausted out of the osteotomy 32 but through a smaller circular gap around the osteotome 36, which leads to the increase in hydraulic pressure.

The pressure gradient 104 will thus increase and decrease in direct response to the amount of force applied by the surgeon as he or she repeatedly advances and relaxes the rotating osteotome 36 into the osteotomy 32. The pressure gradient 104 will be smallest when the osteotome 36 is held far away from the side walls of the osteotomy 32; and conversely will be largest when the working edges 72 of the osteotome 36 are pushed hard into the side walls of the osteotomy 32. By modulating the position of the osteotome 36 in combination with a continuous supply of irrigation fluid 102, the surgeon can apply an evenly distributed, expansive pressure with piston-like effect to the inner side walls of the osteotomy 32—without physically touching the walls of the osteotomy 32 with the working edges 72. This throbbing hydraulic effect has many preconditioning advantages, which include: 1) gentle pre-stressing of the bone structure of the osteotomy 32 in preparation for subsequent compacting contact, 2) haptic feedback transmitted through the osteotome 36 that allows the surgeon to tactically discern the instantaneously applied pressure prior to actual contact between the osteotome 36 and side walls, 3) enhanced hydration of the bone structure which increases bone toughness and increases bone plasticity, 4) hydraulically assisted infusion of bone fragments 80 into the lattice structure of the surrounding bone, 5) reduced heat transfer, 6) hydrodynamic lubricity, 7) dampening or cushioning of the trauma sensed by the patient, and so forth.

With regard to the haptic feedback advantages, the pressurized irrigation fluid 102 will have a significant amplifying effect as compared to an imagined scenario in which no irrigating fluid is used. In the latter hypothetical, haptic feedback is produced solely by the direct physical contact between the bone sidewalls and the working edges 72 and lips 50. When the surgeon "bounces" the osteotome in use, haptic feedback would abruptly stop the moment there is a separation between the bone sidewalls and the working edges 72 and lips 50. However, with irrigating fluid 102 the haptic feedback is augmented by reaction forces all along the apical tip 48 as well as by the pressure gradient 104 that surrounds the osteotome 36 even when there is a slight separation between the bone sidewalls and the working edges 72 and lips 50 as in the example of FIG. 30.

Figure 31:
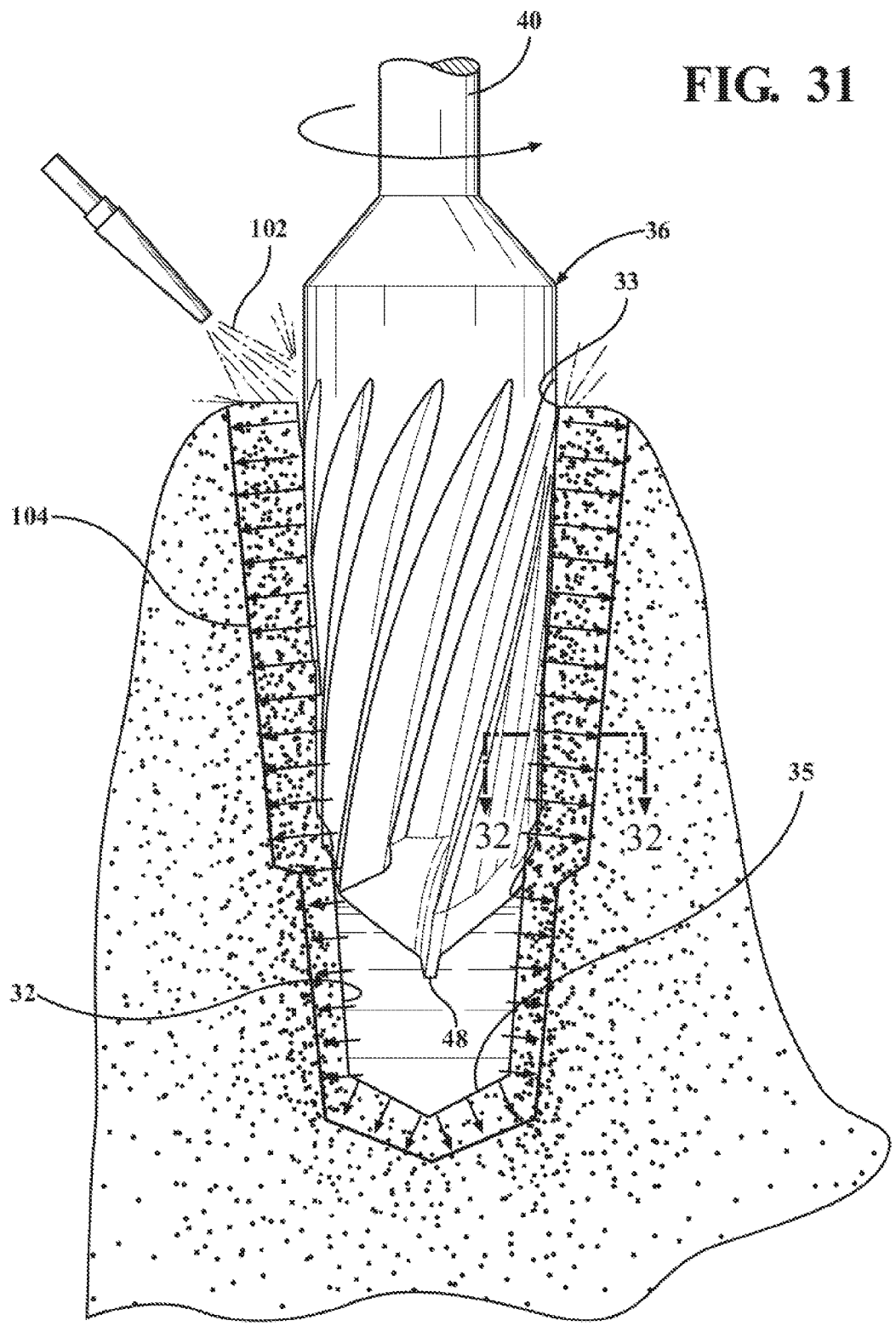
FIG. 31 is a view as in FIG. 29 but showing osteotome pressed down into contact with the inner sidewall of the osteotomy and the resulting changes in pressure applied to the inner sidewall of the osteotomy.

FIG. 31 depicts, graphically, the pressure gradient 104 as exerted against the inner side walls of the osteotomy 32 when the surgeon brings the working edges 72 of the spinning osteotome 36 into direct contact with the bone side walls. Arrows radiating normally from the side walls of the osteotomy 32 continue to represent the pressure gradient 104. When the working edges 72 of the osteotome 36 breach the hydrodynamic buttressing layer, they will perform the compacting action described in detail above. In the region of direct contact, the pressure gradient 104 will experience a sharp increase as a result of mechanically applied pressure through the working edges 72, which in turn causes the bone structure to plastically deform. Meanwhile, the irrigating fluid 102 trapped below the osteotome 36 will continue to apply a preconditioning hydro-static pressure below the apical tip 48 of the osteotome 36. By axially stroking the rotating body 42 within the precursor hole 32, the hydraulic pressure inside the precursor hole will modulate in direct response to the surgeon's movements. And so, in practice a surgeon will repeatedly apply and relax force on the continuously rotating osteotome 36 to progressively advance the osteotome 36 deeper and deeper toward its bottom 35 until a desired final depth is reached. The hydraulic assist provided by the irrigating fluid 102 enables a much cooler, faster, smoother and controllable expansion procedure. Furthermore, the dampening effect provided by the hydraulic action of the irrigating fluid 102 helps to cushion the patient's sensation of force applied by the surgeon, thereby resulting in a more comfortable experience.

Figure 32:
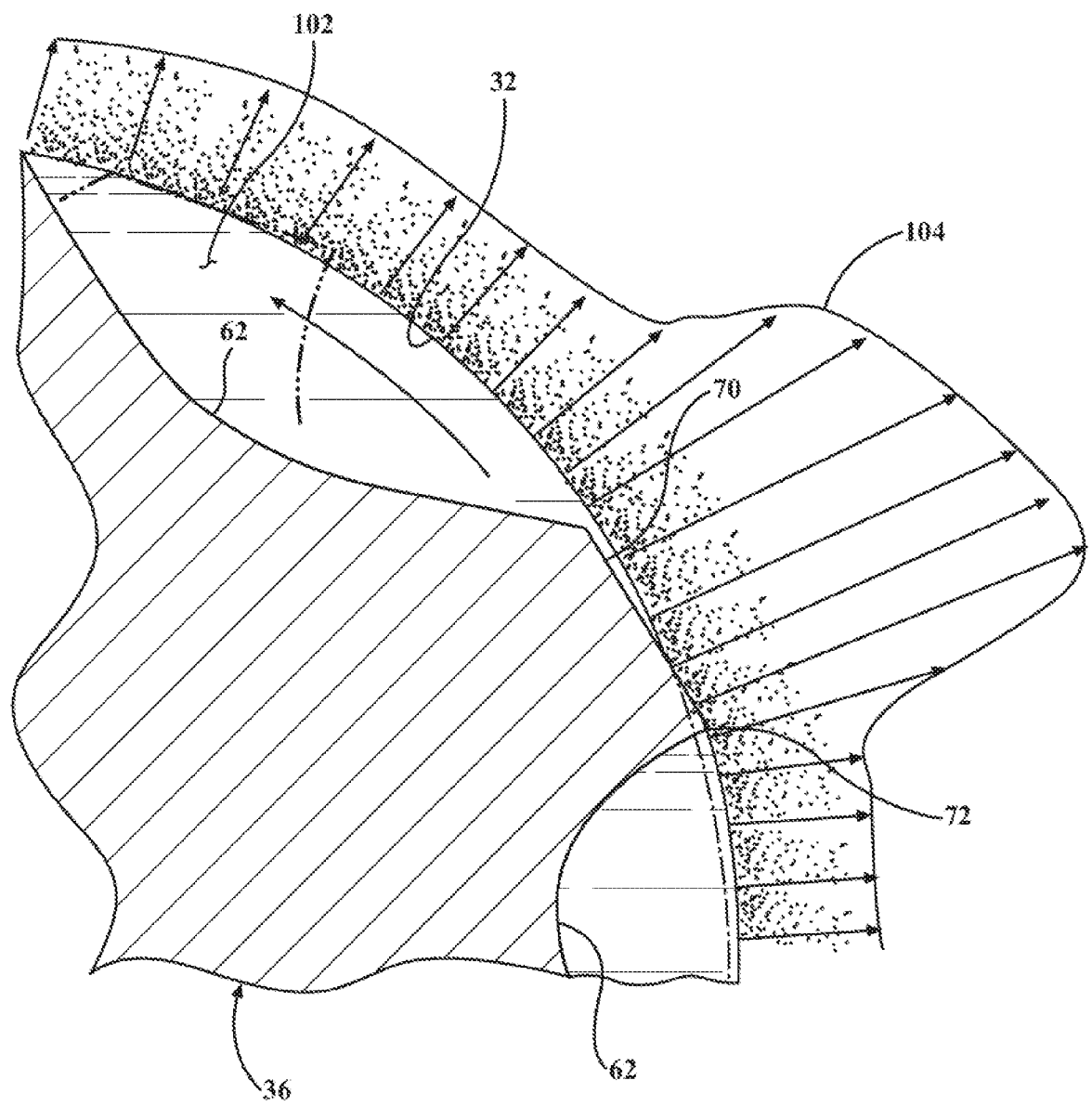
FIG. 32 is a fragmentary cross-sectional view taken generally along lines 32-32 of FIG. 31 showing the elevated hydrodynamic pressure spike generated against the bone sidewall immediately prior to contact with a working edge.

FIG. 32 depicts a horizontal cross-section through the osteotomy 32, as taken generally along lines 32-32 in FIG. 31. FIG. 32 offers a snap-shot of the instantaneous pressure gradient 104 around one working edge 72 of the osteotome 36. As can be readily see from this view, the instantaneous pressure gradient 104 will be relatively low in the region of the flutes 62. It may be expected that the instantaneous pressure gradient 104 in the region of the flutes 62 will be close in value to the pressure gradient below the apical tip 48 of the osteotome 36. However, the pressure quickly increases, i.e., spikes, as the land faces 70 act like wedges to quickly compress the fluid 102 in advance of the working edges 72. The irrigating fluid 102 trapped between the land faces 70 and the inner wall of the osteotomy 32 acts as a high-pressure cushion layer always ahead of (i.e., leading) the working edges 72, and together act vigorously on the bone structure of the osteotomy 32 to help expand its diameter and produce a buttressing layer (densification crust) in bone (or a hardening crust in case of metals and other non-bone host materials). The working edges 72, which perpetually trail the high-pressure cushion layer during rotation in the densifying direction, break through the cushion layer to make direct contact with the bone side walls when enough downward force is applied by the surgeon.

When direct bone-to-edge contact is made, the working edges 72 perform the compacting action described above to simultaneously expand the osteotomy 32 and create the densification crust (buttressing layer) in the bone side walls. However, as soon as the surgeon lifts the osteotome 36 even a little, more irrigating fluid 102 washes over the just-burnished surface. Therefore, when the surgeon gently lifts the osteotome 36 up after having made some expansion progress, a wash of pressurized irrigating fluid 102 immediately enhances hydration of the bone structure, gently pre-stresses the bone structure in preparation for further compacting by the working edges 72, hydraulically infuses bone fragments 80 into the lattice structure of the surrounding bone, cools the interface, and so forth. This cycle may repeat many times as the surgeon gently bounces the rapidly spinning osteotome 36 toward final depth. In many cases, the surgeon will bounce the spinning osteotome 36 into and out of contact with the bone sidewall some 5-20 times before reaching the bottom 35. With each bounce, the hydraulic pressure surges just prior to direct contact to precondition the osteotomy 32 and thereby improve both performance and results.

The method of this invention therefore includes the step of preconditioning the interior surface of the precursor hole 32 prior to the above-described enlarging step. The preconditioning step includes building hydraulic pressure inside the precursor hole 32 between the apical tip 48 and the bottom 35 by the propelling the incompressible liquid 102 in-between the flutes 62 of the high-speed rotating osteotome 36 toward the bottom of the precursor hole 32. The hydraulic pressure can be modulated inside the precursor hole 32 in direct and somewhat proportional response to the step of axially stroking the rotating body 42 within the precursor hole 32. The preconditioning step further includes generating an elevated hydrodynamic pressure surge or spike immediately upstream of, that is in the angular direction of rotation, of the working edge 72. The generating step further includes locating the pressure spike radially outwardly from the land face 70 of each land. As shown graphically in FIG. 32, the hydrodynamic pressure spike is less than the mechanical pressure generated in the host material by direct physical contact of the working edge 72, but greater than the pressure gradient in the pockets of the flutes 62.

The present invention, when operated with a continuous supply of irrigating fluid 102, may be used to form holes in many different types of materials in addition to bone. For examples, malleable metals (e.g., aluminum) or plastics may be used at the host material. The irrigating fluid in these circumstances may be an oil or cutting-fluid substance rather than water or saline. When the non-bone host material is cellular, like in the case of foam metals and polymers, the host material may behave somewhat like bone. However, when the host material in not cellular but rather solid, displaced stock will have a tendency to mound above and below the hole rather than being auto-grafted into the sidewalls of the hole 100. This mounding represents malleable material that is plastically displaced by the compression wave of the working edge 72, and further enhanced overall by the aforementioned hydraulic assistance. As a result, the effective stock thickness around a hole formed in non-cellular material will be substantially greater than the original stock thickness.

Accordingly, the present invention may be used in non-medical applications as a tool and method of hole formation characterized by hydrodynamic compacting. Advantages and benefits of hydrodynamic compacting include low plastic deformation due to rolling and sliding contact with rotating tool 36. Hydrodynamic compacting occurs with a tool 36 that has working edges 72 to densify the side walls of the hole as it is formed. Lubrication/irrigation is provided to eliminate overheating and to create a viscose hydrodynamic layer of densification, among many other advantages. Hydrodynamic compacting occurs when the load is well controlled beneath the ultimate strength. Hydrodynamic compacting occurs where a large negative rake angle (non-cutting edge) is used as a compacting edge. While regular twist drills or straight fluted drills have 2-3 lands to guide them through the hole, hydrodynamic compacting drills preferably have 4 or more lands and flutes.

Those of skill in the art will appreciate that the osteotome of this invention could be configured with a straight or non-tapered body rather than the tapered working end as shown in the illustrations. Accordingly, the described osteotomy enlargement techniques can be accomplished using non-tapered tools via the novel method of compacting in combination with hydrodynamic effects.

Referring now to FIGS. 33-47, a modified and enhanced rotary osteotome is generally indicated at 136. Throughout FIGS. 33-47, reference numbers introduced above but offset by 100 are used to identify like or corresponding features. Thus, the rotary osteotome 136 compares to the rotary osteotome 36 of FIGS. 5-21 and 29-32, and shares many similar features therewith. In fact, the enhanced rotary osteotome 136 and the previous rotary osteotome 36 are substantially identical in most respects save the shaping of their flutes 162, 62, respectively. The flutes 162 of the enhanced rotary osteotome 136 are specially shaped to achieve an outcome not possible with the earlier rotary osteotome 36, namely a moderate degree of densification when operated in the cutting mode. The rotary osteotome 36 of FIGS. 5-21 and 29-32 was not capable of producing a buttressing layer when operated in the cutting mode, as can be discerned by the micro-CT images in FIG. 22 (center) and FIGS. 23A and 23B. However, the modified geometry of the flutes 162 enable the enhanced rotary osteotome 136 to produce a partially densified crust when rotated in the cutting direction. See FIG. 38. The early stage buttressing layer produced in cutting mode by the enhanced rotary osteotome 136 is less developed than when the same enhanced rotary osteotome 136 is operated in the densifying mode. Nevertheless, this ability to achieve some degree of densification in cutting mode can prove useful to the surgeon in many applications, such as hard bone to name one. And, if desired, the buttressing layer can be further enhanced by performing a novel densify-after-cut (DAC) protocol which will be described below.

FIG. 33 is a side elevation of the enhanced rotary osteotome 136. The body 142 of the rotary osteotome 136 includes a stopper section 106 that extends between the terminus of the flutes 162 and the transition 146. The stopper section 106 produces a vital plugging action to prevent the continued migration of bone particles along the flutes 162 in cutting mode, and thereby self-arrest the cutting performance of the osteotome 136 when operated in the cutting direction. FIG. 34, which is a cross-section taken helically along 34-34 in FIG. 33, reveals two diametrically-opposing flutes 162. The flutes 162 of the enhanced rotary osteotome 136 are shaped to progressively decrease in size (i.e., cross-sectional area) from the apical end 48.

In practice, it has been found that the axial length of the stopper section 106 should be at least equal to, and preferably greater than, the average width of the flutes 162. That is, if the average width of the flutes 162, as measured along their full helical length, is 1.8 mm for example, then the axial length of the stopper section 106 should be at least 1.8 mm, for example. In practice, for dental applications, the stopper section will be greater than or equal to about 2 mm, as suggested in FIG. 42. For larger orthopedic applications, the flutes 162 may be larger and thus the stopper section 106 may likewise be taller to achieve the desired plugging action.

Some of the relevant features of the flutes 162 are expressly called out in the cross-sectional FIG. 35. Here, the core diameter 174 is labeled, which corresponds to the depth of the flutes 162 along the length of the body 142. The rake angle is also labeled along one cutting face 166. Also labeled is a heel side angle, which corresponds to the approximate angle of the densifying faces 164 of each flute 162. The relief angle behind each working edge 172 is shown, along with the land width for one of the land faces 170. These diagrams are provided to facilitate comprehension of the following descriptions of the augmented flute 162 geometries which characterize the enhanced rotary osteotome 136.

In the enhanced design, the rake angles (i.e., the angular relationship between each cutting face 166 and a radial passing through the corresponding working edge 172) have been changed to negative (like a burnishing tool) along substantially their entire length. (One alternative embodiment mentioned below describes a variation in which the lower leading portion of each flute has an aggressive zero or even positive rake but transforms to a negative rake approximately mid-body.) The rake angle of the initially-described rotary osteotome 36 was preferably established at zero along the entire length of the flutes 62. See FIG. 16. Although the negative rake angles of the enhanced rotary osteotome 136 can vary widely, grinds between about −1° and −75° (i.e., negative like for a burnishing tool) can enable the new and previously unanticipated advantages of this embodiment while still producing satisfactory cutting results. The stated range can be improved, somewhat, by maintaining the negative rake angles between about −5° and −65°. Even better cutting results can be achieved by setting the rake angles between about −5° and −50°. And in some cases superior results have been achieved when the rake angles are between about −10° and −40°.

Figure 36:
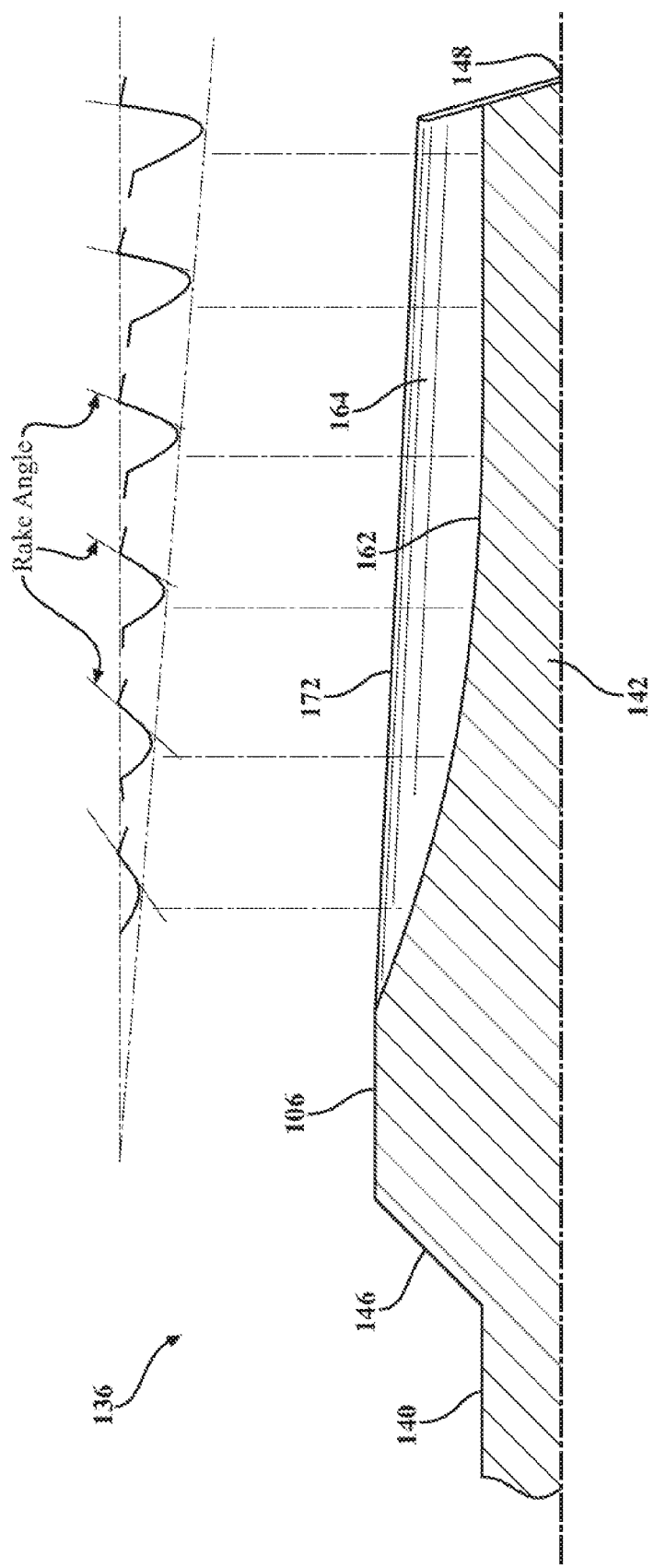
FIG. 36 is partial cross-sectional view as in FIG. 34 but showing the flute formation in exaggerated form to emphasize various optional attributes thereof.

The same or generally the same negative rake angle may be maintained along the entire length of the flute 162. For example, in the images of FIGS. 43-46, the rake angle remains in a relatively tight range of about −13° to −28° (~15° variance) along the lengths of the flutes 162. Specifically, the rake angles are measured at about −28°/−18°/−13°/−24° for FIGS. 43-46, respectively. Fluctuations like this may, in some instances, be mandated by manufacturing constraints. The negative rake angle can be intentionally designed to change along the length of the flutes 162 rather than being held to a tolerance. The change can be relatively small (e.g., <30° variance) or relatively large (e.g., >30° variance). Intentional changes in the rake angle can be fluctuating (as seen to a small degree in FIGS. 43-46), regressive or progressive. A progressive change would indicate that the rake angle is at its smallest (closest to zero) adjacent the apical end 148 and grows smoothly to a maximum adjacent the stopper section 106. A progressive change in negative rake is illustrated in FIG. 36. A regressive change, on the other hand, would mean the negative rake angle is larger at the apical end 148 and grows smaller (and thus more aggressive in cutting mode) near the stopper section 106.

FIG. 36 portrays one half of the cross-sectional body portion 142 in exaggerated detail to emphasize a progressive change in the negative rake angle, as well as a progressive decrease in depth of the flutes 162. Several exemplary profiles from the one visible, helically-sectioned flute 162 appear above the cross-sectioned flute 162, with construction lines extending the rake angles for clarity. Notably, the rake angle near the apical end 148 is between about −5° and −10°. However, the rake angles become progressively more negative toward the stopper section 106. Near the terminus of the flute 162, the rake angle is about −60° or −65° which causes the working edge 172 to behave more like a compaction edge than a cutting edge when rotating in the cutting mode.

Like the rake angles, the heel-side angles can either remain generally constant (i.e., within a tolerance) along the full length of the flutes 162 or change. FIGS. 36 and 43-46 illustrate examples where the heel-side angles of the densifying faces 164 vary along the length of the flutes 162 with a total variance of less than 30°. When measuring the heel-side angle against a radial passing through the point of intersection between the densifying face 164 and its associated land surface 170 (as in FIG. 35), the heel-side angles are seen in FIG. 36 to be smallest adjacent the apical end 148, and largest adjacent the stopper section 106. In FIGS. 43-46, the heel-side angles are about 39°/42°/44°/65°, respectively. Thus, the absolute values of both the heel-side angles and rake angles may be designed to increase from a minimum adjacent the apical end 148 to a maximum adjacent the stopper section 106.

Good results have been realized when the heel-side angles are between about 15° and 55°. Even better results can be achieved by setting the heel-side angles between about 15° and 40°. And in some cases superior results have been achieved when the heel-side angles are between about 15° and 35°.

Considering the primary relief angle (also referend to as a primary taper clearance, e.g., in FIG. 16) good results have been observed when the angle is between about 6° and 34°. Even better results can be achieved by setting the primary relief angles between about 6° and 28°. And in some cases superior results have been achieved when the primary relief angles are between about 10° and 25°.

FIG. 36 is also notable for the wedge-like construction lines passing through the working edges (on the high side) and the base of the flute profiles (on the low side). These construction lines visually reinforce a feature of this exemplary embodiment where the depth of the flutes 162 intentionally changes along the length. The change in FIG. 36 is regressive, meaning that the flute 162 depth is a maximum nearest the apical end 148, and becomes smaller as it approaches the stopper section 106. Another way to describe this change in flute 162 configuration would be to consider the cross-sectional area of the flute at each point along its length. Again, with reference to the exemplary profiles in FIG. 36, the area of the flutes 162 can be seen to be smallest adjacent the stopper section 106 and largest adjacent the apical end 148. The regressive change in flute 162 depth and cross-sectional area, as shown in FIG. 36, can be combined with rake angles that are constant, that fluctuate (FIGS. 43-46), that are progressive (FIG. 36) or regressive. Likewise, regressive change in flute 162 depth and/or area can be combined with heel-side angles that are constant, fluctuating, progressive or regressive. It is believed that a regressive change in flute 162 depth and/or area combined with at least some negative rake angle is a relevant contributing factor to the advantageous cutting-mode characteristics of the enhanced rotary osteotome 136.

For embodiments in which the negative rake angle changes progressively, as in FIG. 36, satisfactory results can be obtained when the rake angles start at about 0° to −30° adjacent the apical end 148 and progress to about −45° to −70° adjacent the stopper section 106. Relief angles may be formed in the range of about 5° to 35°. And heel-side angles may be formed in the range of about 15° to 55°. However, it should be clearly understood that the progressive or regressive change in any of these attributes of the flutes 162 is not a requirement to achieve the stated advantages of the enhanced rotary osteotome 136. For example, the embodiment of FIGS. 43-46 offers a viable alternative whose rake angle is neither singularly progressive nor regressive.

Figure 37:
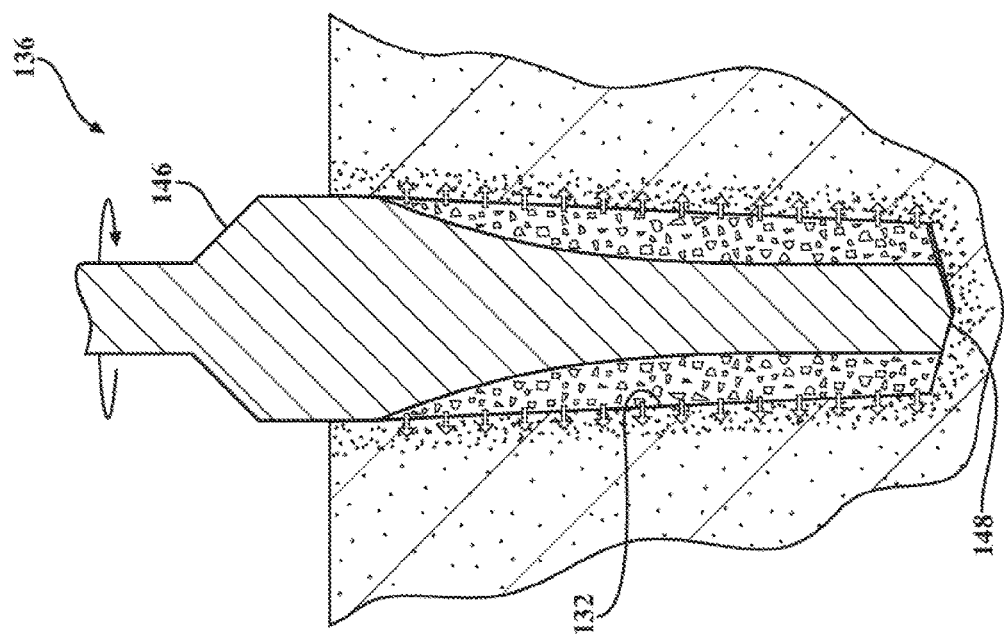
FIG. 37 is simplified cross-sectional view of the enhanced rotary osteotome as in FIG. 34 shown partially descending into a precursor osteotomy in the cutting mode.
Figure 38:
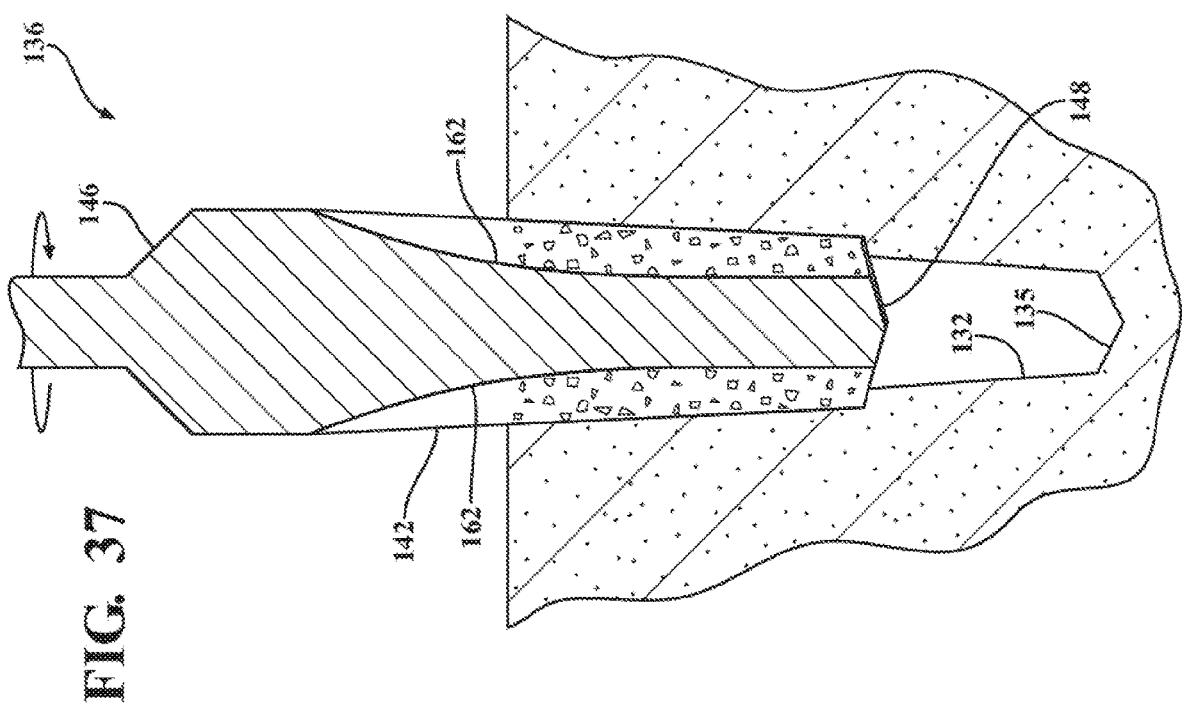
FIG. 38 is a view as in FIG. 38 but showing the enhanced rotary osteotome at full intended depth with its stopper section plugging the osteotomy so as to allow pressure build-up of the boney slurry trapped in the flutes.

When the enhanced rotary osteotome 136 is used in the cutting mode, bone particles quickly fill the flutes 162. FIGS. 37-38 depict an enhanced rotary osteotome 136 being operated in the cutting mode. Although not shown here, continuous external irrigation accompanies the procedure as in the earlier examples. In FIG. 37, the enhanced rotary osteotome 136 is descending into an osteotomy 132 in cutting mode. Bone particles are seen filling the flutes 162. Mixed with blood and collagen and irrigating fluid, the bone chips have the consistency of a semi-viscous slurry. In FIG. 38, the enhanced rotary osteotome 136 has reached its intended depth at the bottom 135 of the osteotomy 132. Observe in FIG. 38 that once the entire lengths of the flutes 162 have entered the osteotomy 132, there is no convenient egress for the bone particle slurry from the flutes 162. The stopper section 106 seals or traps the bone particles between the flutes 162 and the sidewalls of the osteotomy 132 like a cork or piston. If the surgeon continues to advance the rotating osteotome 136 deeper into the osteotomy 132, substantial resistance will be encountered. The trapped bone chip slurry will become pressurized inside the flutes 162 in response to the force of the surgeon's push. Hydraulic pressure is indicated by the tiny outwardly directed arrows in FIG. 38. The hydraulic pressure can be pulsated through the bone particle slurry, if the surgeon wishes, by the aforementioned pumping action.

Figure 40:
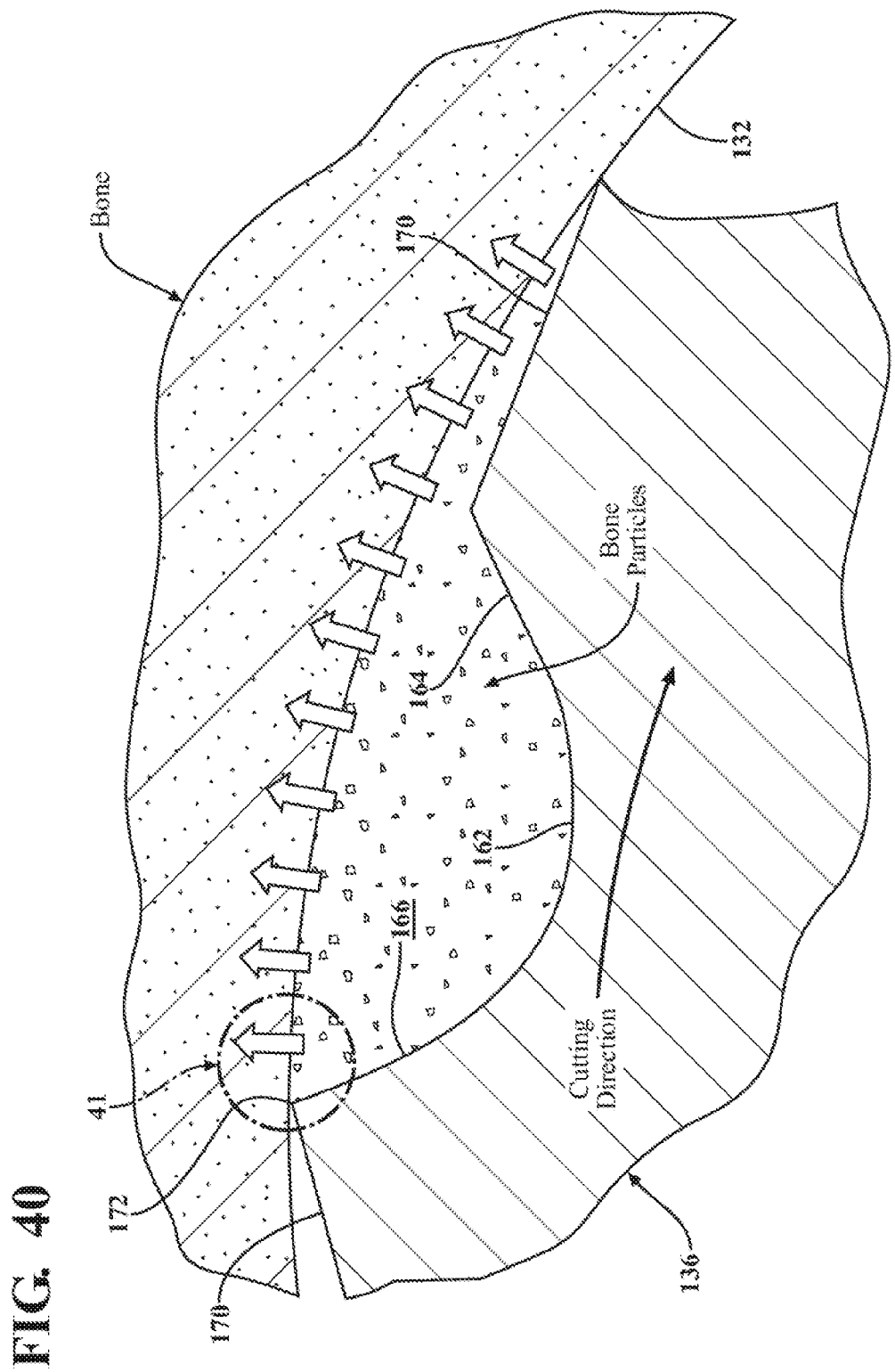
FIG. 40 is an enlarged fragmentary of a flute region for the enhanced rotary osteotome of FIG. 38 as pressure builds in the boney slurry.

FIG. 40 represents an enlarged, fragmentary cross-sectional view taken generally mid-length of the body 142. In this figure, a single flute 162 is shown with entrapped bone particles after the stopper section 106 has descended fully into the osteotomy 132 (as in FIG. 38). The enhanced rotary osteotome 136 in this illustration is being rotated in the cutting direction. The negative rake angle presented by the cutting face 166 is evident. Outwardly directed arrows indicate hydraulic pressure in the semi-viscous bone particle slurry caused, chiefly, by the continued advance of the enhanced rotary osteotome 136 after the flutes 162 have fully submerged in the osteotomy. Continued pressure causes more and more bone particles to be packed into the confined flutes 162.

Figure 41:
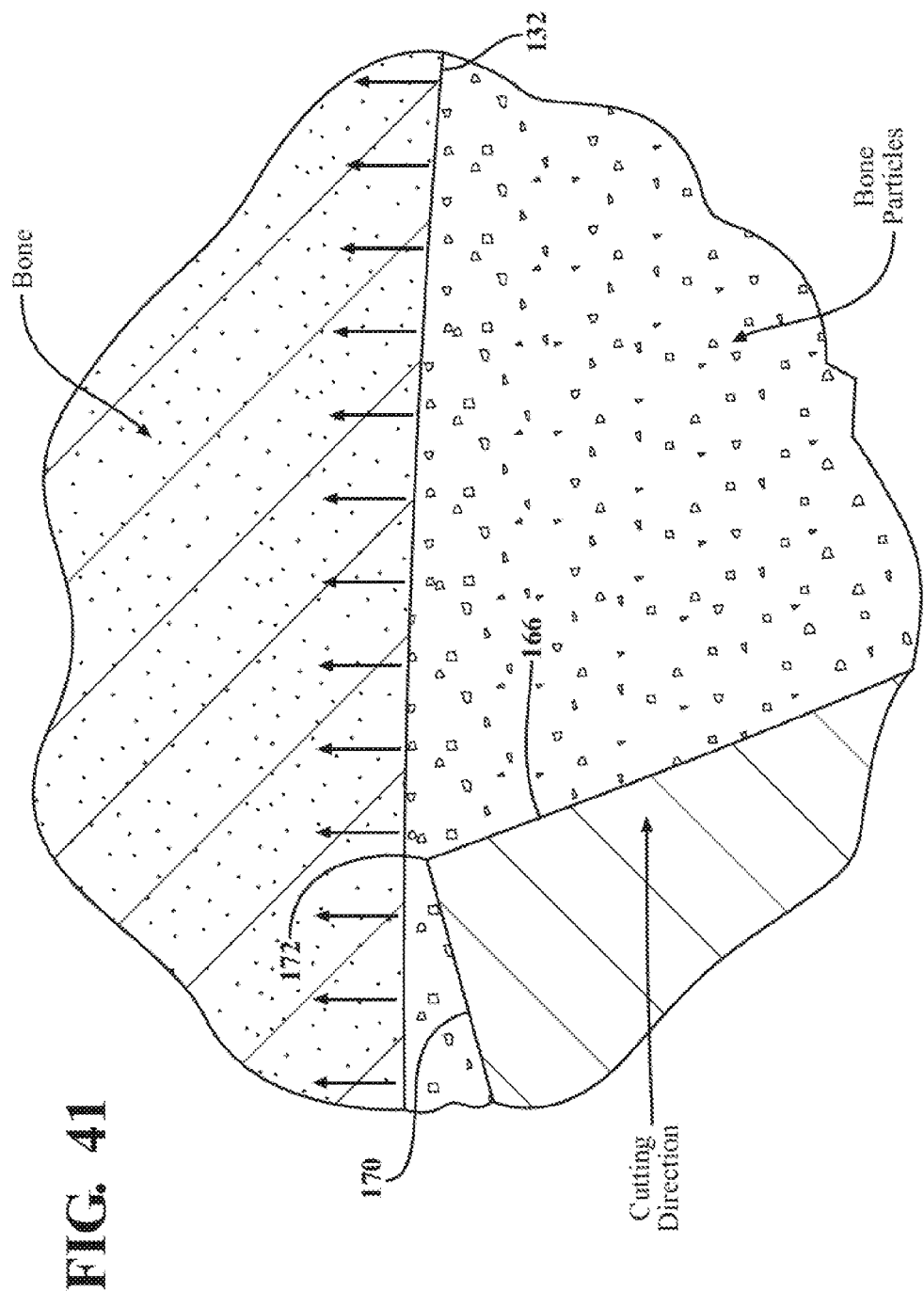
FIG. 41 is an enlargement of the area circumscribed at 41 in FIG. 40 showing the relationship between the working edge and the osteotomy sidewall after the pressure has induced a sufficiently strong strain response into the elastic or plastic range.

FIG. 41 is a highly-magnified view of the area circumscribed at 41 in FIG. 40 to show the cutting face 166 and working edge 172. Because of the high pressure generated in the semi-viscous bone particle slurry, combined with the negative rake angle at the cutting face 166, the enhanced rotary osteotome 136 operating in cutting mode begins to force the slurry into the surrounding wall surfaces of the osteotomy 132, thereby beginning to form an incipient densification crust. That is to say, the enhanced rotary osteotome 136 with negative rake angle flutes 162 will increase pressure to the point of producing an outward strain that actually separates the working edge 172 from contact with the osteotome 132 and stops the cutting action. Some of the bone particles and collagen are autografted directly back into the sidewalls of the osteotomy 132 when operating in the cutting mode. As a result, any subsequently installed implant or fixture to be screwed into the osteotomy 132 (i.e., hole in the case of non-medical applications) will benefit with heightened initial stability.

Moreover, the enhanced rotary osteotome 136 enables a novel new protocol which may be referred to as Densify-After-Cut (DAC). The DAC protocol is well-suited to hard bone conditions, in which the same enhanced rotary osteotome 136 is used to cut then densify again within the same osteotomy 132 in a single continuous operation. In an exemplary case presenting in very dense bone, a surgeon may either first begin to enlarge the osteotomy 132 in cutting mode, or perhaps may begin with densifying mode but quickly switch to cutting mode after encountering strong resistance. Regardless, the enhanced rotary osteotome 136 is advanced into the osteotomy 132 until reaching the desired depth in cutting mode, presumably due to the hard bone conditions making use of densifying mode ill-advised. Due to cutting mode action, the flutes 162 will have accumulated bone particle slurry as depicted in FIG. 38. Once the terminus of the flutes 162 at the stopper section 106 has descended inside the osteotomy 132, the early stages of autografting and condensation will begin, as described above. The osteotomy 132 is now enlarged and the surgeon may withdraw the enhanced rotary osteotome 136 and either place an implant or enlarge the osteotomy 132 further with a larger osteotome 136. Alternatively, the surgeon may instead invest a few additional seconds to apply the DAC protocol. The DAC protocol includes the following added steps. Without removing the body 142 of the enhanced rotary osteotome 136 from the osteotomy 132, the surgeon changes the drill motor to reverse (densifying mode), still set at high speed rotation, and uses centrifugal force together with the heel side flute 162 profiles and the tapered shape of the body 142 to auto-graft all of the remaining entrapped bone particles and collagen back into the osteotomy walls. Copious external irrigation continues throughout the procedure. A gentle pumping action, i.e., axial stroking of the spinning body 142 inside the osteotomy 132, is recommended so that the apical end 148 makes intermittent contact with the osteotomy bottom 135. This gentle pumping action in high-speed reverse rotation will facilitate an even formation of a full or nearly full buttressing layer (i.e., densification crust) like that seen in FIG. 22 (far-right), 23C and 23D. By not removing the body 142 of the enhanced rotary osteotome 136 from the osteotomy 132 before switching to a densifying mode of operation, the surgeon re-deposits (auto-grafts) the cut bone particles and collagen inside the host osteotomy 132.

Figure 39:
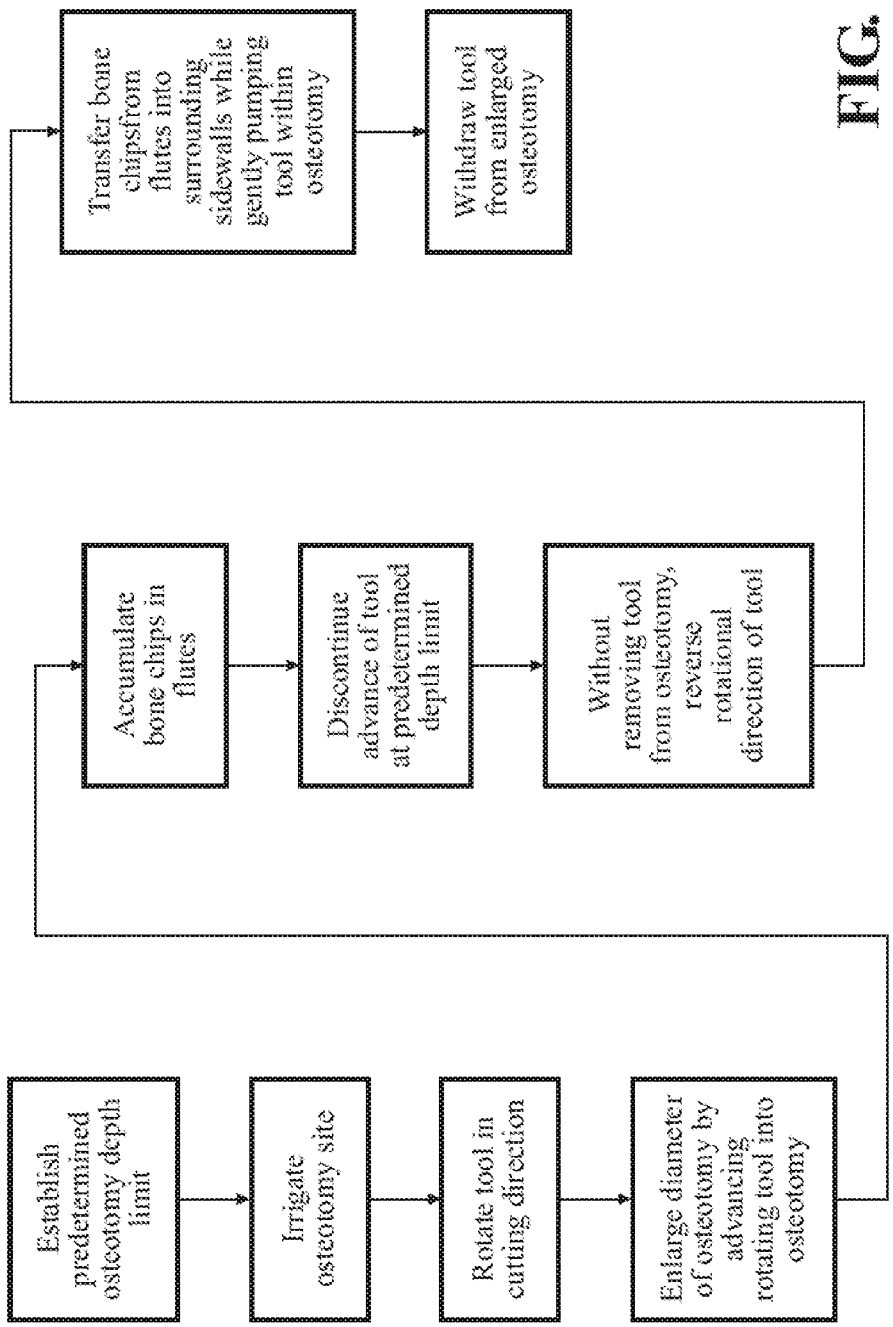
FIG. 39 is a simplified flow diagram describing an optional method referred to as the Densify-After-Cut (DAC) protocol made possible by structural configuration of the enhanced rotary osteotome.

The general steps of the DAC protocol are outlined in FIG. 39 in the form of a simplified flow diagram. In reference to that figure, the surgeon initially determines an intended depth of the osteotomy 132. This depth will have been earlier established with a pilot drilling step and possibly one or more preceding expansion steps using, preferably but not necessarily, enhanced rotary osteotomes 136 of smaller diameter(s). Considering the last expansion step only prior to placement of an implant (34, not shown), the surgeon installs an enhanced rotary osteotome 136 in his or her drill motor (38, not shown). Irrigation of the osteotomy site is expected to take place continuously throughout the procedure. The surgeon may or may not initiate the final expansion procedure in the cutting mode. Knowing that the densifying mode produces a superior densification crust, and the surgeon may initiate the final expansion procedure in densifying mode but switch to cutting mode after encountering too much resistance. Regardless of which mode is used to start the final expansion step, the surgeon completes the final expansion step in cutting mode. In cutting mode, as described above, chips and blood and collagen and irrigating fluid accumulate as a boney slurry in the flutes 162. Advance of the enhanced rotary osteotome 136 is discontinued when the apical end 148 reaches the depth limit predetermined by the surgeon. Without removing the enhanced rotary osteotome 136 from osteotomy 132, the surgeon reverses rotational direction of tool inside osteotomy 132. The semi-viscous bone chip slurry captured in the flutes 162 is transferred into the surrounding sidewalls of the osteotomy 132 by the high-speed reverse-rotating body 142. Accompanied with a gentle up and down pumping motion, the working edges 172 autograft the boney slurry directly into the osteotomy 132 walls while concurrently forming a densified crust. After only a few seconds in densifying mode, e.g., about 3-10 seconds, the surgeon withdraws the body 142 from the enlarged osteotomy 132 and proceeds with the next phase of the procedure. The DAC protocol represents an efficient method to enlarge an osteotomy 132 in hard bone using the enhanced rotary osteotome 136, while preserving (autografting) substantially all of the cut bone and collagen back into the sidewalls.

Figure 42:
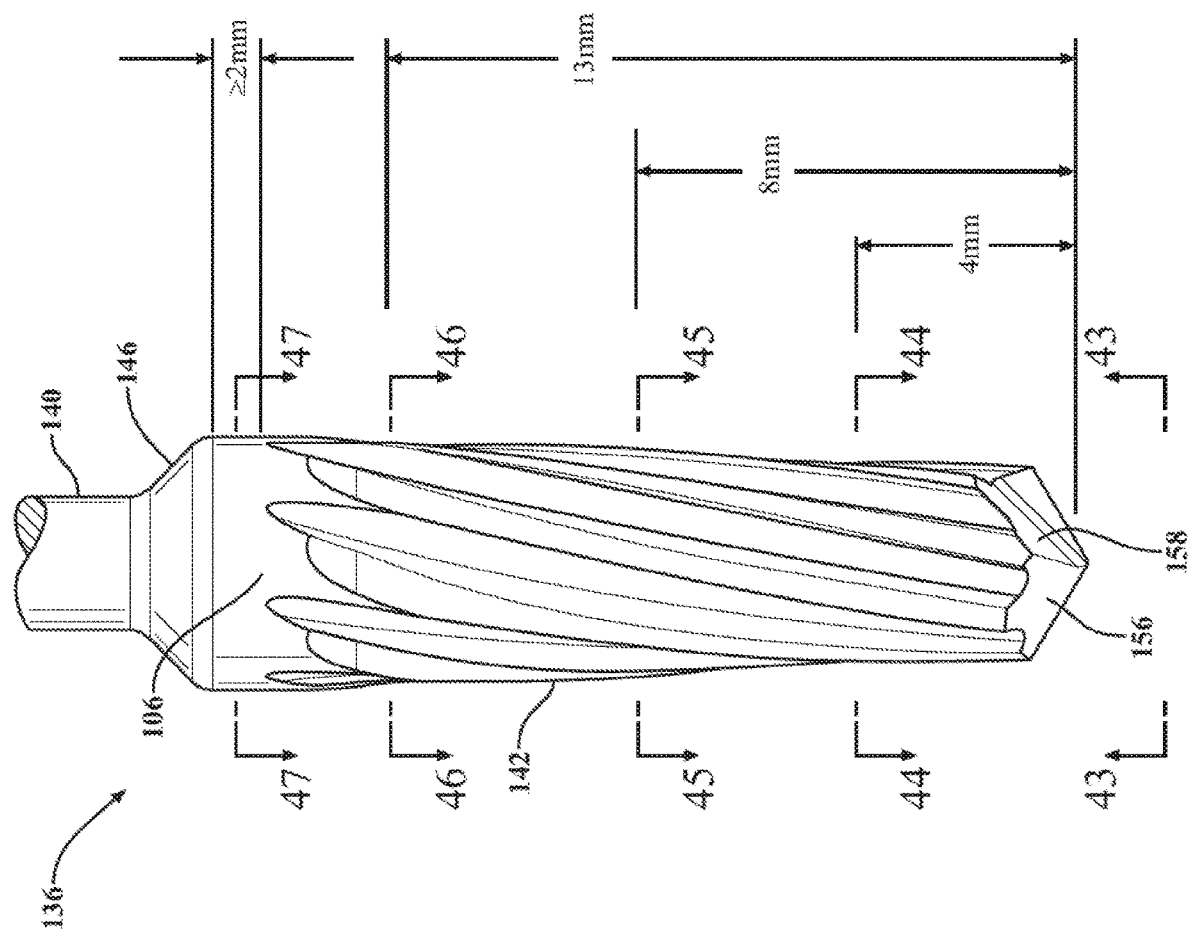
FIG. 42 is a side elevation of an enhanced rotary osteotome according to a slightly modified embodiment.
Figure 43:
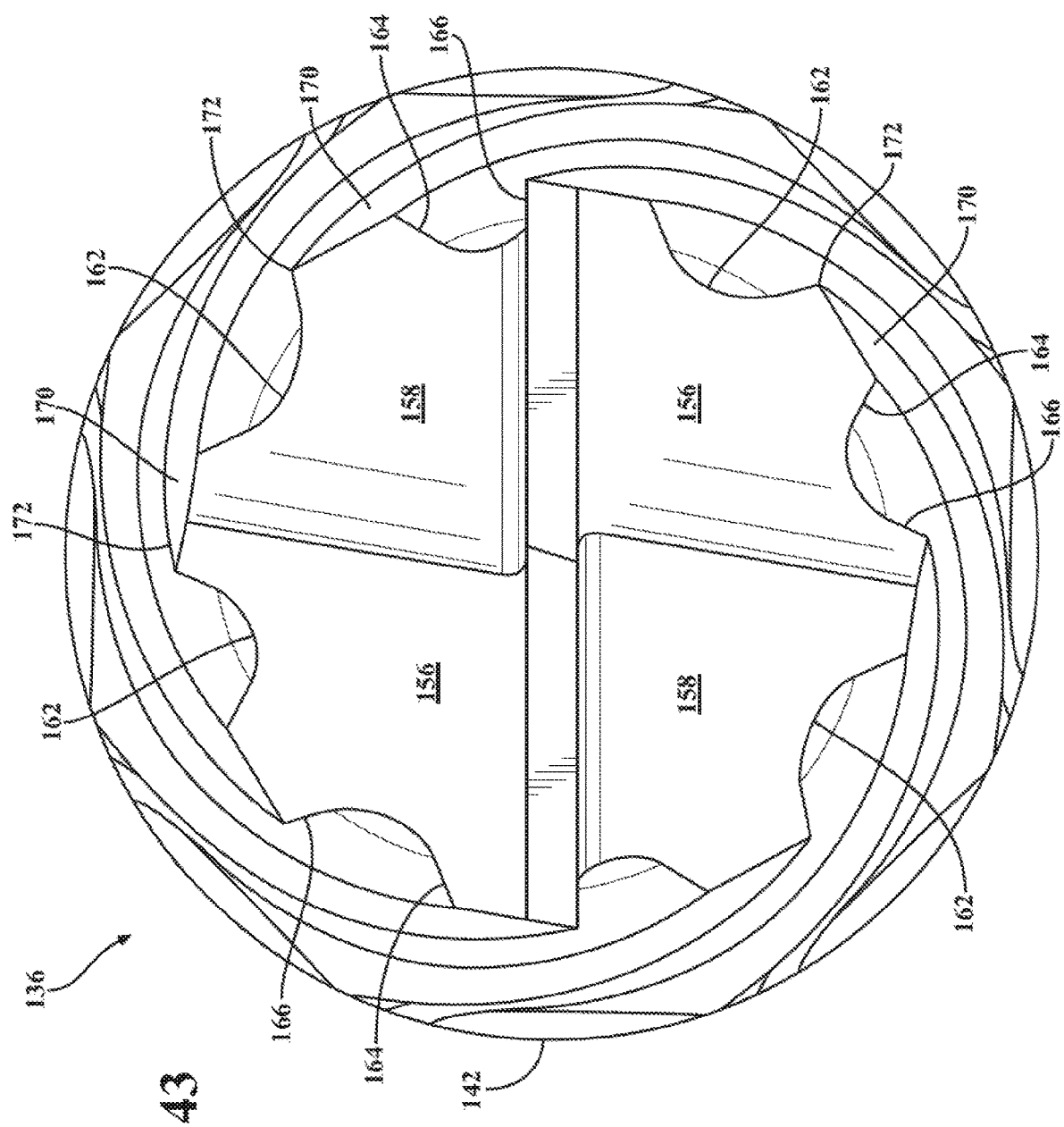
FIG. 43 is an apical end view as taken generally along lines 43-43 in FIG. 42.
Figure 44:
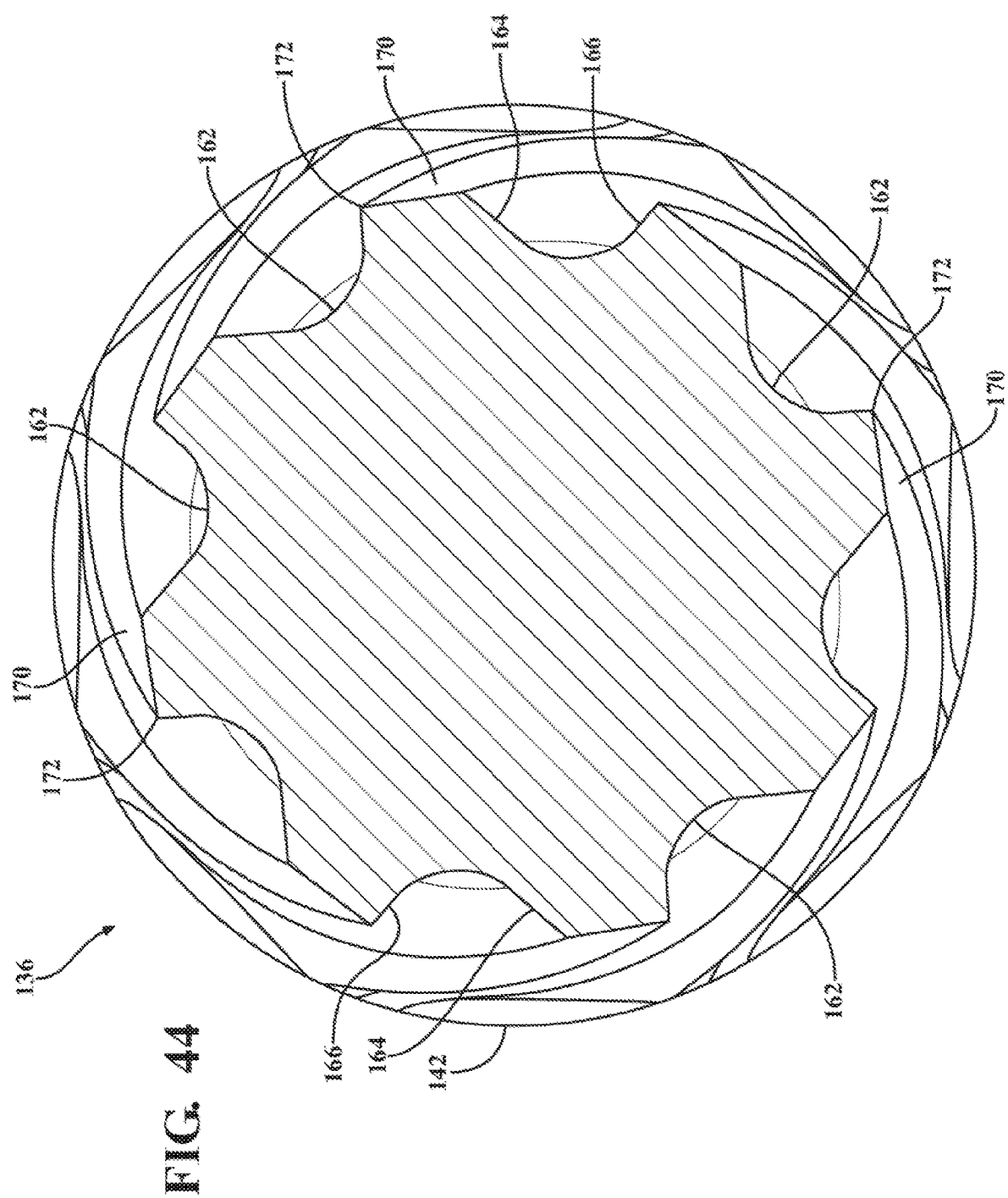
FIG. 44 is a cross-sectional view as taken generally along lines 44-44 in FIG. 42.
Figure 45:
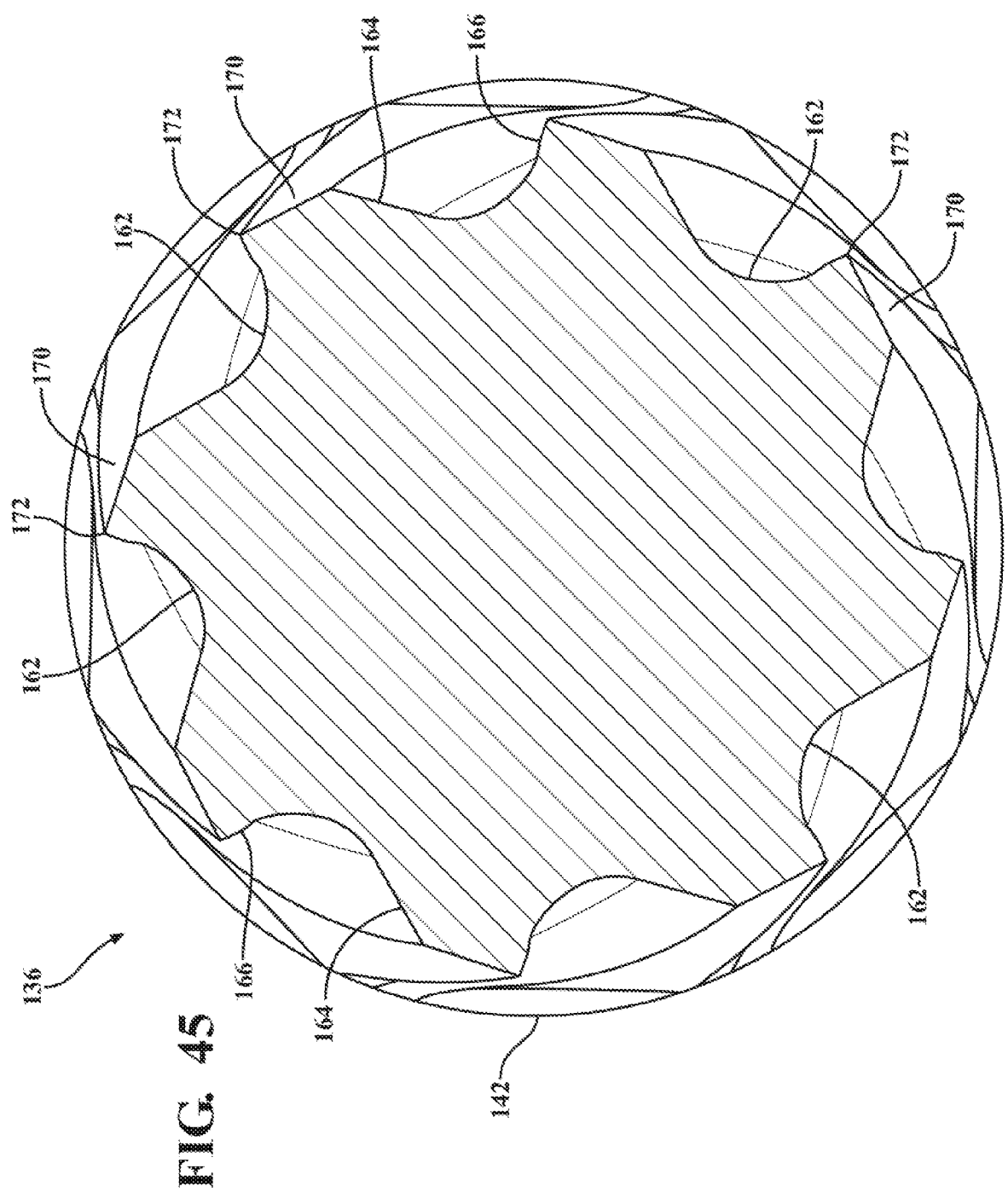
FIG. 45 is a cross-sectional view as taken generally along lines 45-45 in FIG. 42.
Figure 46:
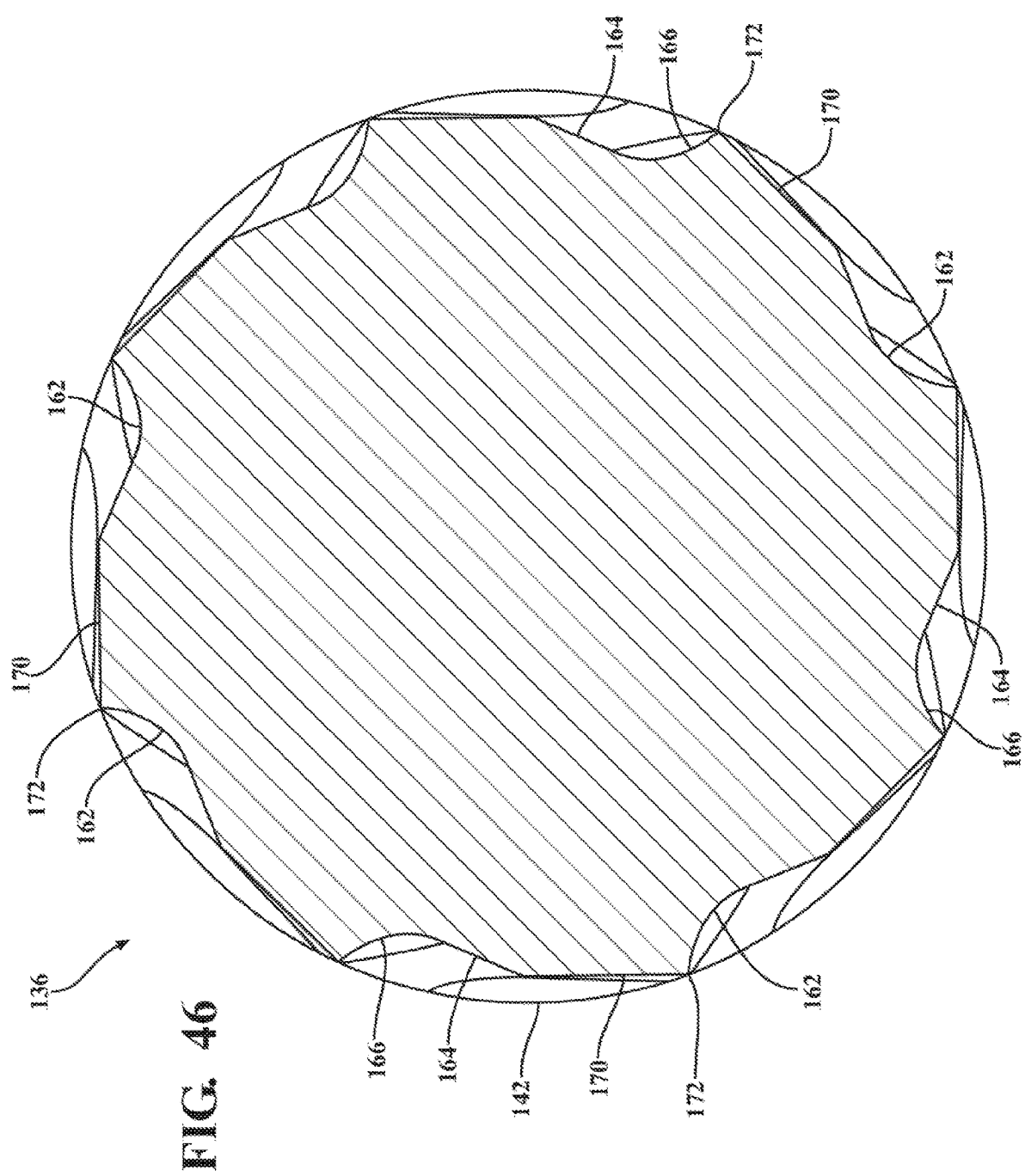
FIG. 46 is a cross-sectional view as taken generally along lines 46-46 in FIG. 42.
Figure 47:
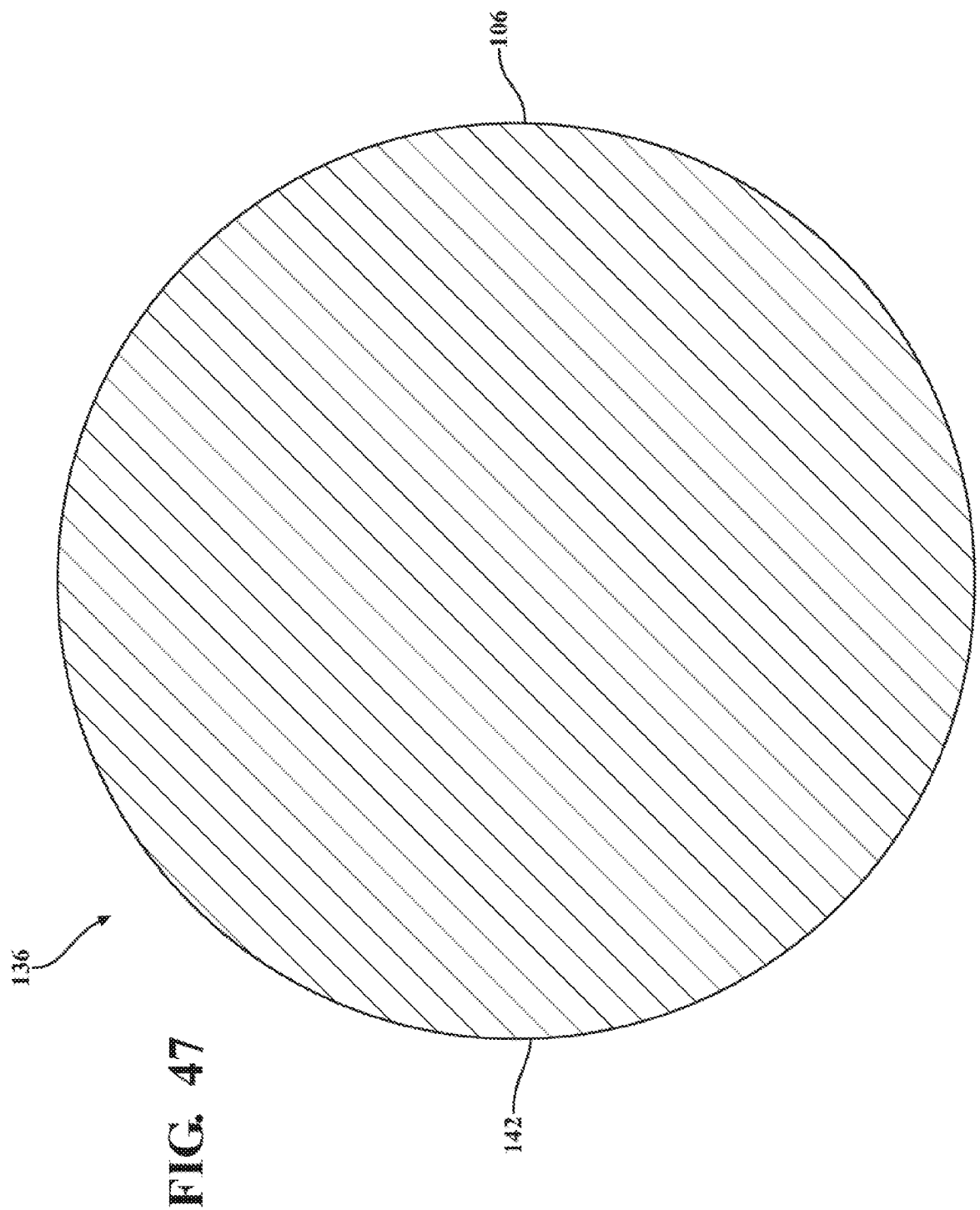
FIG. 47 is a cross-sectional view as taken generally along lines 47-47 in FIG. 42.

FIG. 42 depicts the body 142 of the enhanced rotary osteotome 136 according to one exemplary embodiment of the invention. FIG. 43 is an apical end view and FIGS. 44-47 represent lateral cross-sections taken at various elevations: 4 mm, 8 mm, 13 mm and ~15 mm, respectively, as measured from the apical end 148. In FIGS. 44-46, the cross-sections reveal the changing profiles of the flutes 162 at increasing distances from the apical end 148. Comparison of the changing inclination of the cutting faces 166 in FIGS. 43-46 will reveal the aforementioned consistently negative rake along the length of each flute 162. The end view of FIG. 43 shows the rake angles at the flutes 162 where they intersect the second trailing flanks 156 and relief pockets 158. In FIG. 43, the rake angle is least cutter-like at the points where the flutes 162 open into the respective second trailing flanks 156 and relief pockets 158. In this embodiment where the rake angle of the cutting faces 166 is never positive, these openings to the flutes 162 from the apical end 148 represent the most negative rake along the entire flute 162 length. The heel-side angle is at its minimum here at the apical end 148. Progressing next to FIG. 44 which reveals the flute 162 profiles at 4 mm from the apical end 148, the rake angles are slightly less negative and the core diameter is larger. The depth and area of the flute cross-section is slightly smaller here. The heel-side angle is shown growing also, meanwhile the land width remains generally unchanged. Moving on to FIG. 45, where the flute 162 profiles are shown at 8 mm from the apical end 148, the rake angles are slightly less negative and the core diameter is larger still, which coincides with a further reduction in the depth and area of the flute cross-section. The heel-side angle is slightly larger and the land width remains generally unchanged. In FIG. 46, where the flute 162 profiles are exposed at 13 mm from the apical end 148, very near their terminus at the stopper section 106, the rake angle is increased in the negative direction and the flutes 162 are quite shallow and small in cross-sectional area. The heel-side angle is at its maximum as well, and the land width is shown abruptly flaring to meet the nearby stopper section 106. FIG. 47 is taken through the stopper section 106, where no flutes 162 are visible.

In summarizing the novel attributes of the enhanced rotary osteotome 136, it is important to be reminded that live bone has visco-elastic properties. When subjected to a moderate strain, i.e., within the straight-line segment of the curve from the point of origin (0,0) to B as shown in FIG. 9, the bone will exhibit a generally elastic response. Continued strain beyond this point will induce a plastic deformation. The advantageous densification crust is optimally formed when an expansion-oriented (i.e., radially outward) strain is imposed on the sidewalls of the osteotomy 132 within the strain hardening range of B-to-D in FIG. 9. By trapping semi-viscous bone particles and collagen and blood within the flutes 162 during the cutting mode, the enhanced rotary osteotome 136 provokes a hydraulic pressure build-up that acts in conjunction with the working edges 172 to outwardly deform the side-walls of the osteotomy 132, as illustrated in FIGS. 38 and 40. The pressure build-up provokes an outwardly elastic response (at least initially) that has the effect of decreasing contact pressure at the working edge 72 (FIG. 41). Cutting action is retarded or perhaps even arrested altogether. This, in combination with the negative rake angles (FIG. 43) enables the enhanced rotary osteotome 136 to transition from cutting mode to autografting/densifying mode with continued high-speed rotation in the cutting direction as soon as the stopper section 106 plugs the osteotomy 132. Hydraulic pressure is generated by the piston-like effects of the stopper section 106, in combination with impeller-like attributes of the negative rake angles which produce outward force vectors. This hydraulic pressure is exerted through the bone particle slurry against the visco-elastic bone walls of the osteotomy 132. Even though the osteotome 136 is rotating at high speed in the cutting mode, further cutting action is retarded because, with sufficient pressure build-up, the side-walls of the osteotomy 132 are pushed out of direct contact with the working edge 72 as illustrated in FIG. 41. The continued strain imposed by the pressurized boney slurry onto the side walls of the osteotomy 132 will eventually exceed the point of elastic deformation (B in FIG. 9) and induce a plastic deformation in the ideal strain hardening region identified as C-to-D in FIG. 9. As a result, the modified enhanced rotary osteotome 136 is capable of producing a clean, semi-condensed osteotomy 132 when operated in cutting mode alone. Optionally, the densification crust can then be further intensified by applying the DAC protocol.

In another contemplated embodiment, not illustrated, the flutes 162 are configured to achieve both cutting and densification when operated in the cutting mode. In particular, the rake angle could be established near the apical end for maximum-aggressive cutting in the cutting mode, such as with a zero or near-zero inclination angle as in FIG. 16. However, the rake angle in this alternative embodiment would rapidly transition to negative rake. The progression to negative rake would be so aggressive that the upper portion of the flutes would begin to approach a negative rake angle equal with the primary taper clearance/relief angle so that the working edge 172 actually shifts to the other side (heel-side) of the land face 170. As a result, the upper portion of the flutes would behave as compactors even though they are rotating in the cutting direction. Although the helical twist would not be working against auto-grafting to some degree, the overall benefits may be substantial in some applications. A rotary osteotome of this configuration would never be run backwards; it would always be operated in cutting mode. For some surgical applications (and perhaps some industrial applications also), the ability to rapidly form an osteotomy (hole) with densified crust by drilling in only the cutting direction could make this option very attractive.

Figure 48:
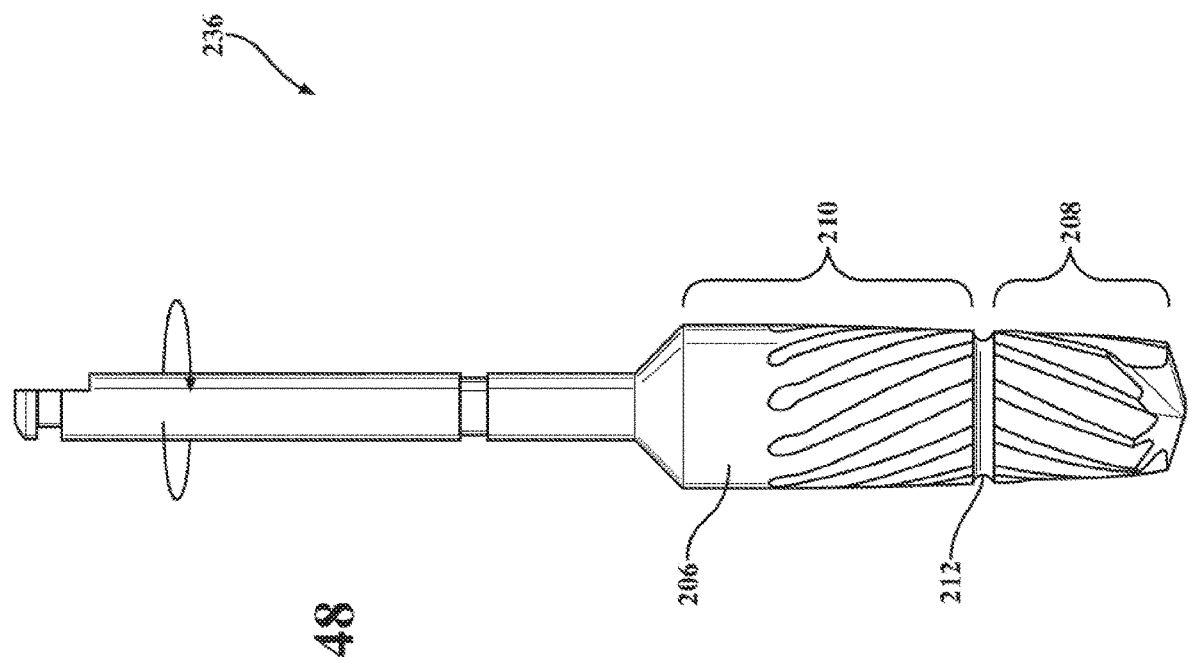
FIG. 48 is yet another alternative embodiment of the invention specially configured to produce a densifying crust while operated in the cutting mode.

Referring now to FIG. 48, yet another embodiment of the present invention will be described with a similar aim to rapidly form an osteotomy (or hole) with a densified crust by drilling only in the cutting direction. In this example, the body portion of the rotary osteotome 236 is provided with two distinct fluted sections—a lower cutting section 208 and an upper densifying section 210. The flutes of the lower cutting section 208 have a right hand helical twist to cut when the osteotome 236 is turned at high speed in the cutting mode (clockwise) direction. This is consistent with the RHS-RHC configuration shown throughout the preceding Figures. Conversely, the flutes of the upper densifying section 210 have a left hand helical twist to optimally compact when the osteotome 236 is turned at high speed in the cutting mode (clockwise) direction. The flutes of the upper densifying section 210 have a left-hand twist configuration. An annular transition zone 212 may be formed in-between the cutting 208 and compacting 210 sections.

According to this embodiment, when the rotary osteotome 236 is turned at high speed in the cutting direction and advanced into an osteotomy, semi-viscous bone particle slurry will readily flow up the flutes of the cutting section 208 and collect in the transition zone 212. The boney slurry then migrates from the transition zone 212 into the flutes of the compacting section 210 where they are auto-grafted into the inner walls of the osteotomy in the densifying mode manner described above. The transition zone 212 acts as a pre-compaction staging area or manifold where the slurry can accumulate and then find generally equalized distribution paths up the several flutes of the upper densifying section 210. The transition zone 212 also helpfully avoids the necessity for the flutes of the lower cutting section 208 to align with the flutes of the upper densifying section 210. Also, the transition zone 212 contemplates that the body portion of the osteotome 236 could be made in multiple parts which are assembled in a subsequent manufacturing operation. For example, the lower cutting section 208 could be made as a loose piece in a dedicated manufacturing operation. And likewise, the upper densifying section 210 could also be made in a dedicated manufacturing operation. The lower cutting 208 and upper densifying 210 sections could then be attached, such as by any suitable joining technique. The shank could be formed integral with the upper densifying section 210 or as yet another loose piece that is likewise joined to the composite body section. Dissimilar materials are an option in this event. For example, the lower cutting section 208 and shank could be fabricated from surgical tool steel, whereas the upper densifying section 210 is made from a suitable high-density medical grade polymer. Many options exist.

Notwithstanding, it is contemplated that the transition zone 212 is optional, such that the flutes of the lower cutting section 208 may pair in direct alignment with the flutes of the upper densifying section 210. In this latter arrangement, bone particles migrating up each flute of the lower cutting section 208 will proceed directly into a corresponding flute of the upper densifying section 210 for deposition into the side wall of the osteotomy in the manner described above. An advantage of the alternative embodiment of FIG. 48 is that the osteotomy can be prepared—both cut and densify— with a continuous forward cutting action thereby saving time and simplifying the procedure.

It bears reiterating that all embodiments of the present invention, including those described in connection with FIGS. 33-48, may be used in non-medical applications for metals and foams and other non-organic materials. In such instances, the osteotome 36, 136, 236 is re-named as a tool or rotary tool as the term osteotome implies specifically use in bone. And indeed, all references to bone and boney slurries can be easily reimagined by those of skill in the art as the relevant inorganic material serving as host for the hole being enlarged. Also, although in the illustrated embodiments the body 42, 142 is tapered, the novel attributes and spirit of this invention may be accomplished within the context of a non-tapered (i.e., cylindrical) body.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A rotary osteotome operable in a cutting direction and a reverse densifying direction, comprising:
a shank establishing a longitudinal axis of rotation for the cutting and reverse densifying directions,
a body extending from said shank, said body having an apical end remote from said shank, a plurality of helically spiraling flutes disposed about said body, each said flute having a cutting face on one side thereof defining a rake angle and a densifying face on the other side thereof defining a heel-side angle, for each said densifying face the associated said heel-side angle is a positive angle measured in the cutting direction, said flutes having an axial length and radial depth, a stopper section of said body disposed between said flutes and said shank, a land formed between each adjacent pair of flutes, each said land having a working edge along said cutting face of the one adjacent said flute, said working edge helically twisting about said body,
wherein the improvement comprises:
for each said cutting face at least a portion of the associated said rake angle is a negative rake angle measured in the cutting direction.

2. The rotary osteotome of claim 1, wherein said flutes have a regressive depth measuring deepest adjacent said apical end and shallowest adjacent said stopper section.

3. The rotary osteotome of claim 1, said negative rake angle fluctuates along the length of each said flute with a total variance of less than 30°.

4. The rotary osteotome of claim 1, wherein said negative rake angle fluctuates along the length of each said flute with a total variance of greater than 30°.

5. The rotary osteotome of claim 1, wherein said negative rake angle changes along the length of each said flute in a progressive manner.

6. The rotary osteotome of claim 1, wherein said negative rake angle changes along the length of each said flute in a regressive manner.

7. The rotary osteotome of claim 1, wherein said heel-side angle is generally constant along the length of each said flute.

8. The rotary osteotome of claim 1, wherein said heel-side angle fluctuates along the length of said flutes with a total variance of less than 30°.

9. The rotary osteotome of claim 8, wherein said working edges wind about said body in a direction that turns away from a non-cutting direction as said conically tapered profile decreases in diameter.

10. The rotary osteotome of claim 1, wherein said body has a conically tapered profile decreasing from a maximum diameter adjacent said shank to a minimum diameter adjacent said apical end.

* * * * *

UNITED STATES PATENT AND TRADEMARK OFFICE
CERTIFICATE OF CORRECTION

PATENT NO. : 10,980,548 B2
APPLICATION NO. : 16/069967
DATED : April 20, 2021
INVENTOR(S) : Salah Huwais It is certified that error appears in the above-identified patent and that said Letters Patent is hereby corrected as shown below:

In the Claims

Claim 9 and 10 should be amended to read as follows:

9. The rotary osteotome of claim 1, wherein said body has a conically tapered profile decreasing from a maximum diameter adjacent said shank to a minimum diameter adjacent said apical end.

10. The rotary osteotome of claim 9, wherein said working edges wind about said body in a direction that turns away from a non-cutting direction as said conically tapered profile decreases in diameter.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*